US011879000B2

(12) United States Patent
Saleh et al.

(10) Patent No.: US 11,879,000 B2
(45) Date of Patent: Jan. 23, 2024

(54) PURIFICATION AND IDENTIFICATION OF A PROTEIN COMPLEX CONTAINING B-CELL LYMPHOMA PROTEIN (BCL10)

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Ayman Mahmoud Saleh, Jeddah (SA); Mamoun Ahmad Salim Ahram, Amman (JO); Amre Osman Nasr, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA); King Abdulaziz City for Science and Technology, Riyadh (SA)

( * ) Notice: Subject to any disclaimer, the term of this patent is extended or adjusted under 35 U.S.C. 154(b) by 1023 days.

(21) Appl. No.: 16/685,565

(22) Filed: Nov. 15, 2019

(65) Prior Publication Data
US 2021/0148907 A1 May 20, 2021

(51) Int. Cl.
*C12Q 1/6883* (2018.01)
*C07K 14/47* (2006.01)
*G01N 30/08* (2006.01)
*G01N 33/68* (2006.01)
*G01N 30/06* (2006.01)

(52) U.S. Cl.
CPC ........ *C07K 14/4747* (2013.01); *C12Q 1/6883* (2013.01); *G01N 30/08* (2013.01); *G01N 33/6893* (2013.01); *C12Q 2600/158* (2013.01); *G01N 2030/067* (2013.01); *G01N 2500/02* (2013.01); *G01N 2500/10* (2013.01)

(58) Field of Classification Search
CPC .............. C07K 14/4747; C12Q 1/6883; C12Q 2600/158; G01N 30/08; G01N 33/6893; G01N 2500/02; G01N 2500/10
See application file for complete search history.

(56) References Cited

U.S. PATENT DOCUMENTS

| | | | |
|---|---|---|---|
| 7,736,677 B2 | 6/2010 | Tripp et al. | |
| 2006/0177847 A1 | 8/2006 | Cox et al. | |
| 2007/0060743 A1 | 3/2007 | Tang et al. | |
| 2009/0087423 A1 | 4/2009 | Sunahara et al. | |
| 2014/0296181 A1 | 10/2014 | Arnold et al. | |

FOREIGN PATENT DOCUMENTS

| | | |
|---|---|---|
| JP | 2018-517674 A | 7/2018 |
| WO | WO 2018/231322 A1 | 12/2018 |

OTHER PUBLICATIONS

Tong, Xuhui, et al. "Targeting cell death pathways for cancer therapy: recent developments in necroptosis, pyroptosis, ferroptosis, and cuproptosis research." Journal of Hematology & Oncology 15.1 (2022): 1-32. (Year: 2022).*
Zhang, Tao, et al. "NF-κB signaling in inflammation and cancer." MedComm 2.4 (2021): 618-653. (Year: 2021).*
Ekambaram, Prasanna, et al. "The CARMA3-Bcl10-MALT1 Signalosome Drives NFκB Activation and Promotes Aggressiveness in Angiotensin II Receptor-Positive Breast Cancer." Cancer research 78.5 (2018): 1225-1240. (Year: 2018).*
Iranzu Lamberto, et al., "Bisacylimidoselenocarbamates cause G2/M arrest associated with the modulation of CDK1 and Chk2 in human breast cancer MCF-7 cells", Current Medicinal Chemistry, Jan. 2013, pp. 1-31.
Izabella Thais Silva, et al., "Cytotoxicity of AMANTADIG—a semisynthetic digitoxigenin derivative—alone and in combination with docetaxel in human hormone-refractory prostate cancer cells and its effect on Na+/K+-ATPase inhibition", Biomedicine & Pharmacotherapy, vol. 107, Nov. 2018, pp. 464-474 (Abstract only).
Yu-Hsiang Lee, et al., "Fluid Shear Stress Induces Cell Cycle Arrest in Human Urinary Bladder Transitional Cell Carcinoma Through Bone Morphogenetic Protein Receptor-Smad1/5 Pathway", Cellular and Molecular Bioengineering, vol. 11, Issue 3, Jun. 2018, pp. 185-195 (Abstract only).
Shuo Chen, et al., "MicroRNA-490-3P targets CDK1 and inhibits ovarian epithelial carcinoma tumorigenesis and progression", Cancer Letters, vol. 362, Issue 1, Jun. 28, 2015, pp. 122-130 (Abstract only).

* cited by examiner

*Primary Examiner* — Nancy J Leith
*Assistant Examiner* — Khaleda B Hasan
(74) *Attorney, Agent, or Firm* — Oblon, McClelland, Maier & Neustadt, L.L.P.

(57) ABSTRACT

A method for isolating a protein complex comprising BCL10 and at least one, preferably all, of ROS1, LSD1, BTK, KU80, KU70, CUL4A, IMP3, thioredoxin, hTID1, DAP3, CDK1/CDC2, PRL1/PTP4A1 or NM23. Methods for using this complex to diagnose or prognose diseases including diabetes, obesity, cancer, neurodegenerative disease or inflammatory diseases associated with activation of NF-κB. Methods for distinguishing lean, obese and diabetic subjects based on expression of BCL10 and its ligands are also disclosed. The invention also pertains to pharmaceutical compositions comprising ligands for BCL10 or other components of this complex or agents such as siRNA or miRNA that regulate the expression of the protein components of this complex.

19 Claims, 23 Drawing Sheets
Specification includes a Sequence Listing.

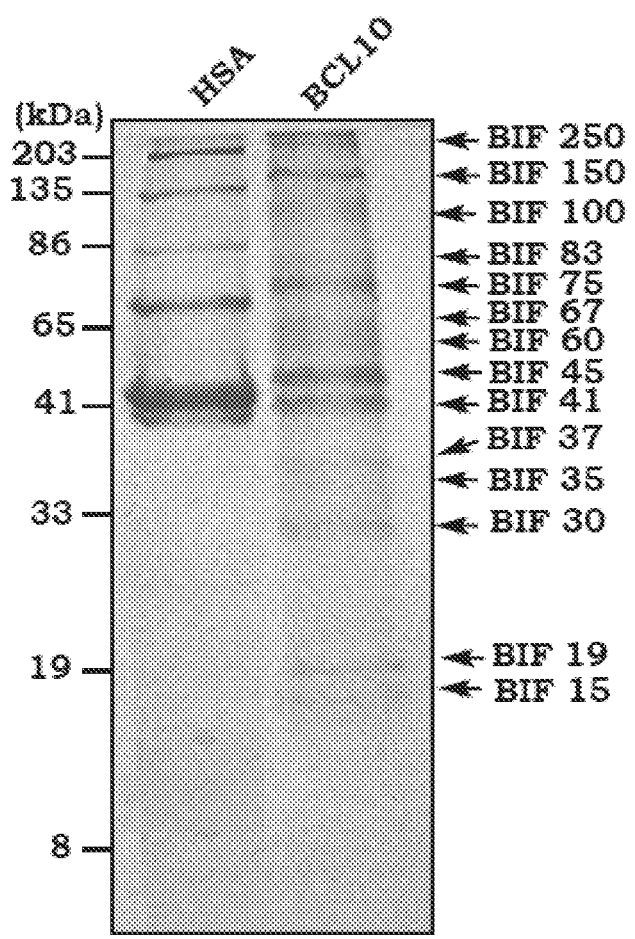

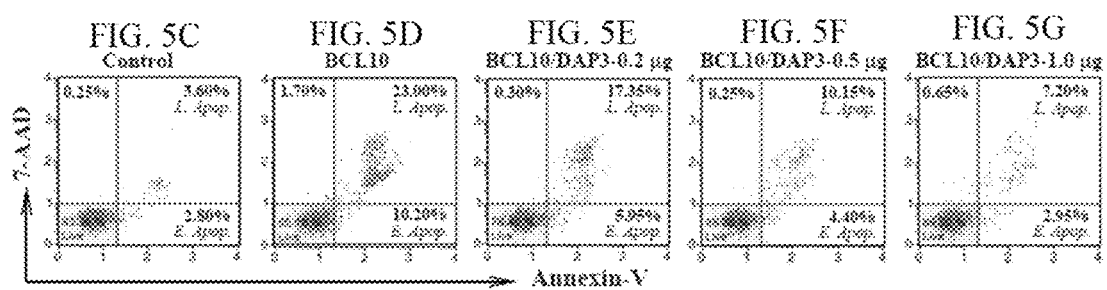

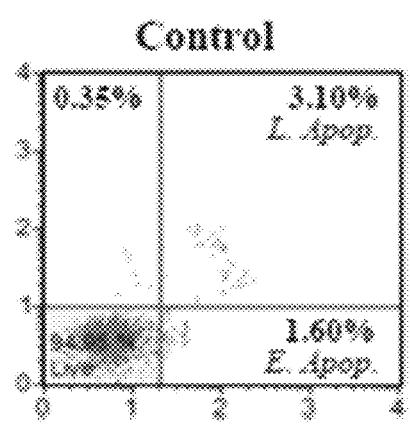
FIG. 6B
Control
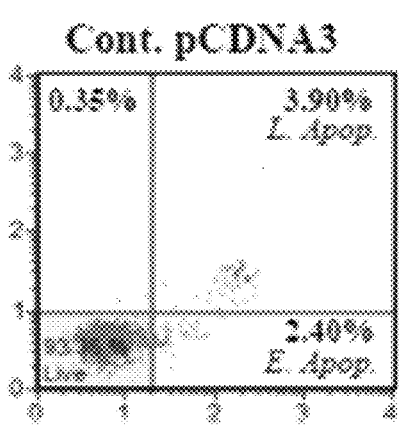
FIG. 6C
Cont. pCDNA3
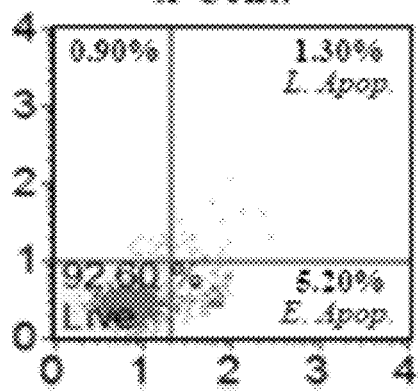
si-Cont.
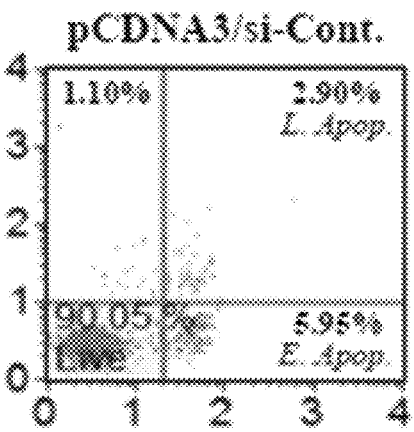
pCDNA3/si-Cont.
FIG. 6D            FIG. 6E FIG. 6F
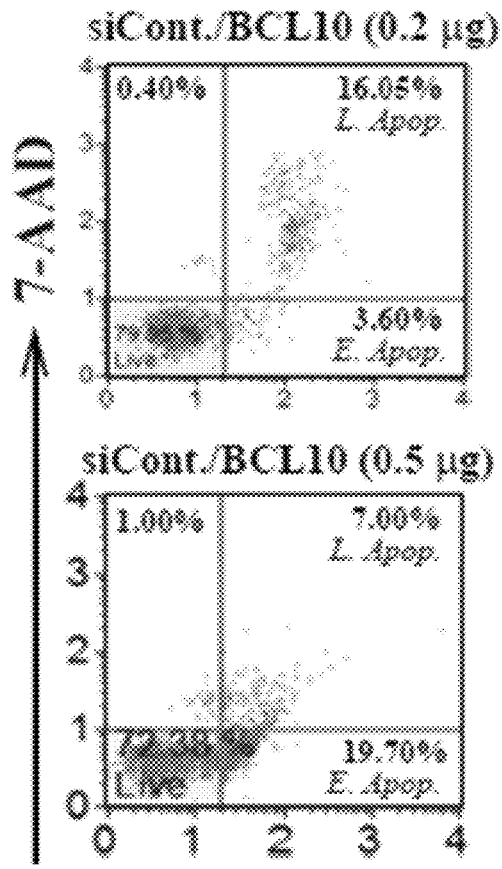
FIG. 6G
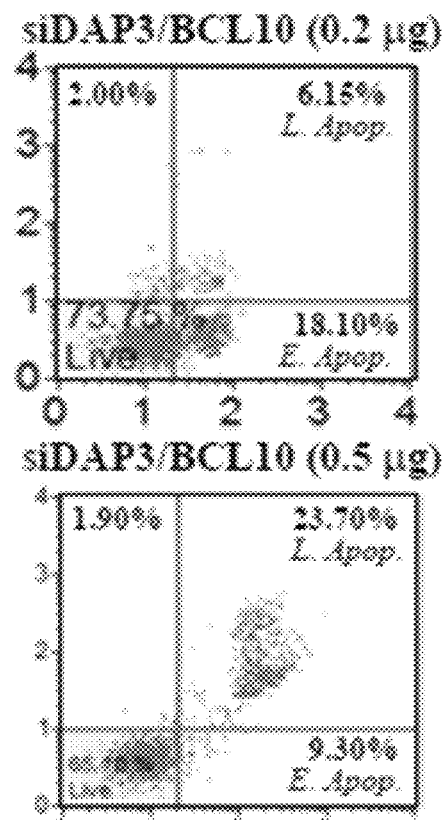
FIG. 6H  FIG. 6I
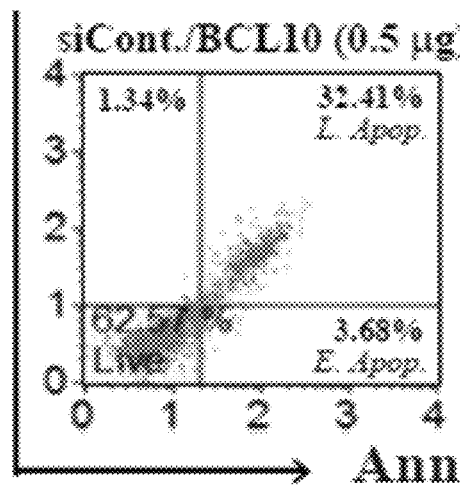
FIG. 6J
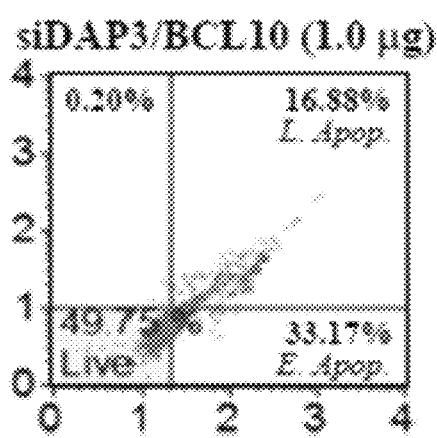
FIG. 6K

US 11,879,000 B2

PURIFICATION AND IDENTIFICATION OF A PROTEIN COMPLEX CONTAINING B-CELL LYMPHOMA PROTEIN (BCL10)

REFERENCE TO A SEQUENCE LISTING

In accordance with 37 CFR § 1.52(e)(5), the present specification makes reference to a Sequence Listing submitted electronically as a .txt file named "521462US_ST25.txt". The .txt file was generated on Nov. 15, 2019 and is 79,205 bytes in size. The entire contents of the Sequence Listing are hereby incorporated by reference.

BACKGROUND OF THE INVENTION

Field of the Invention

The invention falls within the fields of medicine and protein chemistry. It pertains to a protein complex of BCL10, a method for isolating a protein complex of BCL10 and BCL10 interacting factors ("BIFs"), and diagnostic, prognostic and therapeutic methods involving this complex.

Description of the Related Art

The BCL10 gene was discovered in 1999 as a result of a translocation mutation between chromosomes 1p22 and 14q32 [t(1;14)(p22;q32)] which is directly involved in Mucosa-Associated Lymphoid Tissue (MALT) lymphomas.

Overexpression of BCL10 in different mammalian cell lines promotes apoptosis, activation of NF-κB and suppresses malignant transformation of rat embryonic fibroblasts. Truncated BCL10 mutants, isolated from MALT lymphoma tumors, are defective in their proapoptotic function and exhibit enhancement of cellular transformation activity. In addition to MALT lymphoma, truncated mutations of the BCL10 gene that abolish its proapoptotic function have been reported to occur at high frequencies in several malignancies, including mantle cell lymphoma, various types of leukemia, hepatocellular carcinoma and colorectal cancer. BCL10 is functionally involved in regulating cellular growth and development. BCL10 is also required for antigen-surface receptor signaling in both B and T lymphocytes, and for developing innate and adaptive immunity and is involved in the signaling pathways of lymphokines and cytokines, therefore, it is associated with various types of inflammatory disorders such as atherosclerosis and AIDS viral infections. Recent studies have also suggested a role for this factor in obesity, development of acute and chronic insulin resistance and diabetes.

Most of the reported work about BCL10 is related to its ability to signal activation of the transcription factor NF-κB through its ability to form a complex with two other components, CARD11 and MALT1.

Despite all these findings, the mechanism through which BCL10 induces apoptosis to inhibit cellular transformation has not been determined and thus targets useful for diagnosis or therapy have not been identified. In addition, the mechanism of NF-κB activation by BCL10 and its effect on cell growth remains to be elucidated. Thus, while some of the roles of BCL10 in immunity and diseases including various types of hematological and solid tumors, inflammatory disorders, autoimmune diseases, neurodegeneration and diabetes have been documented, the mechanisms by which this key regulator can cause these disorders are poorly understood due to lack of information about the cellular signaling factors that associate with BCL10. This lack of information has hindered targeting BCL10 to diagnose and treat its associated diseases for more than twenty years.

Accordingly it is one object of the present disclosure to describe methods, protein complexes that derive from or are involved in the mechanism and role of BCL10.

SUMMARY OF THE INVENTION

A method for isolating protein complex (also called a megaprotein complex due to its large size) comprising BCL10 and other proteins or BIFs with which it is associated with inside of a cell is described. This method involves isolating BCL10 in a complex with at least one of ROS1, LSD1, BTK, KU80, KU70, CUL4A, IMP3, thioredoxin, hTID1, DAP3, CDK1/CDC2, PRL1/PTP4A1 and NM23.

The invention also pertains to a composition comprising this BCL10-containing protein complex and methods for diagnosis and treatment using it or methods for using antibodies or other ligands that bind to one or more components of the protein complex, for diseases in which apoptosis plays a role, such as cancer or neurodegenerative disease, or for disease involving the activation of NF-κB such as autoimmune diseases, neurological diseases or diabetes.

The invention also involves methods for modifying the interactions or expression of one or more of the proteins or BIFs composing the protein complex, for example, using antibodies or other ligands which recognize components of the complex or using siRNA or miRNA or other genetic methods. For example, these methods may modulate the expression or interaction of DAP3, or ROS1, BTK or CDK1, themselves BIFs, with BCL10 or other components of the protein complex.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2C. The eluted proteins from the HSA and BCL10 affinity columns as visualized after Coomassie blue staining.

FIGS. 5C-5G show representations for the flow cytometry plots for one experiment.

FIGS. 6B-6K show flow cytometry plots.

DETAILED DESCRIPTION OF THE PREFERRED EMBODIMENTS

Figure 1A:
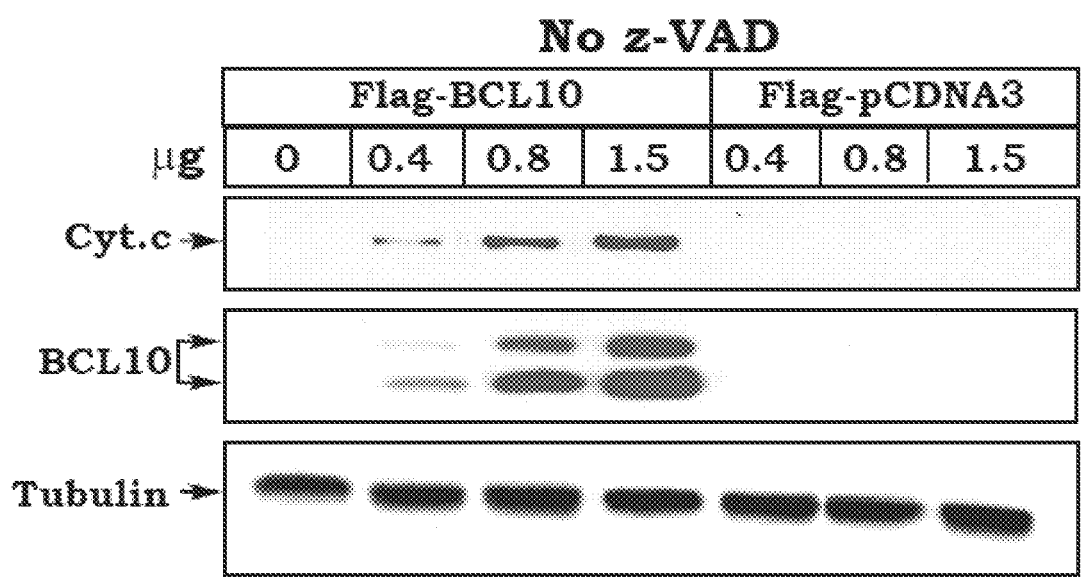
FIGS. 1A-1C. Western blots showing that the proapoptotic function of BCL10 is mediated through release of cytochrome c from mitochondria.

A BCL10-containing protein complex comprising BCL10 and thirteen BIFs is described, isolated and identified. This previously unknown complex permitted the identification of new targets for diagnostic and therapeutic applications. The roles of various components of the BCL10-containing protein complex in apoptosis, activation of NF-KB, and in diseases such as diabetes and uses to treat disease states are demonstrated.

The BCL10-containing complex was isolated by a series of steps including affinity purification using bound recombinant BCL10 protein. Mass-spectrometry analysis of the components of the complex identified thirteen proteins or BIFs that associate with BCL10. These proteins are ROS1, LSD1, BTK, KU80, KU70, CUL4A, IMP3, thioredoxin, hTID1, DAP3, CDK1/CDC2, PRL1/PTP4A1 and NM23. The association between BCL10 and ten of these factors was confirmed in vivo in HeLa and Jurkat cells by co-immunoprecipitation of LSD1, BTK. KU80, KU70, CUL4A, IMP3, Thioredoxin, hTID1, DAP3 and NM23 along with BCL10.

The in vivo association between BCL10 and a member of its complex, namely, the death-associated protein DAP3, has been further characterized. It was shown that DAP3 regulates the function of the complex by inhibiting the apoptotic function of BCL10 to trigger the release of cytochrome c from the mitochondria of HeLa cells. DAP3 also enhances the ability of the complex to activate NF-κB in both HeLa and Jurkat cells. However, it was also found that the overexpression of BCL10 suppresses expression of the gene encoding DAP3. Among other aspects, the invention is directed to methods for modulating the interaction of DAP3 with a BCL10-containing complex, for example, by use of chemical, physical, cellular, genetic, or protein-based interventions.

In addition to describing the interaction of DAP3 and the BCL10 protein complex, a phosphorylating interaction of BCL10 with at least one of ROS1, BTK or CDK1 is described, identified and characterized. The interaction of these components with the BCL10-containing complex may also be modulated by chemical, physical, cellular, genetic, or protein-based intervention.

The expression levels of various components of the BCL10 protein complex in non-diabetic, obese and diabetic subjects were also determined for eight components of the complex-BCL10, LSD1, CUL4A, CUL4B, KU70, hTID1, DAP3 and NM23. The expression of NF-κB1 was also determined in these subjects. Expression levels of these components correlate with the status of a patient, for example, whether the patient is diabetic or non-diabetic or lean or obese.

The BCL10-containing complex contains BCL10 in association with BIFs ROS1, LSD1, BTK, KU80, KU70, CUL4A, IMP3, thioredoxin, hTID1, DAP3, CDK1/CDC2, PRL1/PTP4A1 and/or NM23. Background information about these BIFs is described and provided below.

The ROS1 oncogene encodes the Orphan Receptor Tyrosine kinase (RTK) which is related to the anaplastic lymphoma kinase (ALK) and members of the insulin-receptor family. This receptor protein is involved in signaling cellular growth and differentiation. The proto-oncogenic activity of ROS1 is triggered by chromosomal rearrangement mutations which are found in many human cancers, including non-small-cell lung cancer (NSCLC), gastric cancer, cholangiocarcinoma, ovarian cancer, glioblastoma, and cancers of the bile duct and rectum. ROS1 gene rearrangements result in the formation of fusion proteins having constitutive tyrosine kinase activity. The biological role of native ROS1 in humans was not previously defined and ROS1 was an orphan RTK without a known ligand.

LSD1 (KIAA0601) encodes a protein sharing significant sequence homology with FAD dependent amine oxidases which are able to demethylate lysine and argentamine residues of histones and act as transcriptional co-repressors.

BTK oncogenic mutations in the Bruton's tyrosine kinase (BTK) have been found in all B cell malignancies. BTK is a none-receptor kinase that is involved in the development of B lymphocytes at various stages and BTK plays a role in signaling downstream the B cell receptor (BCR). It is also involved in signal transduction pathways of chemokine receptor, Tolllike receptor (TLR) and Fc receptor in B cells. In addition to its expression in B lymphocytes, BTK is also expressed in the lineages of myeloid cells. This kinase is also involved in the signaling and activation of many other pathways including NF-κB in osteoclasts. While many of these pathways are shared by BCL10, the relationship between both proteins was not previously reported.

KU70/KU80 heterodimer. KU is an abundant highly conserved DNA binding protein, found in both prokaryotes and eukaryotes and plays essential roles in the maintenance of the integrity of the genome. In eukaryotes, KU is a heterodimer comprised of two subunits, KU70 and KU80 that is best characterized for its central role as the initial DNA end binding factor in the "classical" non-homologous end joining (C-NHEJ) pathway, the main DNA double-strand break (DSB) repair pathway in mammals. KU binds to double-stranded DNA ends with a high affinity in a sequence-independent manner through a central ring formed by the intertwined strands of the KU70 and KU80 subunits. At the break, KU directly and indirectly interacts with several C-NHEJ factors and processing enzymes, serving as the scaffold for the entire DNA repair complex. There is also evidence that KU is involved in signaling to the DNA damage response (DDR) machinery to modulate the activation of cell cycle checkpoints and apoptosis. KU is also associated with telomeres. Overall, KU functions are critical for maintaining the genomic integrity and proper cellular and organismal development.

CUL4A belongs to the cullin family of ubiquitin ligase proteins and is highly homologous to the CUL4B protein. CUL4A regulates numerous key processes such as DNA repair, chromatin remodeling, spermatogenesis, haematopoiesis and mitotic cell cycle. As a result, CUL4A has been implicated in several cancers and the pathogenesis of certain viruses including HIV.

IMP3. The insulin-like growth factor II (IGF-II) messenger RNA (mRNA)-binding protein-3 (IMP3), which has also been referred to as the K homology domain containing-protein and as L523S, is a member of the IMP family composed of IMP1, IMP2, and IMP3. IMP3 binds to the 5'untranslated region of the IGF-II leader-3 mRNA as a translational activator of IGF-II leader-3 mRNA, which controls cell proliferation.

Thioredoxin (TRX). TRX is an oxidoreductase enzyme containing dithiol-disulfide active site. There are TRX isoforms in most organisms, and they exist as separate TRX systems for cytoplasm and mitochondria. TRX acts as a protein disulfide reductase and an electron donor for other enzymes such as ribonucleotide reductase and peroxidase.

hTID1. The human tumorous imaginal disc1 hTID1 was first identified as a human homologue of *Drosophila* tumor suppressor protein TID56. hTID1 belongs to the DnaJA3 family of proteins that are known to interact with HSP70 family proteins. At least two isoforms of hTID1, namely, hTID1L and hTID1S, have been reported. Both isoforms contain an amino-terminal mitochondrial signal sequence allowing them to reside mainly in the mitochondrial matrix.

DAP3 or death-associated protein 3 is a highly conserved GTP-binding protein of 40 kDa, encoded by the DAP3 gene located in chromosome 1 q21 (49). It is normally kept inactive as phosphoprotein by the action of protein kinase B (AKT/PKB). When activated, it co-localizes with FADD and participates in the formation of the DISC.

CDC2/CDK1 or Cell Division Cycle 2, also known as CDK1 (Cyclin Dependent Kinase 1, encodes a member of the CDKs family of serine/threonine kinases. The protein is involved in G1/S and G2/M phase transitions of eukaryotic cell cycle through its association with specific mitotic cyclins.

PRL1/PTP4A1 or Phosphatase of Regenerative Liver is a sub-family of the protein tyrosine phosphatases (PTPs) that, in coordination with kinases, precisely controls the levels of intracellular phosphorylation to regulate many physiological processes. This sub-family of tyrosine phosphatases comprises three members (PRL1, 2, 3; gene name PTP4A1, PTP4A2, PTP4A3) having an approximate molecular size of 20 kDa and sharing at least 75% amino acid sequence identity. High expression of PRL members has been reported in several types of human cancers, and correlate with the severity and progression of many tumors.

The NM23 gene maps to chromosome 17q21 and encodes the nucleoside diphosphate kinase (NDP) A, a member of the NDP kinase family. NM23 expression is reduced in metastatic melanoma and breast cancer cell lines. Transfection into cell lines affects invasion, motility, colonization, differentiation and liver metastasis.

While the individual proteins described above are known, the association between BCL10 and any of these factors/proteins and/or association between any of the identified factors with each other is now described herein. As shown herein, BCL10 and the above-described proteins functionally associate with each other and can modulate or regulate activity of BCL10 and its associated proteins.

Embodiments of the invention include, but are not limited to the following:

One aspect of the invention is a method for isolating a protein complex comprising BCL10 and two, three, four, five, six, seven, eight, nine, ten, eleven, or twelve or all of ROS1, LSD1, BTK, KU80. KU70, CUL4A, IMP3, thioredoxin, hTID1, DAP3, CDK1/CDC2. PRL1/PTP4A1 and NM23, said method comprising obtaining a cytosolic extract of a cell expressing BCL10 and at least one of ROS1, LSD1, BTK, KU80, KU70, CUL4A, IMP3, thioredoxin, hTID1, DAP3. CDK1/CDC2, PRL1/PTP4A1 or NM23, contacting components of the cytosolic extract with a ligand for BCL10 under conditions suitable for binding of BCL10 to the ligand and removing components that do not bind to the ligand; and separating the components bound to the BCL10 ligand from the BCL ligand, thereby recovering a protein complex comprising BCL10. In some embodiments of this method, the cell extract is obtained commercially and in others a cytosolic extract may be produced by disrupting a cell, for example, by sonication, homogenization, French pressing, exposure to an enzyme or surfactant, or osmotic shock and then removing solid components, for example, by filtration or centrifugation. In some embodiments, the BCL10 will be wild-type or a wild-isotype. In other embodiments, the BCL10 component may be genetically engineered and have at least 80, 85, 90, 95, 96, 97, 98, 99 or <100% sequence identity to a wild-type BCL10.

The protein complex disclosed herein may comprise BCL10 and ROS1, BCL10 and LSD1. BCL10 and BTK. BCL10 and KU80, BCL10 and KU70, BCL10 and CUL41, BCL10 and IMP3. BCL10 and thioredoxin, BCL10 and hTID1, BCL10 and DAP3, BCL10 and CDK1/CDC2, BCL10 and PRL1/PTP4A1 or BCL10 and NM23. In some embodiments, the complex will contain BCL10 and two, three, four, five, six, seven, eight, nine, ten, eleven, or twelve or all of ROS1, LSD1, BTK, KU80, KU70, CUL4A, IMP3, thioredoxin, hTID1, DAP3, CDK1/CDC2, PRL1/PTP4A1 or NM23. In some embodiments, the BCL10 and ROS1, LSD1, BTK, KU80, KU70, CUL4A, IMP3, thioredoxin, hTID1, DAP3, CDK1/CDC2, PRL1/PTP4A1 or NM23 are produced by a wild-type cell, in others they are produced by a genetically engineered cell, such as a cell that expresses BCL10 (SEQ ID NO: 2) and ROS1 (SEQ ID NO: 4), LSD1 (SEQ ID NO: 6), BTK (SEQ ID NO: 8), KU80 (SEQ ID NO: 10), KU70 (SEQ ID NO: 12), CUL4A (SEQ ID NO: 14), IMP3 (SEQ ID NO: 16), thioredoxin (SEQ ID NO: 18), hTID1 (SEQ ID NO: 20), DAP3 (SEQ ID NO: 22), CDK1/CDC2 (SEQ ID NO; 24), PRL1/PTP4A1 (SEQ ID NO: 26) and/or NM23 (SEQ ID NO; 28). In some embodiments, these proteins have the sequences described by SEQ ID NOS: 2, 4, 6, 8, 10, 12, 14, 16, 18, 20, 22, 24, 26 or 28 and in other embodiments, they may have a sequence that is at least 80, 85, 90, 95, 96, 97, 98, 99 or <100% identical or similar to SEQ ID NOS: 2, 4, 6, 8, 10, 12, 14, 16, 18, 20, 22, 24, 26 and 28.

| Number | Gene Name | Name | Gene ID | RefSeqGene Accession No.s (incorporated by reference) | RefSeq protein Accession No.s (incorporated by reference) | Other Name |
|---|---|---|---|---|---|---|
| 1 | BCL10 | B-cell lymphoma/ leukemia 10 | 8915 | NG_012216.2 | NP_003912.1 (SEQ ID NO: 2); NP_001307644; XP_011540699; XP_011540700; XP_011540701 | CARMEN, CIPER, CLAP, IMD37, c-E10, mE10 |
| 2 | ROS1 | ROS proto-oncogene 1, receptor tyrosine kinase (ROS1) | 6098 | NG_033929.1 | NP_002935.2 (SEQ ID NO: 4); XP_006715611; XP_011534351; XP_011534352; XP_011534353; XP_011534354; XP_011534355; XP_011534356; XP_011534357; XP_011534358; XP_011534359; XP_011534360; XP_016866661; XP_016866662 | ROS; MCF3; c-ros-1 |
| 3 | LSD1 or KDM1A | lysine demethylase | 23028 | NG_047129.1 | NP_055828.2 (SEQ ID NO: 6); NP_001009999; NP_001350583; XP_005245843; XP_006710536; XP_006710537; XP_016856205; XP_016856206 | AOF2; CPRF; KDM1; LSD1; BHC110 |
| 4 | BTK | Bruton tyrosine kinase | 695 | NG_009616.1 | NP_000052.1 (SEQ ID NO: 8); NP_001274273; NP_001274274 | AT; ATK; BPK; XLA; IMD1; AGMX1; IGHD3; PSCTK1 |
| 5 | KU80 or XRCC5 | X-ray repair cross complementing 5 | 7520 | NG_029780.1 | NP_066964.1 (SEQ ID NO: 10) | KU80; KUB2; Ku86; NFIV; KARP1; KARP-1 |
| 6 | KU70 or XRCC5 | X-ray repair cross complementing 6 | 2547 | NC_000022.11 | NP_001460.1 (SEQ ID NO: 12); NP_001275905; NP_001275906; NP_001275907 | ML8; KU70; TLAA; CTC75; CTCBF; G22P1 |
| 7A | CUL4A | cullin 4A cullin-RING-based E3 ubiquitin-protein ligase | 8451 | NC_000013.11 MIM: 603137 | NP_001008895.1 (SEQ ID NO: 14); NP_003580; NP_001265442; NP_001265443; NP_001341867; NP_001341868; NP_001341869; | |

-continued

| Number | Gene Name | Name | Gene ID | RefSeqGene Accession No.s (incorporated by reference) | RefSeq protein Accession No.s (incorporated by reference) | Other Name |
|---|---|---|---|---|---|---|
| 7B | CUL4B | Cullin 4B Ubiquitin Ligase | 8450 | NG_009388.1 | NP_001341870.; NP_001341871; NP_001341872; NP_001341873; XP_011535825 NP_001073341.1 (SEQ ID NO: 30); NP_003579; NP_001317553; NP_001356074 | CUL-4B, MRXHF2, MRXS15, MRXSC, SFM2 |
| 8 | IMP3 | insulin-like growth factor 2 mRNA-binding protein 3 (IGF2BP3) | 55272 and 10643 | MIM: 612980 | NP_060755.1 (SEQ ID NO: 16); NP_006538; XP_006715702; XP_011513391; XP_011513392; XP_011513393; XP_011513394; XP_011513395 | IMP3; BRMS2; MRPS4; IGF2BP3; C15orf12; KOC; KOC1; VICKZ3 |
| 9 | thioredoxin (TXR) | | 7295 | NM_003329 NM_001244938.2 | NP_003320.2 (SEQ ID NO: 18); NP_001231867; | TRX; TRDX; TRX1; TXN |
| 10 | hTID1 or DNAJA3 | human tumorous imaginal disc (hTID1); DnaJ heat shock protein family (Hsp40) member A3 (DNAJA3) | 9093 | NG_029866.1 | NP_001273445.1 (SEQ ID NO: 20); NP_001128582; NP_005138 | TID1; HCA57; hTID-1 |
| 11 | DAP3 | The death-associated protein 3 | 7818 | NC_000001.11 MIM: 602074 | NP_004623.1 (SEQ ID NO: 22); NP_387506; NP_001186778; NP_001186779; NP_001186780; XP_005245537; XP_005245538; XP_016857778; XP_016857779; XP_016857780; XP_01685778; XP_016857782; XP_016857783; XP_016857784; XP_024305465; XP_024305466; XP_024305468 | DAP-3; S29mt; MRPS29; MRP-S29; bMRP-10 |
| 12 | CDC2 or CDK1 | cyclin dependent kinase 1 | 983 | NG_029877.1 | NP_001777.1 (SEQ ID NO: 24); NP_203698; NP_001163877; NP_001163878; NP_001307847; XP_005270360 | CDC2; CDC28A; P34CDC2; CDK1 |
| 13 | PRL1 or PTP4A1 | Phosphatase of Regenerative Liver (PRL1); prenylated protein tyrosine phosphatases 4A1 (PTP4A1) | 7803 | NC_000006.12; MIM: 601585 | XP_016866760.1 (SEQ ID NO: 26); XP_016866759; XP_011534414; XP_011534413; NP_003454 | HH72; PRL1; PRL-1; PTPCAAX1; PTP(CAAX1); PTP4A1 |
| 14 | NM23 or NME | nucleoside diphosphate kinase 1 | 4830 | NG_021169 | NP_000260.1 (SEQ ID NO: 28); NP_937818 | NB; AWD; NBS; GAAD; NDKA; NM23; NDPKA; NDPK-A; NM23-H1; NME |

Advantageously, this method may further comprise fractionating the cytosolic extract on an ion exchange column, collecting a fraction eluted by 200, 250, 300, 350, 400, 450 mM NaCl, preferably about 250-350 mM NaCl, resolving the NaCl eluted fraction(s) using size exclusion chromatography, collecting a fraction(s) having a molecular mass of at least 700, 800, 900, 1,000 or 2,000 kDa, and contacting this at least 700, 800, 900, 1,000 or 2,000 kDa fraction with a substrate bound to a BCL10 ligand, and recovering a fraction that binds to the substrate for example by elution with 600-800 mM NaCl and/or 0.1-0.5 mM glycine at an acid pH, preferably at about a pH of 2 to 2.5. The substrate may be chromatography beads or other substrate suitable for interaction or binding between a BCL10 ligand attached to the substrate, such as a monoclonal antibody that recognizes BCL10, and BCL10 in complex with other proteins. Numerous suitable resins are known including synthetic resins classified as anionic or cationic exchangers and resins classified for size exclusion or gel filtration. An affinity matrix may include any resin or beads used to couple proteins covalently or non-covalently.

In some embodiments, the BCL10 containing protein complex as disclosed herein may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof.

An extract may be made from any cell type in the body (or any type of cultured cell), including those present in epithelial, connective, muscle or nervous system tissues. It may be derived from bone marrow cells, leukocytes, such as T or B cells, or accessory cells such as dendritic cells. It may be derived from cells derived from the various organs in the body including from the brain, spinal cord, heart, lungs, skin, esophagus, stomach, small intestine, large intestine, gall bladder, pancreas, liver, kidneys, bladder, spleen, bone marrow, thyroid gland, parathyroid gland, adrenal gland, uterus, prostate gland, testis or ovaries. It may be derived from normal cells or cells that have been damaged or treated with drugs or from cancerous or malignant cells. It may be produced from normal cells cultured ex vivo or in vitro or from transformed cells grown in vitro. In some embodiments, the cytosolic extract is a HeLa cell extract, such as HeLa S100 extract which is commercially available or a JURKAT cell extract.

In one embodiment of the invention, the method further comprises binding said protein complex to one or more ligands for DAP3, thereby recovering a complex containing both BCL10 and DAP3.

In one embodiment of the invention, the method further comprises binding said protein complex to one or more ligands for CUL4A or CUL4B, thereby recovering a complex containing both BCL10 and CUL4A or CUL4B.

In another embodiment, the method further comprises binding said complex to one or more ligands for least one of ROS1, BTK or CDK1, removing unbound material, thereby recovering a complex comprising BCL10 and at least one of ROS1, BTK and/or CDK1.

In another embodiment, the method further comprises binding said complex to one or more ligands for ROS1, LSD1, BTK, KU80, KU70, CUL4A, IMP3, thioredoxin, hTID1, DAP3, CDK1/CDC2. PRL1/PTP4A1 and NM23, removing unbound material, thereby recovering a complex comprising BCL10 and at least one of LSD1, KU80, KU70, CUL4A, IMP3, thioredoxin, hTID1, PRL1/PTP4A1 and/or NM23.

In other embodiments of this method, the cell used to produce the cytosolic extract is obtained from a subject having above normal blood sugar, diabetes, insulin resistance or who is over-weight, obese, morbidly obese or malignantly obese. Cytosolic extracts may also be obtained or produced from a subject having cancer. In some embodiments, a cytosolic extract may be obtained from blood cells, such as buffy coat cells. In other embodiments, cytosol may be obtained from cells cultured ex vivo or in vitro or from disruption of cells from a biopsy.

Another embodiment of the invention is directed to a protein complex comprising (a) a BCL10 protein comprising the same or substantially the same amino acid sequence as the amino acid sequence represented by SEQ ID NO: 2, a partial peptide thereof, or a variant thereof having at least 80, 85, 90, 95, 96, 97, 98, 99 or <100% sequence identity or similarity to SEQ ID NO: 2 and (b) at least one protein comprising the same or substantially the same amino acid sequence as the amino acid sequence(s) represented by SEQ ID NOs: 4, 6, 8, 10, 12, 14, 16, 18, 20, 22, 24, 26, or 28, a partial peptide thereof, or a variant thereof having at least 80, 85, 90, 95, 96, 97, 98, 99 or <100% sequence identity or similarity to SEQ ID NOS: 4, 6, 8, 10, 12, 14, 16, 18, 20, 22, 24, 26 or 28.

This protein complex may comprise (a) a BCL10 protein having an amino acid sequence that is at least 80, 85, 90, 95, 96, 97, 98, 99 or <100% identical or similar to the amino acid sequence of BCL10 (SEQ ID NO: 2) and (b) a DAP3 protein having an amino acid sequence that is at least 80, 85, 90, 95, 96, 97, 98, 99 or <100% identical or similar to that of DAP3 (SEQ ID NO: 22).

This protein complex may comprise (a) a BCL10 protein having an amino acid sequence that is at least 80, 85, 90, 95, 96, 97, 98, 99 or <100% identical or similar to the amino acid sequence of SEQ ID NO: 2 and (b) a ROS1 (SEQ ID NO: 4), BTK (SEQ ID NO: 8) and/or CDK1 (SEQ ID NO: 24) protein having an amino acid sequence that is at least 80, 85, 90, 95, 96, 97, 98, 99 or <100% identical or similar to that of SEQ ID NO: 4, 8 and/or 24.

This protein complex may comprise (a) a BCL10 protein having an amino acid sequence that is at least 80, 85, 90, 95, 96, 97, 98, 99 or <100% identical or similar to the amino acid sequence of BCL10 (SEQ ID NO: 2) and (b) a CUL4A (SEQ ID NO: 14) or CUL4B (SEQ ID NO: 30) protein having an amino acid sequence that is at least 80, 85, 90, 95, 96, 97, 98, 99 or <100% identical or similar to that of SEQ ID NO: 14 or 30.

Another embodiment of the invention is directed to an antibody or other ligand that binds to at least one of BCL10, ROS1, LSD1, BTK, KU80, KU70, CUL4A, IMP3, thioredoxin, hTID1, DAP3, CDK1/CDC2, PRL1/PTP4A1 and/or NM23 and which promotes the formation of the complex containing BCL10 and ROS1, LSD1, BTK, KU80, KU70, CUL4A, IMP3, thioredoxin, hTID1, DAP3, CDK1/CDC2, PRL1/PTP4A1 and/or NM23 as disclosed herein.

Another embodiment of the invention is directed to an antibody or other ligand that binds to at least one of BCL10, ROS1, LSD1, BTK, KU80, KU70, CUL4A, IMP3, thioredoxin, hTID1, DAP3, CDK1/CDC2, PRL1/PTP4A1 and/or NM23 and which inhibits the dissociation of the complex containing BCL10 and ROS1, LSD1, BTK, KU80, KU70, CUL4A, IMP3, thioredoxin, hTID1, DAP3, CDK1/CDC2, PRL1/PTP4A1 and/or NM23 as disclosed herein.

Another embodiment of the invention is directed to an antibody or other ligand that binds to at least one of BCL10, ROS1, LSD1, BTK, KU80, KU70, CUL4A, IMP3, thioredoxin, hTID1, DAP3, CDK1/CDC2, PRL1/PTP4A1 and/or NM23 and which inhibits the formation of or which promotes the dissociation of the complex containing BCL10 and ROS1, LSD1, BTK. KU80, KU70, CUL4A, IMP3, thioredoxin, hTID1, DAP3. CDK1/CDC2. PRL1/PTP4A1 and/or NM23 as disclosed herein.

Another embodiment of the invention is directed to a pharmaceutical composition or medicament that comprises an agent that modulates the formation of, dissolution of, or activity of, a complex of BCL10 and at least one of BCL10, ROS1, LSD1, BTK, KU80, KU70, CUL4A, IMP3, thioredoxin, hTID1, DAP3, CDK1/CDC2, PRL1/PTP4A1 and/or NM23, and a pharmaceutically acceptable carrier or excipient; wherein said agent is (i) an antibody or other ligand for BCL10, ROS1, LSD1, BTK, KU80. KU70, CUL4A, IMP3, thioredoxin, hTID1, DAP3, CDK1/CDC2, PRL1/PTP4A1 or NM23, or (ii) siRNA or miRNA or other agent that inhibits or enhances the expression of a gene encoding BCL10, BCL10, ROS1, LSD1, BTK, KU80, KU70, CUL4A, IMP3, thioredoxin, hTID1, DAP3, CDK1/CDC2, PRL1/PTP4A1 or NM23.

Another embodiment of the invention is directed to a pharmaceutical composition or medicament that comprises the antibody or other ligand that inhibits formation of, or which promotes the dissociation of, the complex described above in combination with a pharmaceutically acceptable carrier or excipient such as those disclosed elsewhere herein.

Another aspect of the invention is directed to a method for treating a disease associated with or mediated by BCL10, such as diabetes or insulin resistance, by administering the pharmaceutical composition or medicament containing BCL10 and one or more other proteins that complex with BCL10 described above to a subject in need thereof. These proteins may be wild-type or mutated proteins. Alternatively or additionally, this method may employ agents that modulate expression or functionality of BCL10 and the proteins that complex with it, for example, these agents include inhibitory RNA such as miRNA or siRNA, for nucleic acids encoding BCL10 and the proteins complexing with it, chemical inhibitors or promoters that modulate the association (e.g., inhibit, maintain or promote) of BCL10 with one or more of its associated factors disclosed herein, or functionally affect one or more activities of BCL10 or complexes of BCL10 and one or more of its associated factors.

Another aspect of the invention is directed to a method for treating obesity comprising administering a pharmaceutical composition or medicament containing BCL10 and one or more other proteins that complex with BCL10 described above to a subject in need thereof. These proteins may be wild-type or mutated proteins. Alternatively or additionally, this method may employ agents that modulate expression or functionality of BCL10 and the proteins that complex with it, for example, these agents include inhibitory RNA such as miRNA or siRNA, for nucleic acids encoding BCL10 and the proteins complexing with it, chemical inhibitors or promoters that modulate the association (e.g., inhibit, maintain or promote) of BCL10 with one or more of its associated factors disclosed herein, or functionally affect one or more activities of BCL10 or complexes of BCL10 and one or more of its associated factors Another aspect of the invention is directed to a method for treating cancer by administering a pharmaceutical composition or medicament containing BCL10 and one or more other proteins that complex with BCL10 described above to a subject in need thereof. These proteins may be wild-type or mutated proteins. Alternatively or additionally, this method may employ agents that modulate expression or functionality of BCL10 and the proteins that complex with it, for example, these agents include inhibitory RNA such as miRNA or siRNA, for nucleic acids encoding BCL10 and the proteins complexing with it, chemical inhibitors or promoters that modulate the association (e.g., inhibit, maintain or promote) of BCL10 with one or more of its associated factors disclosed herein, or functionally affect one or more activities of BCL10 or complexes of BCL10 and one or more of its associated factors.

Another embodiment of the invention is directed to a method for identifying an agent that that inhibits or promotes the binding of, or which promotes or inhibits the dissociation of, (a) a BCL10 protein comprising the same or substantially the same amino acid sequence as the amino acid sequence represented by SEQ ID NO: 2, a partial peptide thereof, or a variant thereof having at least 80, 85, 90, 95, 96, 97, 98, 99, <100% sequence identity to SEQ ID NO: 2, to (b) a protein comprising the same or substantially the same amino acid sequence as the amino acid sequences represented by SEQ ID NOS: 4, 6, 8, 10, 12, 14, 16, 18, 20, 22, 24, 26, 28, or 30a partial peptide thereof, or a variant thereof having at least 80, 85, 90, 95, 96, 97, 98, 99, <100% sequence identity to 4, 6, 8, 10, 12, 14, 16, 18, 20, 22, 24, 2, 28 or 30, which method comprises: contacting the agent with an isolated protein complex comprising BCL10 and at least one of ROS1, LSD1, BTK, KU80, KU70, CUL4A, IMP3, thioredoxin, hTID1, DAP3, CDK1/CDC2, PRL1/PTP4A1 and/or NM23, partial peptides or variants thereof, and selecting an agent that inhibits or promotes the binding of BCL10 to at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof; or selecting an agent that inhibits or promotes dissociation of binding between BCL10 and at least one of ROS1, LSD1, BTK, KU80, KU70, CUL4A, CUL4B, IMP3, thioredoxin, hTID1, DAP3, CDK1/CDC2, PRL1/PTP4A1 or NM23, or partial peptides or variants thereof.

Variant polypeptides or proteins include proteins that are similar to full-length BCL10 (SEQ ID NO: 2), ROS1 (SEQ ID NO: 4), LSD1 (SEQ ID NO: 6), BTK (SEQ ID NO: 8), KU80 (SEQ ID NO: 10), KU70 (SEQ ID NO: 12), CUL4A (SEQ ID NO: 14), CUL4B (SEQ ID-), IMP3 (SEQ ID NO: 16), thioredoxin (SEQ ID NO: 18), hTID1 (SEQ ID NO: 20), DAP3 (SEQ ID NO: 22), CDK1/CDC2 (SEQ ID NO: 24), PRL1/PTP4A1 (SEQ ID NO: 26) and/or NM23 (SEQ ID NO: 28) or CUL4B (SEQ ID NO: 30), but which may be truncated or modified, for example, by the deletion, insertion or substitution of 1, 2, 3, 4, 5, 6, 7, 8, 9, 10, 15, 20 or more amino acid residues in at least one domain of one of these proteins.

Variants include domains and active fragments of BCL10 or the ROS1, LSD1, BTK, KU80, KU70, CUL4A, CUL4B, IMP3, thioredoxin, hTID1, DAP3, CDK1/CDC2, PRL1/PTP4A1 or NM23, participate in complex formation, are involved in maintaining stability of the complex, or in a functional activity of a BCL10 containing protein complex.

Similarly, polynucleotide variants of the genes encoding BCL10, ROS1, LSD1. BTK, KU80, KU70, CUL4A, IMP3, thioredoxin, hTID1, DAP3, CDK1/CDC2, PRL1/PTP4A1 and/or NM23 or CUL4B as identified herein by their accession numbers may encode the corresponding variant polypeptide and have a deletion, insertion or substitution of 1, 2, 3, 4, 5, 6, 7, 8, 9, 10, 15, 20, 30 or 40 or more nucleotides compared to the reference sequences above.

One embodiment of the invention is directed to a method for identifying an agent that that inhibits or promotes the binding of, or which promotes or inhibits the dissociation of, (a) a BCL10 protein comprising the same or substantially the same amino acid sequence as the amino acid sequence represented by SEQ ID NO: 2, a partial peptide thereof, or a variant thereof having at least 80, 85, 90, 95, 96, 97, 98, 99, <100% sequence identity to SEQ ID NO: 2, to (b) a protein comprising the same or substantially the same amino acid sequence as the amino acid sequences represented by SEQ ID NOS: 4, 6, 8, 10, 12, 14, 16, 18, 20, 22, 24, 26, 28 or 30, a partial peptide thereof, or a variant thereof having at least 80, 85, 90, 95, 96, 97, 98, 99, <100% sequence identity to 4, 6, 8, 10, 12, 14, 16, 18, 20, 22, 24, 26, 28, or 30 which method comprises contacting the agent with a cell that expresses a protein complex of BCL10 and at least one of ROS1, LSD1, BTK, KU80, KU70, CUL4A, IMP3, thioredoxin, hTID1, DAP3, CDK1/CDC2, PRL1/PTP4A1 and/or NM23, partial peptides or variants thereof, and selecting an agent that inhibits or promotes the binding of BCL10 to at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof; or selecting an agent that inhibits or promotes dissociation of binding between BCL10 and at least one of ROS1, LSD1, BTK. KU80, KU70, CUL4A, IMP3, thioredoxin, hTID1, DAP3, CDK1/CDC2, PRL1/PTP4A1 or NM23, or partial peptides or variants thereof.

Another embodiment of the invention is directed to a kit comprising a protein complex comprising BCL10 and at least one of ROS1, LSD1, BTK, KU80, KU70, CUL4A, CUL4B, IMP3, thioredoxin, hTID1, DAP3, CDK1/CDC2, PRL1/PTP4A1 and/or NM23, or a cell expressing this complex for use in identifying an active agent that promotes or inhibits protein complex formation or which promotes or inhibits dissociation of the complex. The kit may further comprise containers for the protein complex or cells or container and/or reagents for contacting the protein complex or cell expressing the protein complex with an agent to be tested. In some embodiments, it may contain materials and reagents useful for binding a complex containing BCL10 or at least one of ROS1, LSD1, BTK. KU80, KU70, CUL4A, CUL4B, IMP3, thioredoxin, hTID1, DAP3, CDK1/CDC2, PRL1/PTP4A1 and/or NM23 to a ligand for BCL10 or these other protein components. The kit may also contain packaging materials or written or electronic instructions for use of the kit for identifying an active agent.

Another embodiment of the invention is directed to a method for a method for detecting pre-apoptotic or apoptotic cells comprising obtaining cytosol from a cell and detecting presence of, or a quantity of, a protein complex comprising BCL10 and at least one of ROS1, LSD1, BTK, KU80, KU70, CUL4A, CUL4B, IMP3, thioredoxin, hTID1, DAP3, CDK1/CDC2, PRL1/PTP4A1 and/or NM23, in the cytosol.

One embodiment of the invention is directed to diagnosing, prognosing or monitoring risk of diabetes or insulin resistance by comparing the expression levels of LSD1, CUL4A, CUL4B, KU70, hTID1, DAP3. NM23, BCL10, NF-κB and MALT1 from lean, nondiabetic subjects with no family history of diabetes, lean nondiabetic subjects with a family history of diabetes, obese, nondiabetic subjects with no family history of diabetes, obese nondiabetic subjects with a family history of diabetes, and subjects with diabetes. Subjects with abnormal expression levels of one or more of these proteins may be treated to normalize levels using the methods described herein.

Another embodiment is directed to method for diagnosing, prognosing or monitoring a subject having or at risk of developing diabetes comprising comparing a level of expression of at least one of ROS1, LSD1, BTK, KU80, KU70, CUL4A, IMP3, thioredoxin, hTID1, DAP3, CDK1/CDC2, PRL1/PTP4A1 and/or NM23 in a subject to one or more corresponding expression levels of a lean, nondiabetic subject with no family history of diabetes and selecting a subject at risk of diabetes when said levels vary by at least 10, 15, 20, 25, 30, 35, 40, 45, 50, 60, 70, 80, 90 or 100%. In another embodiment of this method the comparing comprises comparing the levels of CUL4B, MALT1, NF-κB and/or BCL10, and wherein said selecting comprises a downward variation of at least 10, 15, 20, 25, 30, 35, 40, 45, 50, 60, 70, 80, 90 or 100% in the level of expression of CUL4B, MALT1, NF-κB and/or an upward variation of at least 10, 15, 20, 25, 30, 35, 40, 45, 50, 60, 70, 80, 90 or 100% in the level of expression of BCL10.

In some embodiments of this method, the cytosol will be from a cell expressing a protein comprising at least BCL10 and DAP3, or at least BCL10 and one or more of ROS1, BTK or CDK1.

In other embodiments, the method involves use of cytosol obtained from cancer cells, such as from lymphoma or leukemia cells, hepatocarcinoma cells, or colorectal cells. In other embodiments, the method involves use of cytosol from cells of the nervous system such as neurons or glial cells. This method may be used to diagnose or prognose or predict a risk of a disease, disorders or conditions associated with a BCL10 protein complex as disclosed herein. In some embodiments this method can be used to diagnose, prognosis or predict a risk of developing a disease, disorder or condition for which apoptosis would be indicated (e.g., cancer) or contraindicated (e.g., premature death of normal cells).

This method may be practiced on cells before or after a treatment, such as before and/or after treatment with gene therapy, protein or peptide therapy, synthetic or natural chemical or drug therapy, or physical, thermal or radiological therapy. For examples, the types or levels of BCL10 containing protein complexes or types and levels of other proteins associated with BCL10 in a complex, may be measured before and after a therapy.

Another embodiment of the invention is directed to a method for a method for detecting cells subject to inflammation associated with activation of NF-κB comprising obtaining cytosol from a cell and detecting presence of, or a quantity of, a protein complex comprising BCL10 and at least one of ROS1, LSD1, BTK, KU80, KU70, CUL4A, IMP3, thioredoxin, hTID1, DAP3, CDK1/CDC2, PRL1/PTP4A1 and/or NM23, in the cytosol. In some embodiments of this method, the cytosol will be from a cell expressing a protein comprise comprising at least BCL10 and DAP3, or at least BCL10 and one or more of ROS1, BTK or CDK1. In other embodiments, the method involves use of cytosol obtained from cells at risk of, or that are undergoing, an inflammatory disease, such as inflammatory diseases associated with activation of NF-κB. Such cells include, but are not limited to, cells involved in insulin resistance or diabetes, including pancreatic cells and adipose tissue including white, yellow or brown fat cells. In other embodiments, the cytosol may be obtained from cells associated with atherosclerosis, developmental disorders, autoimmunity, or other immunological disorders such as those involving maturation or activation of lymphocytes and other mononuclear cells, such as mononuclear leukocytes. Such cells include endothelial cells and other cells of the arterial wall, bone marrow cells and leukocytes including T or B lymphocytes and macrophages including monocyte-derived macrophages. This method may be used to diagnose or prognosis disease, disorders or conditions associated with a BCL10 protein complex as disclosed herein. This method may be practiced on cells before or after a treatment, such as before and/or after treatment with gene therapy, protein or peptide therapy, synthetic or natural chemical or drug therapy, or physical, thermal or radiological therapy. For examples, the types or levels of BCL10 containing protein complexes or types and levels of other proteins associated with BCL10 in a complex, may be measured before and after a therapy.

Another embodiment of the invention is directed to a method for treating pre-apoptotic or apoptotic cells comprising administering to a subject in need thereof at least one agent that inhibits or promotes the binding of BCL10 to at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof; or at least one agent that inhibits or promotes dissociation of binding between BCL10 and at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof. Preferably, the agent is targeted to cells expressing a BCL10 containing protein complex as disclosed herein. In some embodiments of this method, cells of the subject will comprise a protein comprise comprising at least BCL10 and DAP3, or at least BCL10 and one or more of ROS1, BTK or CDK1. The cells of the subject may be cancer cells, such as lymphoma or leukemia cells, hepatocarcinoma cells, or colorectal cells. In other embodiments, the cells may be those of the nervous system such as neurons or glial cells or cells which may be subject to neurodegeneration.

In one embodiment, the proapoptotic function of the BCL10 protein complex is mediated by its ability to release cytochrome c from mitochondria. Treatment may comprise administering an inhibitor such as γS-ATP to prevent release of the cytochrome c.

Treatment by this method may be directed to cells affected by an autoimmune disease such as by celiac disease, diabetes mellitus type 1, Graves' disease, inflammatory bowel disease, multiple sclerosis, psoriasis, rheumatoid arthritis, or systemic lupus erythematosus.

In a related embodiment, this method may be practiced by administering a genetic agent, such as miRNA, siRNA or other agents that inhibits or enhance the expression of BCL10 and/or at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof. For example, siRNA targeting DAP3 is used to knock down expression of DAP3 to determine the effects of DAP3 depletion on apoptosis in vivo as shown by FIG. 6; siRNA targeting DAP3 is used to knock down expression of DAP3 to determine the effects of DAP3 depletion on release of cytochrome c in vivo as shown by FIG. 8.

Another embodiment of the invention is directed to a method for treating an inflammatory disease or disease associated with activation of NF-κB comprising administering to a subject in need thereof at least one agent that inhibits or promotes the binding of BCL10 to at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof; or at least one agent that inhibits or promotes dissociation of binding between BCL10 and at least one of ROS1, LSD1, BTK, KU80, KU70, CUL4A, CUL4B, IMP3, thioredoxin, hTID1, DAP3, CDK1/CDC2, PRL1/PTP4A1 or NM23, or partial peptides or variants thereof. Preferably, the agent is targeted to cells expressing a BCL10 containing protein complex as disclosed herein.

In some embodiments of this method, the cells of the subject may comprise a protein complex containing at least BCL10 and DAP3, or at least BCL10 and one or more of ROS1, BTK or CDK1. In other embodiments, the cells of the subject are at risk of, or are undergoing, an inflammatory disease, such as inflammatory diseases associated with activation of NF-κB. Such cells include, but are not limited to, cells involved in insulin resistance or diabetes, including pancreatic cells and fat cells including white, yellow or brown fat cells. In other embodiments, the subject may have atherosclerosis, developmental disorders, autoimmune disease (such as celiac disease, diabetes mellitus type 1. Graves' disease, inflammatory bowel disease, multiple sclerosis, psoriasis, rheumatoid arthritis, or systemic lupus erythematosus), or other immunological disorders such as those involving maturation or activation of lymphocytes and other mononuclear cells, such as mononuclear leukocytes. This method may be directed to treatment of cells comprising a BCL10 protein complex as disclosed herein that are endothelial cells or other cells of the arterial wall, bone marrow cells and leukocytes including T or B lymphocytes and macrophages including monocyte-derived macrophages.

In a related embodiment, this method may be practiced by administering a genetic agent, such as miRNA, siRNA or other agents that inhibits or enhances the expression of BCL10 and/or at least one of ROS1, LSD1. BTK, KU80, KU70, CUL4A, IMP3, thioredoxin, hTID1, DAP3, CDK1/CDC2, PRL1/PTP4A1 or NM23, or partial peptides or variants thereof. In a related embodiment, this method may be practiced by administering a genetic agent, such as miRNA, siRNA or other agents that inhibits or enhance the expression of BCL10 and/or at least one of ROS1, LSD1, BTK, KU80, KU70, CUL4A, IMP3, thioredoxin, hTID1, DAP3, CDK1/CDC2, PRL1/PTP4A1 or NM23, or partial peptides or variants thereof. For example, siRNA targeting DAP3 is used to knock down expression of DAP3 to determine the effects of DAP3 depletion on release of cytochrome c in vivo as shown by FIG. 8; or siRNA targeting DAP3 is used to knock down expression of DAP3 to determine the effects of DAP3 depletion activation of NF-κB in vivo as shown by FIG. 10.

Polynucleotide and polypeptide variants or analogs. A nucleotide sequence encoding BCL10. BIF, or other protein sequence disclosed herein nucleic acid sequence may have 1, 2, 3, 4, 5, 6, 7, 8, 9, 10 or more deletions, insertions or substitutions of a nucleotide or have at least 80, 90, 95, 99 or up to 100% sequence identity with the sequences disclosed herein or known sequences for BCL10, BIFS and other protein disclosed herein. The degree of identity between two nucleic acid sequences can be determined using the BLASTn program for nucleic acid sequences, which is available through the National Center for Biotechnology Information (<hypertext transfer protocol://_www.ncbi.nlm.nih.gov/blast/Blast.cgi?PAGE=Nucleotides>)(last accessed Jul. 31, 2019). The percent identity of two nucleotide sequences may be made using the BLASTn preset "search for short and near exact matches" using a word size of 7 with the filter off, an expect value of 1,000 and match/mismatch of 2/-3, gap costs existence 5, extension 2; or standard nucleotide BLAST using a word size of 11, filter setting "on" (dust) and expect value of 10.

A variant BCL10, BIF, or other polypeptide may have 1, 2, 3, 4, 5, 6, 7, 8, 9, 10 or more deletions, insertions or substitutions of an amino acid residue or have at least 80, 90, 95, 99 or up to 100% sequence identity with a disclosed amino acid sequence. BLASTP may be used to identify an amino acid sequence having at least 70%, 75%, 80%, 85%, 87.5%, 90%, 92.5%, 95%, 97.5%, 98%, 99% sequence similarity to a reference amino acid sequence, such as those described herein using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score.

BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. Default settings for BLASTP are described by and incorporated by reference to ≤blast.ncbi.nlm.nih.gov/Blast.cgi?PROGRAM=blastp& PAGE_TYPE=BlastSearch&LIN K_LOC=blasthome≥ (last accessed Jul. 31, 2019). This disclosure also encompasses degenerate polynucleotide sequences encoding the proteins disclosed herein.

Typically a variant polynucleotide will encode, or a variant polypeptide will have, at least one or substantially all the functional activity of the unmodified parent molecule. In some embodiments, a variant BCL10 or BIF polypeptide will have 10, 20, 30, 40, 50, 60, 70, 80, 90, 100, 150, 200 or >200% of the affinity for forming a protein complex of an unmodified or wild-type parent molecule. In other embodiments, an analog will increase or decrease a functional property of a BCL10-containing protein complex, for example, increase or decrease its ability to induce cytochrome c release from mitochondria, increase or decrease is ability to induce apoptosis, or increase or decrease its ability to activate NF-κB. In some embodiments, a variant BCL10 or BIF polypeptide will decrease or increase these to 10, 20, 30, 40, 50, 60, 70, 80, 90, 100, 150, 200 or >200% of the that of a BCL10-containing complex comprising wild-type BCL10 and BIFS.

In some embodiments, a modified BIF, such as a DAP3 variant, that modulates or modifies the properties of a BCL10 complex containing one or BIFs may replace a wild-type version of BCL10 or one or more BIFs. This replacement can affect complex formation, complex function in apoptosis, complex-triggered activation of NF-kB, cell growth, cell death, cell differentiation, cell transformation, cell maturation, cell migration and invasion, and/or cell metabolism in the body associated with one or more of the BCL10 associated diseases.

Polynucleotides encoding BCL10, BIFS or the other factors and proteins disclosed herein, their fragments or variants may be produced by chemical synthesis, by molecular biological, or by recombinant methods well known in the art. Such polynucleotides may be incorporated into vectors or DNA constructs, transformed into cells, and used to quantitatively or qualitatively modify protein complex formation or expression.

Antibodies or other ligands. Antibodies that bind to BCL10 or ROS1, LSD1. BTK, KU80, KU70, CUL4A, IMP3, thioredoxin, hTID1, DAP3, CDK1/CDC2, PRL1/PTP4A1 and/or NM23 may be monoclonal or polyclonal and be of any isotype, such as IgG, IgM, IgA, IgD and IgE or various subtypes thereof such as IgG1, IgG2, IgG3, IgG4, IgM, IgA1, IgA2, or IgAsec, isotype antibodies. Monoclonal antibodies may also be in the form of IgY or camelid antibodies. This term also includes antigen-binding fragments of antibodies, such as Fab, Fab'2 fragments, single chain antibodies, or polypeptides comprising complementarity determining regions (CDRs) that can bind to BCL10 or other target protein or protein complex.

Such antibodies may bind to the BCL10. BCL10 protein complexes or on proteins they recognize, such as BCL10 or on ROS1, LSD1, BTK, KU80, KU70, CUL4A, IMP3, thioredoxin, hTID1, DAP3, CDK1/CDC2, PRL1/PTP4A1 and/or NM23 proteins with a binding affinity characterized by a Kd of better than 100 nM, better than 10 nM, or better than 1 nM. Many such antibodies are commercially available and such antibodies may be made by techniques well known in the art for producing polyclonal, monoclonal, or recombinant antibodies. Antibodies used to treat humans are preferably human, humanized, or chimeric antibodies comprising human amino acid sequences.

Non-antibody ligands that bind to BCL10, BCL10 protein complexes or ROS1, LSD1, BTK, KU80, KU70, CUL4A. CUL4B, IMP3, thioredoxin, hTID1, DAP3, CDK1/CDC2, PRL1/PTP4A1 and/or NM23 proteins include aptamers, which are oligonucleotide or peptide molecules that bind to a specific target molecule such as BCL10 or the other proteins disclosed herein. Apatmers may be produced to a target protein by methods known in the art, for example, by the procedures described by and incorporated by reference to Mallikaratchy, Prabodhika (Jan. 30, 2017). "Evolution of Complex Target SELEX to Identify Aptamers Against Mammalian Cell-Surface Antigens". *Molecules*. 22 (2): 215. doi:10.3390/molecules22020215. PMC 5572134. PMID 28146093 or to Colas P.; Cohen B.; Jessen T.; Grishina I.; McCoy, J.; Brent, R. (1996). "Genetic selection of peptide aptamers that recognize and inhibit cyclin-dependent kinase 2". Nature. 380 (6574): 548-550. Bibcode: 1996Natur.380. 548C. doi: 10.1038/380548a0. PMID 8606778.

Other ligands include affimers a small, highly stable protein engineered to display peptide loops which provides a high affinity binding surface for a specific target protein. It is a protein of low molecular weight, 12-14 kDa, derived from the cysteine protease inhibitor family of cystatins.

Still other ligands are small organic molecules having molecular weights less than 900 Da which regulate biological processes including disruption of protein-protein interactions such as those involved in maintaining protein complexes comprising BCL10 as disclosed herein. Use of such small molecule ligands is known and incorporated by reference to "Small-molecule inhibitors of protein-protein interactions: progressing towards the dream". Nature Reviews Drug Discovery. 3 (4): 301-17 doi: 10.1038/nrd1343. PMC 4179228. PMID 15060526.

Other modes of modulating interaction or binding of BCL10 with other components of complex include use of miRNA or siRNA to reduce expression of BCL10 or one or more of the other components of the protein complex.

miRNA, SIRNA and other modulators of gene expression. Examples of substances that bind to or degrade BCL10 or other transcripts encoding protein components of the complex include antisense RNA, ribozymes, small interfering RNA (siRNA), and micro RNA (miRNA) against the RPN2 gene, siRNA, miRNA, and the like, which cause RNA interference (RNAi) against a target gene, are preferably used as gene expression inhibitors. RNA interference refers to a phenomenon in which gene expression is suppressed by a double-stranded (ds) RNA molecule in a sequence-specific manner. For example, RNA interference results from target mRNA cleavage by siRNA, gene silencing through heterochromatin formation in a target DNA region by siRNA, and translational and transcriptional repression and mRNA degradation by miRNA. A siRNA sequence can be designed based a target gene or mRNA sequence, such as the BCL10 sequence of SEQ ID NO: 1 or the DAP3 sequence as disclosed by accession number herein and can be artificially synthesized.

Such siRNA can be obtained by any method known in the art. For example, siRNA can be chemically synthesized by the phosphoramidite method, which is also employed for the chemical synthesis of DNA, through the sequential condensation reaction of a single base at a time towards the 5' to 3' end. Preferably, the hydroxyl groups of the 2' ends of individual ribonucleotides are protected to prevent the degradation by RNase during synthesis. Such protecting groups include 2'-O-t-butyldimethylsilyl (2'-tBDMS), 2'-O-(triisopropylsilyloxy)methyl (2'-TOM), and 5'-silyl-2'-acetoxyethoxy (2'-ACE) groups. siRNA against a target gene, such as that for BCL10, has a sequence corresponding to a predetermined sequence of the gene, i.e., a sequence corresponding to a part of a target mRNA sequence.

In the present invention, miRNA can be used in the form of a miRNA precursor or a primary miRNA (pri-miRNA) and it can be synthesized by a chemical method or delivered to cells in the form of a plasmid so as to be expressed. Examples of a method for delivering miRNA to cells include administration of a mixture of miRNA and cationic lipid, delivering miRNA to cells by electrical stimulus, or delivering it by means of a virus, but are not limited thereto.

These methods may be applied to cells ex vivo or in vitro. For example, cells may be removed from a patient, maintained or cultured ex vivo, infused or transformed with miRNA or siRNA targeting mRNA encoding BCL10 or mRNA encoding other proteins in the complex, such as DAP3, and then reinfused or re-implanted into the patient.

A pharmaceutical composition for use in the methods disclosed herein, including for treatment diabetes or cancer, may comprise siRNA or miRNA as an active ingredient may further comprise a pharmaceutically acceptable carrier.

Pharmaceutically acceptable carrier or excipients. As used herein, the term "pharmaceutically acceptable carrier" refers to a carrier or diluent that does not impair the functionality or biological activity and characteristics of an administered compound. Such a carrier is typically sterile and biocompatible with the active ingredient. A pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the agents, including antibodies, ligands, miRNA or siRNA of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets.

A composition as disclosed herein, including one containing a BCL10 containing protein complex or antibodies or ligands that recognize components of this complex, miRNA, siRNA or drugs disclosed herein may be prepared as an oral or parenteral formulation. Pharmaceutical formulations of the present invention include those suitable for oral, rectal, nasal, topical (including buccal and sublingual), subcutaneous, vaginal or parenteral (including intramuscular, subcutaneous and intravenous) administration or a form suitable for administration by inhalation or insufflation. Examples of oral formulations comprising the composition of the present invention as an active ingredient include tablets, troches, lozenges, aqueous or emulsified suspensions, powders, granules, emulsions, hard or soft capsules, syrups, or elixirs. Formulations such as tablets or capsules may include a binder such as lactose, saccharose, sorbitol, mannitol, starch, amylopectin, cellulose or gelatin, an expedient such as dicalcium phosphate, a disintegrant such as corn starch or sweet potato starch, and a lubricant such as magnesium stearate, calcium stearate, sodium stearyl fumarate or polyethylene glycol wax. Capsule formulations may comprise, in addition to the above-mentioned substances, a liquid carrier such as fatty oil.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas, e.g. containing conventional suppository bases such as cocoa buffer or other glycerides. For spray formulations, such as aerosols, a propellant for spraying a water-dispersed concentrate or wet powder may be used in combination with an additive.

Obviously, numerous modifications and variations of the present invention are possible in light of the above teachings. It is therefore to be understood that within the scope of the appended claims, the invention may be practiced otherwise than as specifically described herein.

Example 1

Isolation and Purification of a Mega Protein Complex from an S100 Extract of HeLa Cancer Cells and Characterization of the Mechanisms by which this BCL10-Containing Complex Induces Apoptosis and Activation of NF-κB Cell Culture. Hela and Jurkat cell lines were purchased from ATCC (Manassas, VA, USA) and maintained in DMEM and RBMI 1640 growth media, respectively as recommended by the guideline of the supplier. The growth medium was supplemented with appropriate heat-inactivated fetal calf serum, antibiotics (penicillin, streptomycin) and atmosphere (95% air and 5% $CO_2$) as recommended by ATCC; see American Type Culture Collection (2011). Animal Cell Culture Basics: Tips and Techniques for Continuous Cell Lines (incorporated by reference).

Constructs. The Flag-tagged full length BCL10, amino terminal CARD domain (aa 1-97) and the c-terminus serine-threonine rich region (aa 104-233) cloned in mammalian expression pFLAG CMV-2 or in pCDNA3 and LacZ reporter vectors were provided by Dr. E. S Alnemri; Srinivasula S M, Ahmad M, Lin J H, Poyet J L, Femandes-Alnemri T, Tsichlis P N Alnemri E S (1999). CLAP, a novel caspase recruitment domain-containing protein in the tumor necrosis factor receptor pathway, regulates NF-kappaB activation and apoptosis. *J. Biol. Chem.*, 274; 17946-17954. NF-κB luciferase reporter construct (5×κB-luciferase reporter plasmid obtained from Stressgen Biotechnologies Corp., San Diego, CL, USA). DAP3 gene was amplified from a cDNA library extracted from HEK-293T cells and inserted into a pCMV-tag-5A vector (Addgene, Watertown, MA, USA) to fuse with a Myc tag at the C terminus of DAP-3 (pCMV-myc-DAP-3).

Transient transfection. pFLAG CDNA3-BCL10 and pCMV-myc-DAP3 were transfected separately or together into Hela cells using Oligofectamine™ (Invitrogen). Similarly, either or both genes were also transfected with the luciferase reporter into HeLa or Jurkat cells for assessment of their effect on activation of NF-κB as previously described; Srinivasula S M, Ahmad M, Lin J H, Poyet J L, Femandes-Alnemri T, Tsichlis P N Alnemri E S (1999). CLAP, a novel caspase recruitment domain-containing protein in the tumor necrosis factor receptor pathway, regulates NF-κB activation and apoptosis. *J. Biol. Chem.*, 274; 17946-17954. siRNA Transfection. HeLa cells, at 70-80% confluence, were washed by 1×PBS and transfected with the indicated plasmids according to the manufacturer's instructions. The transfection of siRNA into HeLa cells was performed using Oligofectamine™ (Invitrogen) or RNAimax (Invitrogen) according to the manufacturer's protocols. Oligonucleotides for siRNA were synthesized by Invitrogen and the sequences were as the following: DAP3 siRNA, 5'-AGGCUUCAACCUGGCUGAAGAAUUU-3' (SEQ ID NO: 31), and the control siRNA sequence was: 5'-UU-CUCCGAACGUGUCACGUTT-3' (SEQ ID NO: 32). To insure the knockdown of full-length gene expression, the silencing of DAP3 was confirmed by Western blotting with anti-DAP3 antibody using the lysates extracted from treated HeLa cells. 100 pmol of DAP3-siRNA or the control were used for every $2 \times 10^6$. Subsequently. FLAG-BCL10 construct was introduced and cells were incubated for another 24-48 hr before analysis.

Assay of NF-κB Activation. NF-κB activation was performed using a luciferase reporter gene. HeLa or Jurkat cells were transfected with 5×κB-luciferase reporter plasmid and various expression plasmids or the different siRNA. 24 to 72 h after transfection, cells were harvested and subjected to luciferase assay as previously described by Srinivasula S M, et al., (1999), *J. Biol. Chem.*, 274; 17946-17954 (incorporated by reference). In certain experiments. to normalize for transfection efficiency, all transfections included a LacZ-expressing plasmid, and the lysates were assayed for β-galactosidase activity. Data represent the average of at least three independent experiments f SD.

Apoptosis Assay. Apoptosis was measured after 48-72 h in the various transfected cells using the Muse™ Annexin-V & Dead Cell Assay kit (EMD Millipore Bioscience, Darmstadt, Germany) according to the manufacturer's protocol. The kit utilizes a fluorescent dye (FITC) conjugated to annexin-V to detect phosphatidylserine (PS) on the external membrane of apoptotic cells and 7-AAD (7-aminoactinomycin D) as dead cells marker. 7-AAD is excluded from living healthy cells, as well as early apoptotic cells. Percentages of cells in early (annexin-V+ve/7-AAD−ve) and late stages of apoptosis (annexin-V+ve/7-AAD+ve) were determined by a flow cytometer-based instrument (Muse™ Cell Analyzer) according to the manufacturer protocols. Data represent the mean f SD of at least three individual experiments.

Preparation of S100 Extract. $2 \times 10^8$ of HeLa cells were harvested and washed twice with phosphate-buffered saline (PBS), and cell fractionation was performed as previously described by Saleh et. al. in 1999 [58]; Saleh A. Srinivasula S M, Acharya S. Fishel R, Alnemri E S (1999). Cytochrome C and dATP-mediated oligomerization of Apaf-1 is a prerequisite for procaspase-9 activation. *J. Biol. Chem.*, 274; 17941-17945. In brief, after washing the cells with PBS, the pellet was suspended in 5 ml of ice-cold buffer A [20 mM HEPES pH 7.5, 100 mM NaCl, 10 mM KCl, 1.5 mM $MgCl_2$, 10% glycerol, 0.1 mM DTT, 1.0 mM phenylmethylsulfonyl fluoride, and 1.0 µg/mL each of aprotinin, pepstatin and leupeptin. The cells were then homogenized by bouncing ten times in a Dounce homogenizer with a sandpaper-polished pestle. After centrifugation for 10 min (24,000 g) at 4° C., the supernatants were collected and pooled. Protamine sulfate was added to a final concentration of 0.2% to the supernatant to precipitate nucleic acids. The extract was cleared by centrifugation at 27,000×g for 15 min at 4° C. the supernatant was then centrifuged at 105.000 g for 30 min at 4° C. The resulting supernatant was used as the soluble S100 extract.

Purification of BCL10 interacting proteins. All the purification steps were carried out at 4° C. An S-100 HeLa cells extract was prepared from a 3-liter adherent cells (grown in 50× T175 culture flasks) in 20 mM HEPES buffer (pH 7.5) containing 100 mM NaCl, 10 mM KCl, 1.5 mM $MgCl_2$, 10% glycerol, 0.1 mM DTT, 1 mM phenylmethylsulfonyl fluoride, 1.0 µg/mL pepstatin, and 1 µg/ml leupeptin. 600 mg of total proteins were loaded onto an ion exchange column of DEAE (HiPrep DEAE FF 16/10, 20 mL bed volume, GE Healthcare Life Sciences Massachusetts, USA). After washing the column with 10-times the column volumes of the extraction buffer, proteins were eluted by a 400 mL continuous gradient of NaCl (100 mM-600 mM NaCl, at a flow rate of 0.5 ml/min (4.0 mL/fraction). The fractions containing BCL10 (~250 mM to −350 mM NaCl) were pooled and concentrated using Centricon-10 (Amicon, Merck-Millipore, Germany), and the final concentration of NaCl was adjusted to 100 mM in a final volume of 5.0 mL. Subsequently, the concentrated fractions containing BCL10 (47 mg) were loaded on a Sephacryl S 300 column (HiPrep 16/60 Sephacryl S 300 HR column, 16 mm×600 mm, GE Healthcare Life Sciences, Massachusetts, USA). BCL10 containing fractions >800 kDa were pooled, concentrated to 5.0 mL using the same HEPES buffer (6.7 mg protein), and loaded onto a 3.0 ml column of AffiGel 10 (BioRad) bound human serum albumin to remove non-specific binding to the matrix (HSA Column). The unbound protein eluted from the HSA column was then loaded onto 1 ml column AffiGel 10-bound recombinant BCL10 (200 µg, BCL10 Column) to trap its interacting factors (BIFs), at a flow rate of 0.1 mL/min. Coupling of HSA (1.5 mg) and recombinant BCL10 (200 µg) to the AffiGel 10 matrix was performed according the manufacturer's protocol. The factors bound to both the HSA and BCL10 columns were eluted separately with 20 mM HEPES buffer (pH 7.5) containing 700 mM NaCl (1.5 volume of the column), followed by 200 mM glycine (pH 2.2, one volume of the column). The eluted proteins from each column were dialyzed (using SnakeSkin Dialysis Tubing (ThermoFisher Scientific, Massachusetts, USA) against a buffer containing 20 mM HEPES pH 7.5, 50 mM NaCl, 10 mM KCl, 1.5 mM MgCl2, 10% glycerol and 0.1 mM DTT] and concentrated to a 1.0 mL using Centricon-10. The final protein concentration from the BCL10 affinity column was 117 µg/mL and 379 µg/mL from the HSA column as determined by using the BCA Assay (Pierce Chemical, IL, USA). The samples were aliquoted into six cryogenic tubes and frozen at −80° C. until subsequent analysis. The comparison between the eluted proteins from both columns is visualized by Coomassie staining as shown in FIG. 2B. two tubes of each sample were sent for mass spectrometry analysis to identify the proteins.

Identification the Components of BCL10 Complex by Tandem Mass Spectrometry. The identity of the BCL10 associated factors (BIFs) was analyzed according to the detailed procedure described in Saleh A. Schieltz D, Ting N, McMahon S B, Litchfield D W, Yates III J R, Lees-Miller S P, Cole M D, Brandl C J (1998). Tra1p is a component of the yeast Ada/spt transcriptional regulatory complexes. *J. Biol. Chem.*, 273; 26559-26565 (incorporated by reference). In brief, protein eluted from the HSA and BCL10 columns was digested separately by trypsin. Protein was identified by micro-column high performance liquid chromatography coupled to electrospray ionization tandem mass spectrometry and data base searching. A 100- by 200-μm fused silica capillary (Polymetrics, Inc.) was packed to a length of ~15 cm with 10 mm POROS 10 R2 reverse phase material (PerSpective Biosystems Inc., Framingham, MA, USA). The fritted end of the column was inserted into the needle of the electrospray ion source and sample loaded by helium pressurization in a stainless-steel pump. Chromatography was performed with a dual syringe pump (Applied Biosystems/Thermo Fisher Scientific Corp., Waltham, MA, USA). The mobile phase consisted of 0.5% acetic acid (solvent A) and 80:20 acetonitrile/water containing 0.5% acetic acid (solvent B). A 100:1 precolumn split is used to deliver a flow rate of 1 to 1.5 ml/min. The high-performance liquid chromatography pump is programmed to ramp solvent B from 0 to 60% in 30 min. Electrospray ionization was carried out at voltage of 4.6 kV. Tandem mass spectra were acquired automatically during the entire gradient run. Tandem mass spectra were searched against the human data base (Human Genome Data base) using the SEQUEST program. Parameters for the SEQUEST program were set to locate potential sites of phosphorylation at serine, threonine, and tyrosine residues. Every sequence with high scores that matched a tandem mass spectrum is manually verified. The common proteins eluted from the BCL10 affinity and HSA column were not considered.

Immunoprecipitation Assays. Anti-Flag and anti-Myc antibodies were covalently bound to an Affi-gel matrix according to the manufacture protocols (BioRad Inc., USA), and previously described by Saleh A. Srinivasula S M, Balkir L. Robbins P D, Alnemri E S. (2000). Negative regulation of the Apaf-1 apoptosome by Hsp70. *Nat. Cell Biol.*, 2; 476-83 at a concentration of 1 mg/mL. 50 μL of the antibody-bound beads were incubated with cell extract (200 μg) in a lysis buffer for 4 h at 4° C. under rotation. Subsequently, the beads were washed 4 times with a lysis buffer containing 200 mM NaCl. Proteins were eluted from the beads by 50 μL of the lysis buffer containing 700 mM NaCl and incubation at 37° C. for 15 min. eluted proteins were diluted to adjust the salt concentration to 150 mM, then concentrated to 50 μL using Microcon-10 kDa Centrifugal Filter Unit (Merck-Millipor Co., Germany).

Isolation of rat mitochondria and assay for cytochrome c release. Rat liver mitochondria were prepared as described previously with minor modifications; see Kim T H, Zhao Y, Barber M J, Kuharsky D K, Yin, X M. (2000). Bid-induced cytochrome c release is mediated by a pathway independent of mitochondrial permeability transition pore and Bax. *J. Biol. Chem.*, 275; 39474-3948. Briefly, rat liver was homogenized using a Dounce homogenizer in a 5.0 mM HEPES buffer, pH 7.2, containing 250 mM mannitol, 70 mM sucrose. 0.5 mM EGTA and 0.1 mM PMSF. The intact cells and nuclei were removed from the homogenate by centrifugation at 1,000×g for 10 min at 4° C. Then, the supernatant was further centrifuged at 10,000×g for 10 min at 4° C. the precipitated mitochondria were resuspended in a 10 mM HEPES buffer (pH 7.5) containing 250 mM sucrose, 2 mM $KH_2PO_4$, 5 mM sodium succinate, 25 μM EGTA, and 0.1 mM PMSF. Mitochondria were kept on ice and used within 2 h of preparation. 25 μg of mitochondria (0.5 mg/ml) were incubated at 30° C. in 40 μL of the later buffer for containing the various reagents as indicated in the figure legends with various reagents as indicated in the figure legends. After incubation for 1 hr, the mitochondria were separated from the supernatants by centrifugation at 10,000×g for 10 min at 4° C. Both the supernatant and the pelleted mitochondria were resolved on a 15% SDS-PAGE followed by Western blotting with a rabbit monoclonal anti-cytochrome c-antibody (Abcam, ab133504).

Western Blot Analysis. For Western analysis, total cell lysates were prepared in a lysis buffer containing a mixture of protease and phosphatase inhibitors. Protein quantitation was performed by the BCA method (Pierce Chemical). 35 μg of cell lysate were separated by SDS-PAGE followed by a transfer to PVDF membranes. Probing with monoclonal and polyclonal antibodies of the different proteins was performed according to manufacturer protocols and previously described by Saleh A M, El-Abadelah M M, Aziz M A, Taha M O, Nasr A, Rizvi S A. (2015). Antiproliferative activity of the isoindigo 5'-Br in HL-60 cells is mediated by apoptosis, dysregulation of mitochondrial functions and arresting cell cycle at G0/G1 phase. *Cancer Lett.*, 361; 251-261 and Saleh A M, Taha M O, Aziz M A, Al-Qudah M A, AbuTayeh R F, Rizvi S A. (2016). Novel anticancer compound [trifluoromethyl-substituted pyrazole N-nucleoside] inhibits FLT3 activity to induce differentiation in acute myeloid leukemia cells. *Cancer Lett.*, 375; 199-208 (incorporated herein by reference). Immunoreactive bands were compared to β-actin or α-Tubulin as a loading control. The following primary antibodies were obtained from Cell Signaling Technology (Danvers, MA, USA); anti-CUL4A (rabbit polyclonal, #2699), anti-DAP3 (rabbit polyclonal, #2172), anti-KU70 (rabbit monoclonal, D10A7), anti-KU80 (mouse monoclonal, LS-B11679), anti-hTID1 (mouse monoclonal, #4775) and anti-IMAP3 (mouse monoclonal. #14108). Anti-ROS1 (mouse monoclonal, ab108492) anti-PRL-1 (mouse polyclonal, ab168643) and anti-Myc-tag (mouse monoclonal, Myc.A7, ab18185) antibodies were purchased from Abcam Company (Cambridge, UK). Monoclonal antibodies against LSD1 (sc-271720), BTK (sc-81159), Thioredoxin (sc-271281), CDK1 (sc-517026), NM23 (sc-514515), β-Actin, (sc-376421) and α-Tubulin (sc-58667) were supplied by Santa Cruz Biotechnology. Inc. (Dallas, Texas, USA). Mouse monoclonal anti-FLAG®-M2 antibody was purchased from Sigma-Aldrich Company (Taufkirchen, Germany).

Figure 1B:
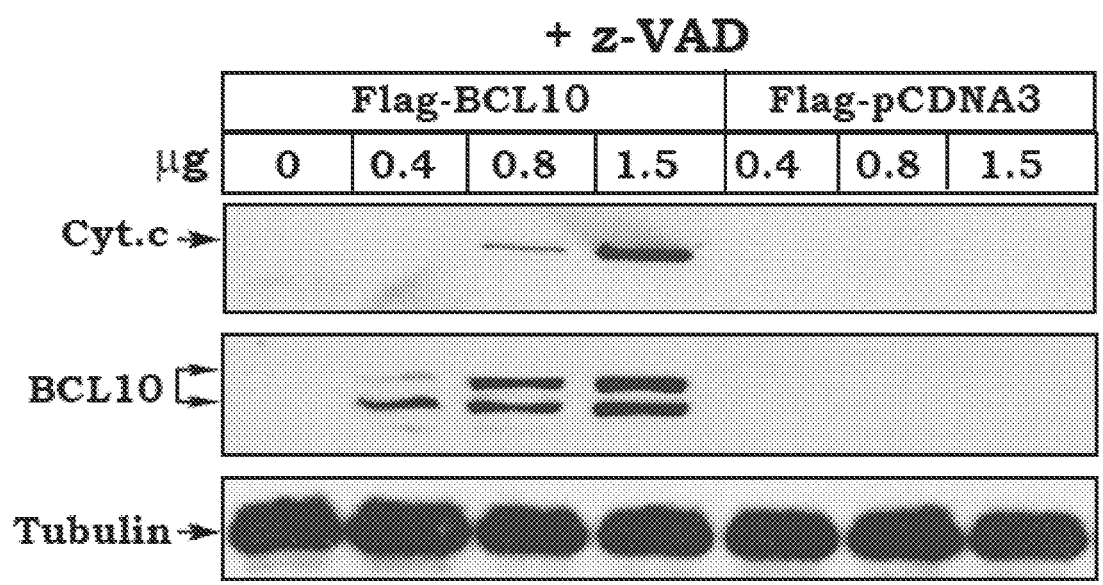

It was found that BCL10 as part of a protein complex induces apoptosis by targeting release of cytochrome c from mitochondria. Overexpression of BCL10 in Hela, 293, or MCF7 cells stimulated the release of cytochrome c from mitochondria as shown by FIGS. 1A and 1B.

HeLa cells were transfected with different amounts of Flag-BCL10 or with a control plasmid in the absence (FIG. 1A) and presence (FIG. 1B) of 50 mM z-VAD-fmk. After 24 hr, cells were harvested and mitochondria-free cytosolic extracts prepared as described in Slordahl T S, Abdollahi P, Vandsemb E N, Rampa C. Misund K et al. (2016). The phosphatase of regenerating liver-3 (PRL-3) is important for IL-6-mediated survival of myeloma cells, *Oncotarget.* 7; 27295-27306 and in Qu S, Liu B, Guo X. Shi H, Zhou M. et al. (2014). Independent oncogenic and therapeutic significance of phosphatase PRL-3 in FLT3-ITD negative acute myeloid leukemia. Cancer. 120; 2130-2141 (both incorporated by reference).

Figure 1C:
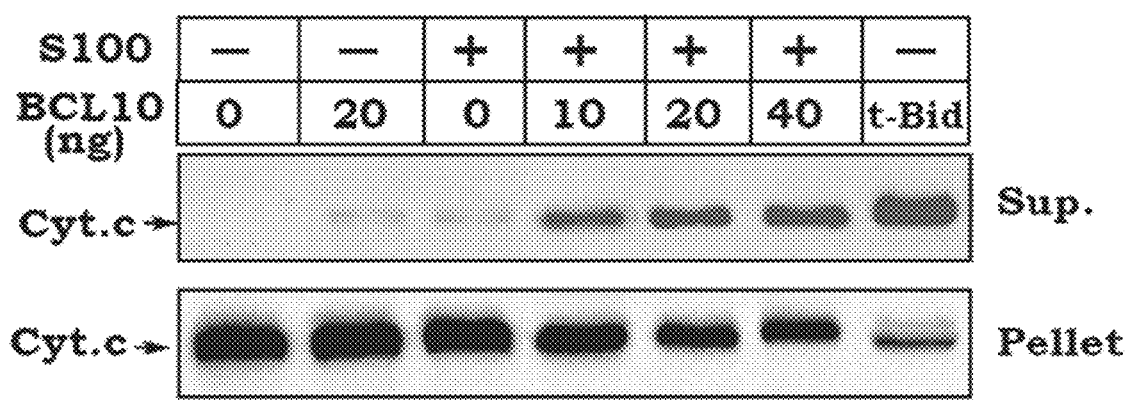

A sample of 100 μg from each of the cytoplasmic extract were fractionated on a 12% SDS gel and immunoblotted with anti cyt.c, anti-Flag, and anti-tubulin antibodies, respectively from top to the bottom. The two immunoreactive bands of Flag-BCL10 represent phosphorylated variants of the protein. As shown by FIG. 1C, mitochondria were purified from a rat liver as described in Chong P S, Zhou J. Cheong L L, Liu S C, Qian J et al. (2014). *Cancer res.* 74; 3043-3053 (incorporated by reference). Mitochondria (200

μg protein) were incubated with different amount of purified recombinant BCL10 in the presence or absence of HeLa cytosolic extracts (S100; 70 μg protein). After 1 hr incubation, mitochondria were removed by centrifugation from the reaction mixtures (pellet) and the presence of cyt.c to the reaction supernatant (sup.) and pellet was assayed by probing with an anti-cyt.c antibody. Release of cyt.c by a human recombinant truncated Bid (t-Bid. 10 ng) was used as a positive control.

The ability of BCL10 to release cytochrome c appears to be independent from caspase action, since the presence of the general caspase inhibitor z-VAD-fmk did not inhibit signaling of cytochrome c release by BCL10 (FIG. 1B). The ability of recombinant BCL10 to release cytochrome c from isolated rat mitochondria was dependent on addition of the cytosolic extracts (S100) to the reaction, indicating that the proapoptotic function of BCL10 requires additional unidentified cytosolic factor(s) (FIG. 1C). Interestingly, immunodepletion of two proapoptotic members of the BCL2 family, BID and BAX [2], from the S100 extracts did not abolish the ability of recombinant BCL10 to stimulate release cytochrome c from mitochondria. These observations are consistent with existence of a novel proapoptotic complex containing BCL10 which functions by targeting the release of mitochondrial cytochrome c.

Figure 2A:
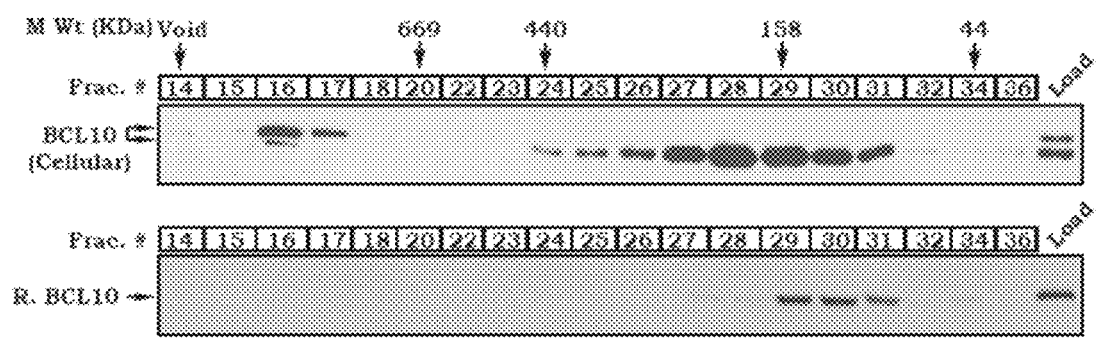
FIG. 2A. Western blots of FPLC fractionated HeLa cell extract probed with monoclonal antibody to BCL 10.
Figure 2B:
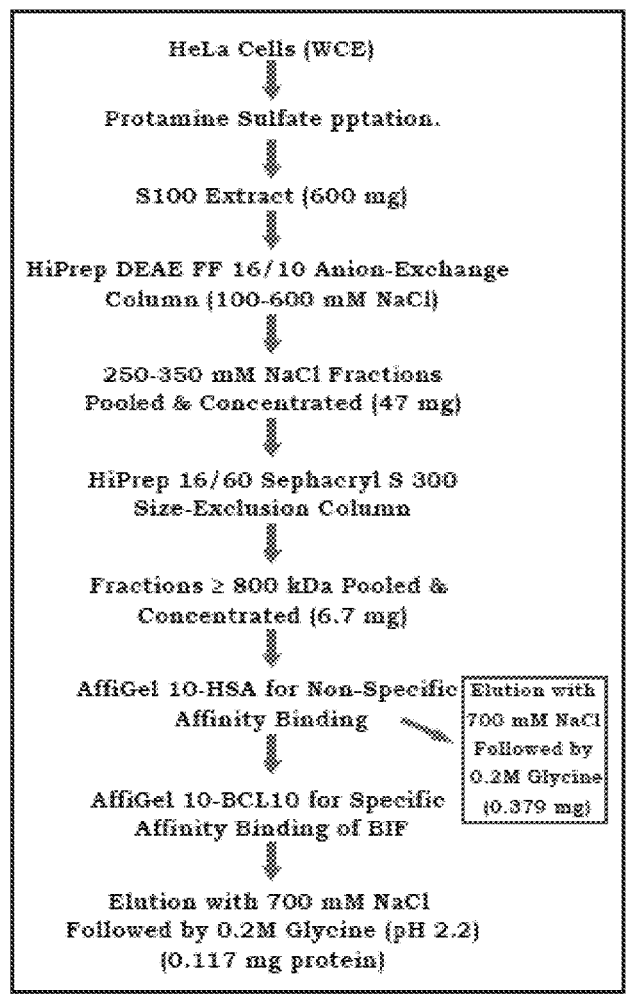
FIG. 2B. Schematic diagram showing the purification steps for the BCL10 complex from HeLa cells.

Biochemical fractionation of BCL10 from Hela S100 extracts on a sizing column revealed that 10-20% of the total BCL10 exists in a large mega complex (FIG. 2A, top), unlike the recombinant protein after fractionation on the same size exclusion column shown at FIG. 2A, bottom. FIG. 2A depicts the results of purification of the high molecular weight BCL10 mega complex (≥1 million daltons). 20 mg of HeLa S100 extract were fractionated on an FPLC column of Superose 12 (upper panel). Equal amounts of the 0.5 ml fractions were Western blotted with a monoclonal antibody to BCL10. Purified recombinant BCL10 (35 μg) was fractionated on the same column under similar conditions is shown in the lower panel. The elution of molecular weight markers is shown by the arrow heads.

FIG. 2B provides a schematic diagram detailing the purification steps for the BCL10 complex from HeLa cells. 600 mg of HeLa S100 extract was loaded onto an ion-exchange column of DEAE, Proteins were eluted from the column by a continuous gradient of NaCl as indicated in the diagram. Then, fractions containing BCL10 were pooled, concentrated and loaded on a Sephacryl S 300 column. The fractions (≥800 kDa) of BCL10 were then loaded onto a 3 ml column of AffiGel bound human serum albumin (HSA) to remove non-specific binding to the matrix. The sample was then loaded onto 1 ml column of affiGel-bound recombinant BCL10 (BCL10) to trap its interacting factors (BIFs).

The purified BCL10 interacting factors (BIFs) from the last step of BCL10 affinity column and the non-specific HSA control column were fractionated by SDS-PAGE and stained with Coomassie Brilliant Blue as shown in FIG. 2C. The gel was able to resolve at least 14 polypeptide bands in the elutions of the BCL10 affinity column that did not exist in the HSA non-specific affinity column. These bands have molecular weights ranging from ~250 kDa to ~15 kDa (FIG. 2C).

Tandem mass-spectrometry identified thirteen components of the novel BCL10-containing protein complex besides BCL10, namely, ROS1, LSD1, BTK, KU80, KU70, CUL4A. IMP3, thioredoxin, hTID1, DAP3, CDK1/CDC2, PRL1/PTP4A1 and NM23. The identities of proteins which associated with the BCL10 affinity column and the non-specific HSA column was determined by tandem mass-spectrometry analysis as described in detail above. The mass-spectrometry data showed that at least thirteen proteins were present in the eluent from BCL10 affinity column but not in the eluent from the nonspecific HSA control affinity column. These proteins are arranged according to their molecular mass: 1) Orphan receptor tyrosine kinase related to anaplastic lymphoma kinase (ROS1) [Mass: 263,958 Da.], 2) FAD-dependent amine oxidase homolog KIAA0601 (LSD1) histone demethylase [Mass:96760 Da.], 3) DNA binding proteins Ku80 [Mass: 82705 Da.], 4) Bruton's tyrosine kinase BTK [Mass: 76150 Da.], 5) Ubiquitin ligase CUL4A [Mass: 76821 Da.], 6) DNA binding proteins Ku70 [Mass: 69712 Da.], 7) Insulin-like growth factor II (IGF-II) messenger RNA (mRNA)-binding protein-3 (IMP3) [Mass: 63705], 8) Oxidoreductase enzyme Thioredoxin [Mass: 54615 Da.], 9) Human tumorous imaginal disc 1 (hTid-1) [Mass: 52489 Da.], 10) Death-associated protein 3 (DAP3) [Mass: 45566 Da.], 11) Cyclin dependent kinase-1 (CDK1, also known as CDC2) [Mass: 27503 Da.], 12) Phosphatase of Regenerative Liver (PRL1/protein tyrosine phosphatase PTP4A1) [Mass: 17670 Da.], 13) Nucleoside diphosphate kinase A (nm23) [Mass: 17298 Da.].

The molecular masses of these factors are in approximate agreement with the demonstrated molecular weights of the BIFs shown in FIG. 2C. In addition, the presence of these factors in the BCL10 purified complex (except for PRL1/PTP4A1 and ROS1) was confirmed by Western blotting with their specific primary antibodies which were absent in the control HSA sample (not shown). None of these factors have been previously reported to interact with BCL10, nor has a BCL10-containing protein complex containing these factors been previously identified.

The identification of this BCL10-containing protein complex and its protein components permits targeting of the functional associations between BCL10 and the other protein components to treat diseases associated with malfunction of BCL10, including but not limited to treatment of different types of cancer or other diseases involving apoptosis, disorders of differentiation and maturation of T and B lymphocytes, disorders of innate or adaptive immunity, autoimmune diseases, microbial infections, inflammatory diseases or disorders, diabetes, insulin resistance, obesity and neurodegenerative diseases or disorders. The identification of the BCL10-containing protein complex also provides new ways to diagnose, prognosis or monitor these diseases or disorders.

Figure 3:
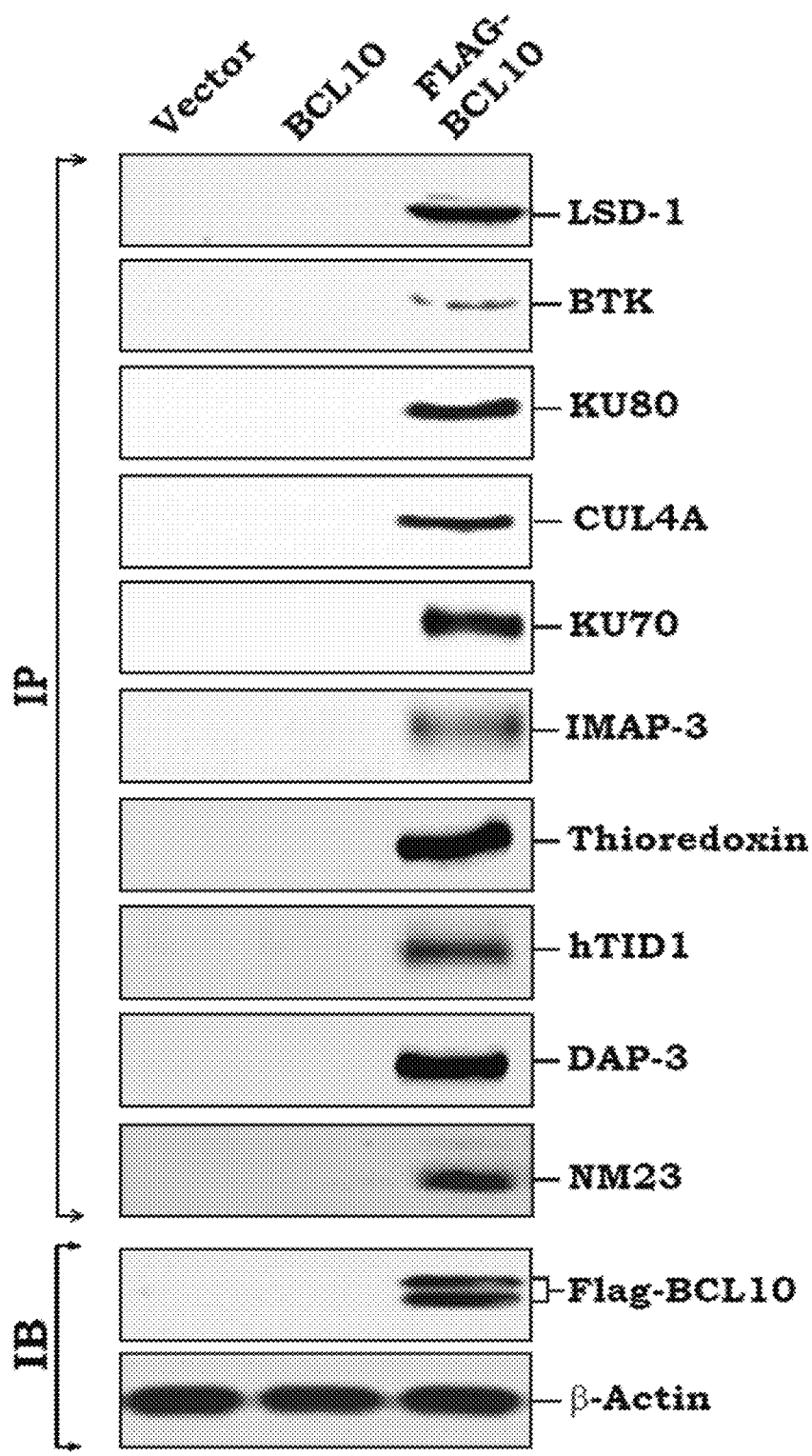
FIG. 3. Ten proteins of the immunoprecipitated HeLa protein complex confirmed to associate with BCL10 in vivo. The extracts were also probed with anti-Flag antibody to show expression of BCL10 and anti-β-actin (IB) to confirm equal amounts of proteins were used for each of the immunoprecipitation sample.

To show the association between BCL10 and the above proteins, empty vector, untagged BCL10 or Flag-tagged BCL10 were transfected into HeLa cells. Ten proteins of the purified complex are confirmed in vivo to associate with BCL10 in HeLa cells by co-immunoprecipitation. Hela cells were transfected with equal amounts (1.3 μg) of pCDNA3 vector, pCDNA3-BCL10 (untagged) and Flag-tagged construct of BCL10. After 72 h of incubation, cultured cells were harvested, lysed and equal amounts of the lysates (200 μg) were incubated with an AffiGel-bound anti-Flag antibody for 4 h at 4° C. after eluting the antibody bound proteins (IP), they were electrophoresed and transferred into a PVDF membrane. The presence of the respective proteins (or BCL10 interactive factors, BIFs) indicated in each blot were shown by immunoblotting using their specific antibodies. The extracts were also probed with anti-Flag antibody to show expression of BCL10 and anti-β-actin (IB) to confirm equal amounts of proteins were used for each of the immunoprecipitation sample. As shown in FIG. 3, ten proteins were detected in the eluted sample containing the Flag-tagged BCL10. These are; LSD1, BTK, KU80, CUL4A, KU70, IMAP3, Thioredoxin, hTID1, DAP3 and NM23. ROS1, CDK1/CDC2 or PRL1/PTP4A1 were not detected, suggesting their potential weak/transient or inducible association with BCL10. The specificity of the association between BCL10 and the ten factors was confirmed by their absence from the elutes of affi-gel-bound anti-Flag antibody which were incubated with protein extracts from cells transfected with either empty or untagged BCL10 vectors.

The mass-spectrometry analysis of the purified complex shown in FIG. 2, identified three protein kinases (the purified complex from the BCL10-affinity column) that were not found in the control eluent from the HSA-AffiGel column; the orphan receptor tyrosine kinase related to anaplastic lymphoma kinase (ROS1), the Bruton's tyrosine kinase BTK and the serine/threonine cyclin dependent kinase-1 (CDK1/CDC2).

To investigate the possible existence of an endogenous kinase activity within the complex that is capable of phosphorylating BCL10 and/or other BIFs, the eluted proteins from both the BCL10 and HSA affinity columns were incubated with or without recombinant BCL10 protein in the presence of radiolabeled ATP. The phosphorylation of the proteins was detected by autoradiography after resolving the samples on a 13% SDS polyacrylamide gel. Briefly, purified recombinant BCL10 (R. BCL10, 50 ng) was incubated with rat mitochondria in mixtures containing or not containing the eluted proteins from the BCL10 affinity column in the presence or absence of ATP and/or its non-hydrolysable analogue (γS-ATP). The release of cytochrome c was assayed as described for FIG. 1C. Lane 7, BCL10 was incubated with purified mitochondria in the absence of recombinant BCL10 and ATP. Lane 8, recombinant t-Bid (25 ng) was incubated with the purified mitochondria. Lane 9, purified mitochondria incubated with only the reaction buffer and ATP. (B) Eluted proteins from the BCL10 affinity column or the HSA control column were incubated with or without BCL10 and radiolabeled ATP for 20 min. followed by electrophoresis on a 13% denaturing polyacrylamide gel. Bands were visualized by autoradiography.

Figure 4A:
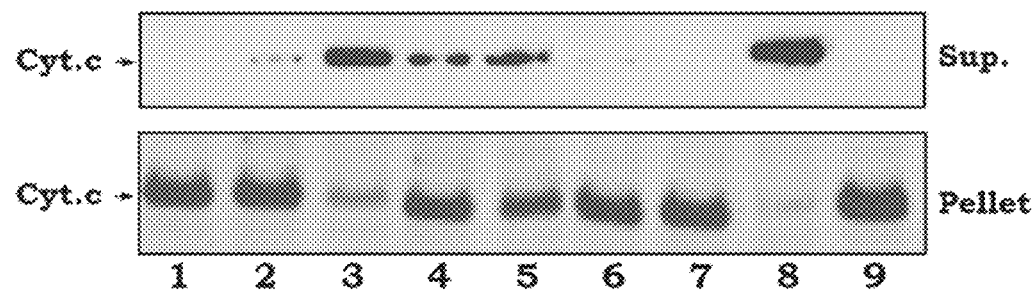
FIG. 4A shows that phosphorylation of BCL10 by the endogenous kinase activity of the purified BCL10-containing protein complex is essential for enhancing its ability to release of cytochrome c from isolated rat mitochondria into supernatant. Purified recombinant BCL10 (R. BCL10, 50 ng) was incubated with rat mitochondria in mixtures containing or not containing the eluted proteins from the BCL10 affinity column in the presence or absence of ATP and/or its non-hydrolysable analogue (γS-ATP) as shown in Lanes 1-6. Lane 7, BCL10 was incubated with purified mitochondria in the absence of recombinant BCL10 and ATP. Lane 8, recombinant t-Bid (25 ng) was incubated with the purified mitochondria. Lane 9 shows the results from purified mitochondria incubated with only the reaction buffer and ATP.
Figure 4B:
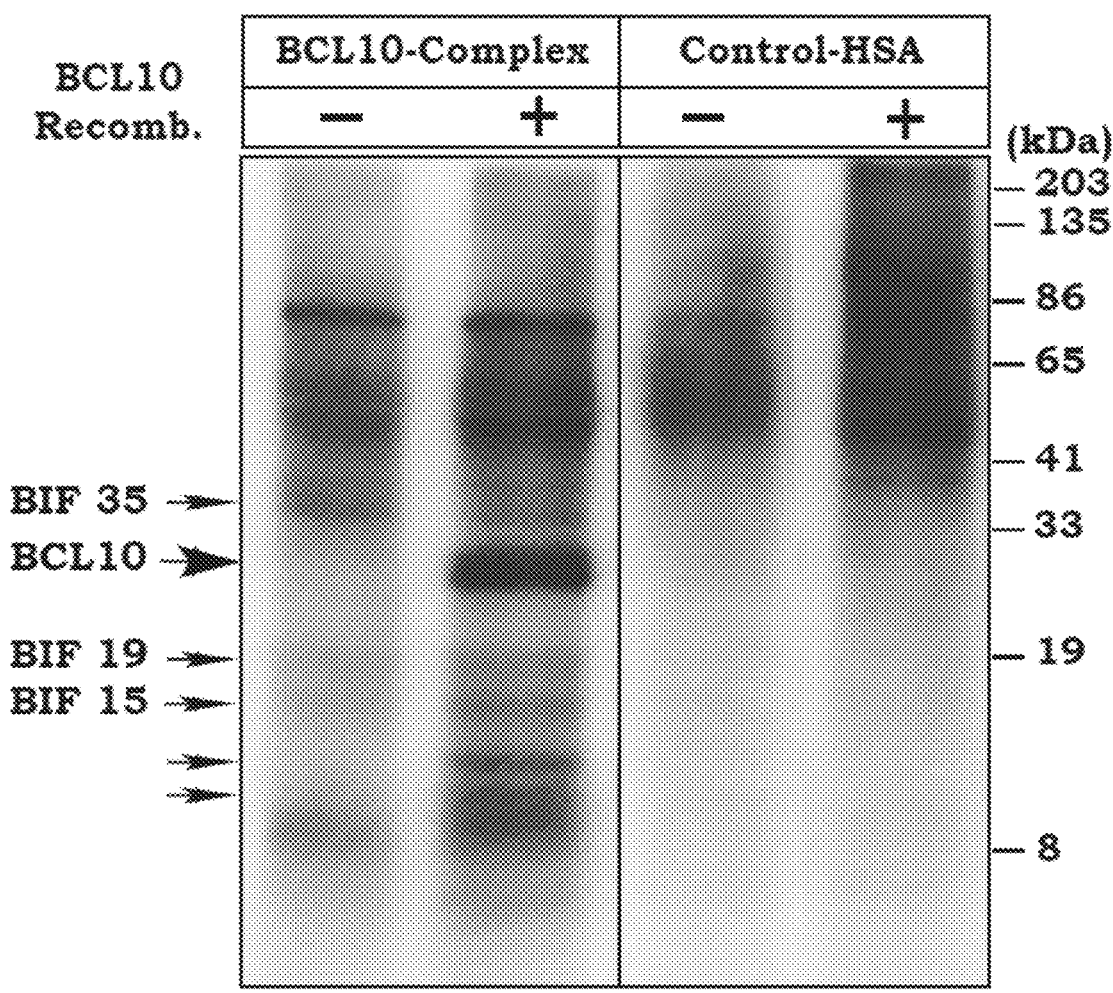
FIG. 4B. PAGE resolution of proteins eluted from the BCL10 affinity column or a HAS control column after incubation with no (−) or with (+) BCL10 and radiolabeled ATP. Bands were visualized by autoradiography.
Figure 5A:
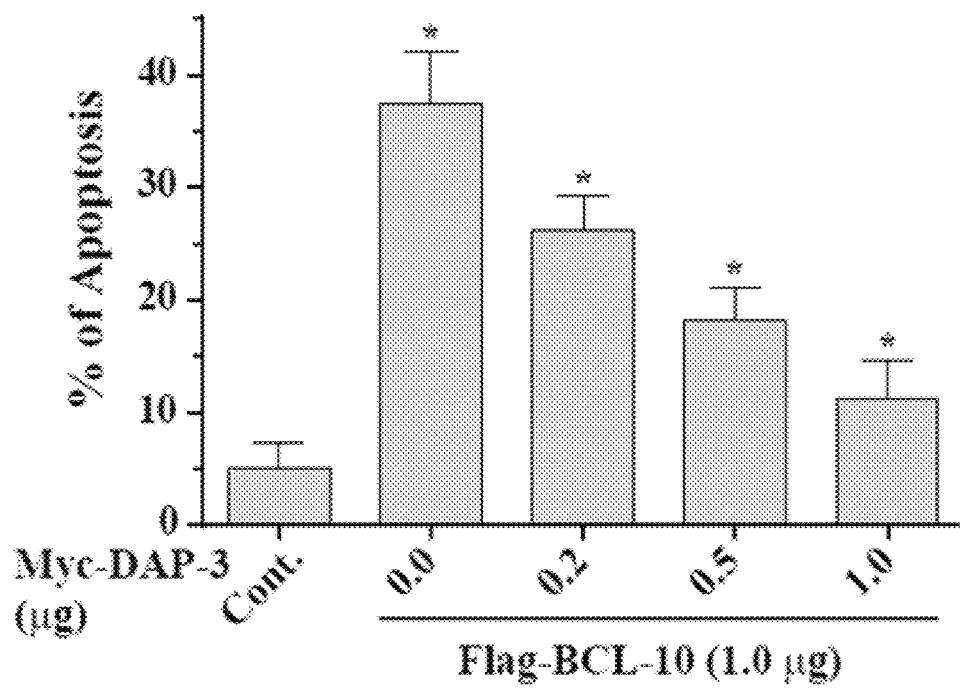
FIG. 5A shows that DAP3 inhibits BCL10-induced apoptosis in HeLa cells. An equal number of HeLa cells were co-transfected with a Flag-BCL10 (1.0 µg) and increasing concentrations of Myc-DAP3 constructs (0.0 to 1.0 µg) or the empty vectors (control). After 72 h of incubation, cells were analyzed for apoptosis by a flow cytometer after staining with FITC-annexin V/7AAD. The percentage of total apoptotic cells (early and late stages) are shown in the graph for three independent experiments as the mean±SD. (*) represents values that are statistically significant.
Figure 5B:
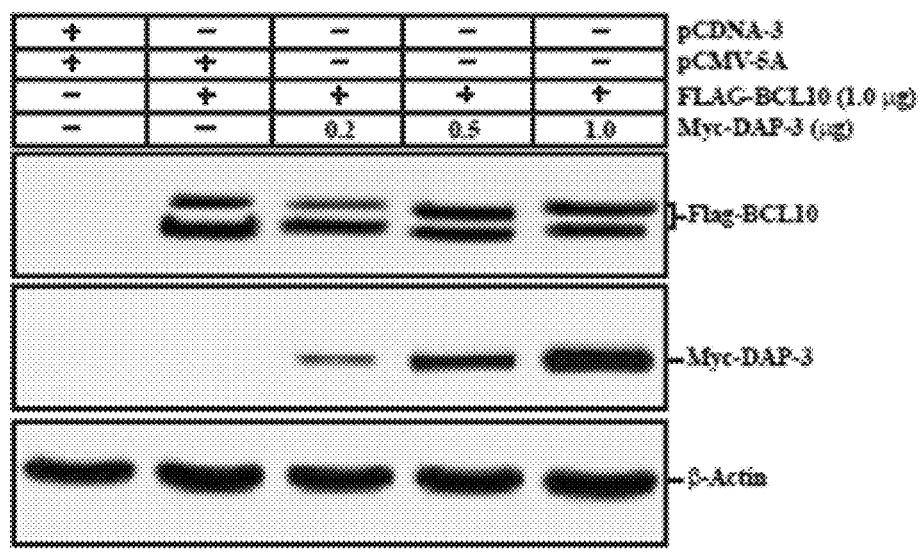
FIG. 5B shows immunoblots for the expression of Flag-BCL10 and Myc-DAP3 in the transfected cells shown in FIG. 5A. β-actin was used as a loading control.

As shown in FIG. 4B, the endogenous kinase activity of the complex was specifically able to phosphorylate the recombinant BCL10. Although there might be a nonspecific kinase activity in the eluent from the control HSA column, however, it did not phosphorylate the recombinant BCL10. By contrast with the phosphorylation pattern of the proteins from the control column, the kinase activity of the BCL10 was also able to phosphorylate BIF35, BIF19 and BIF15 in the presence and absence of recombinant BCL10. At least one additional phosphorylated band in the BCL10 complex test samples (~10 kDa) was also detected that was absent from the HSA counterpart controls. Although the specific kinase responsible for phosphorylating BCL10 and the other BIFs remains to be identified, the results presented in FIGS. 4A and 4B provide compelling evidence that the cytochrome c releasing activity of the complex is enhanced by phosphorylation of BCL10 and potentially other factors in the complex. Therefore, the potential direct or indirect modulation of the phosphorylation of BCL10 and one or more of its associated factors for treating BCL10 associated diseases, or the use of this activity as diagnostic or prognostic tool for monitoring these diseases is part of the present disclosure.

The role of DAP3, a member of the BCL10-containing protein complex on BCL10-induced apoptosis and BCL-associated activation of NF-κB was also investigated. Results are shown by FIGS. 5A-5G. DAP 3 was found to inhibit BCL10-induced apoptosis in HeLa cells. Briefly, an equal number of HeLa cells were co-transfected with a Flag-BCL10 (1.0 µg) and increasing concentrations of Myc-DAP3 constructs (0.0 to 1.0 µg) or the empty vectors (control). After 72 h of incubation, cells were analyzed for apoptosis by a flow cytometer after staining with FITC-annexin V/7AAD. The percentage of total apoptotic cells (early and late stages) are shown in the graph for three independent experiments as the mean±SD. A representation for the flow cytometry plots is shown for one experiment (*) represents values that are statistically significant. The immunoblots shown are for the expression of Flag-BCL10 and Myc-DAP3 in the transfected cells. β-actin was used as a loading control.

These results indicate the value of targeting the structural and functional association of the BCL10-containing protein complex and DAP3 for the purpose of modulating apoptosis and cell-death related to BCL1-associated diseases such as cancer, diabetes, neurodegenerative disorders and autoimmune diseases; or to target this interaction between DAP3 and the BCL10-containing protein complex to modulate activation of NF-κB for enhancing innate and adaptive immunity, to regulate maturation of lymphocytes, and for treating various inflammatory diseases or disorders related to malfunction of BCL10, including asthma, atherosclerosis, cardiovascular disease, arthritic and microbial infections, cancer, neurological diseases such as Alzheimer's disease, obesity and diabetes. This interaction between DAP3 and the BCL10-containing protein complex may also be targeted to modulate NF-κB expression of COPX-2 and iNOS, cytokines such as TNF, IL-1, IL-6, IL-8 and chemokines, adhesion molecules, cell cycle regulatory molecules, viral proteins and angiogenic factors.

To further confirm the inhibitory effect of DAP3 on BCL10-induced apoptosis, DAP3 expression in HeLa cells was knocked down by a specific siRNA and compared apoptosis induced by overexpression of BCL10 in both the depleted and non-depleted cells. Briefly, equal numbers of HeLa cells were transfected with either a control siRNA or siDAP3 (100 pmol, see FIG. 6A. After 48 h incubations, the same cells were transfected with increasing concentration of Flag-BCL10 construct (0.2 to 1.0 µg) or empty vector (pCDNA3, 1.0 µg as a control) and incubated for additional 48 hr subsequently, treated cells were analyzed for apoptosis after staining with FITC-annexin V/7AAD. The graph represents the total apoptotic cells (early and late stages) expressed as the mean±SD of three independent experiments ((*) for statistically significant values).

A representation for the flow cytometry data is shown for one experiment in FIGS. 6B-6K. The Western blots shown are from extracts of treated samples as indicated on top of each blot. β-actin was used as a loading control is shown by FIG. 6L.

Figure 6A:
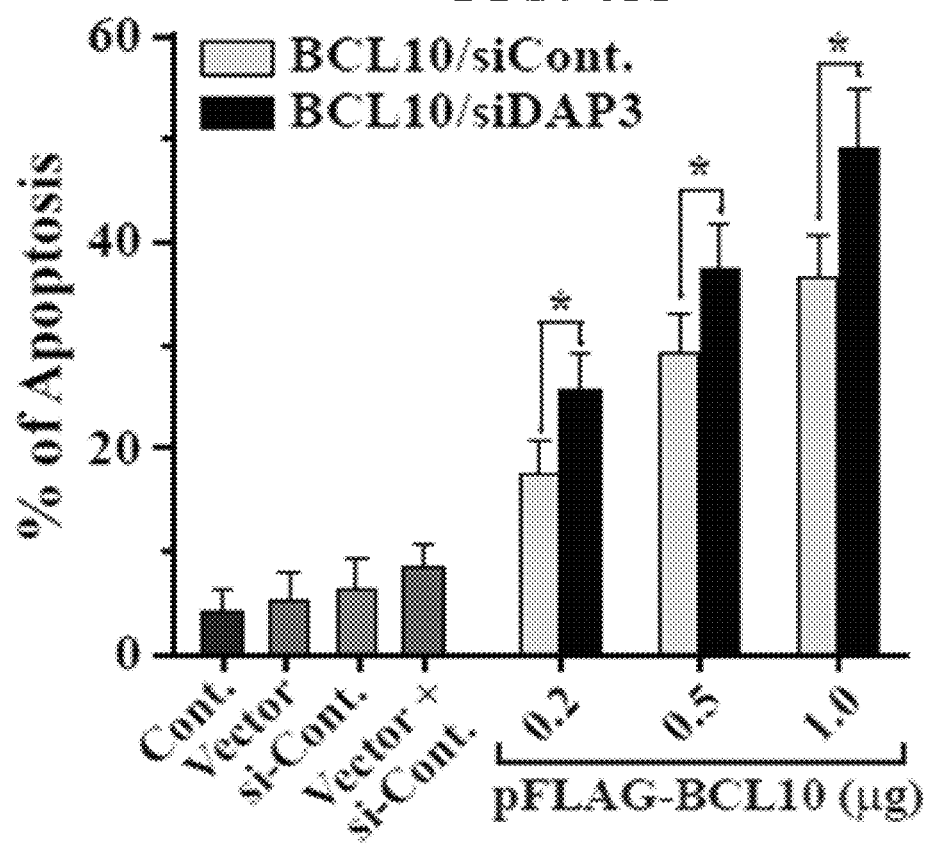
FIG. 6A shows that the depletion of DAP3 enhances the apoptotic activity of BCL10. The graph represents the total apoptotic cells (early and late stages) expressed as the mean±SD of three independent experiments. (*) for statistically significant values. A representation for the flow cytometry data is shown for one experiment. (*) represents values that are statistically significant.

As shown in FIG. 6A, depletion of DAP3 enhanced the proapoptotic activity of transfected BCL10 cells at all the tested concentrations when compared to its effect in non-depleted cells. Apoptosis increased from 8.6±2.1% in cells treated with both control siRNA and pCDNA3 to 25.6±3.6% and 49.3±5.5% in the depleted cells transfected with 0.2 µg and 1.0 µg of the flag construct of BCL10, respectively. However, the percentages of dead cells were only 17.6±3.3% and 36 0.7±4.1% in transfections lacking the DAP3 silencer. Taken together, the above results indicate that DAP3 is a negative regulator for the BCL10 proapoptotic activity. The efficiency of DAP3 knockdown using siRNA in the test samples was confirmed by immunoblotting of the protein with its specific antibody as shown by FIG. 6L.

Figure 6L:
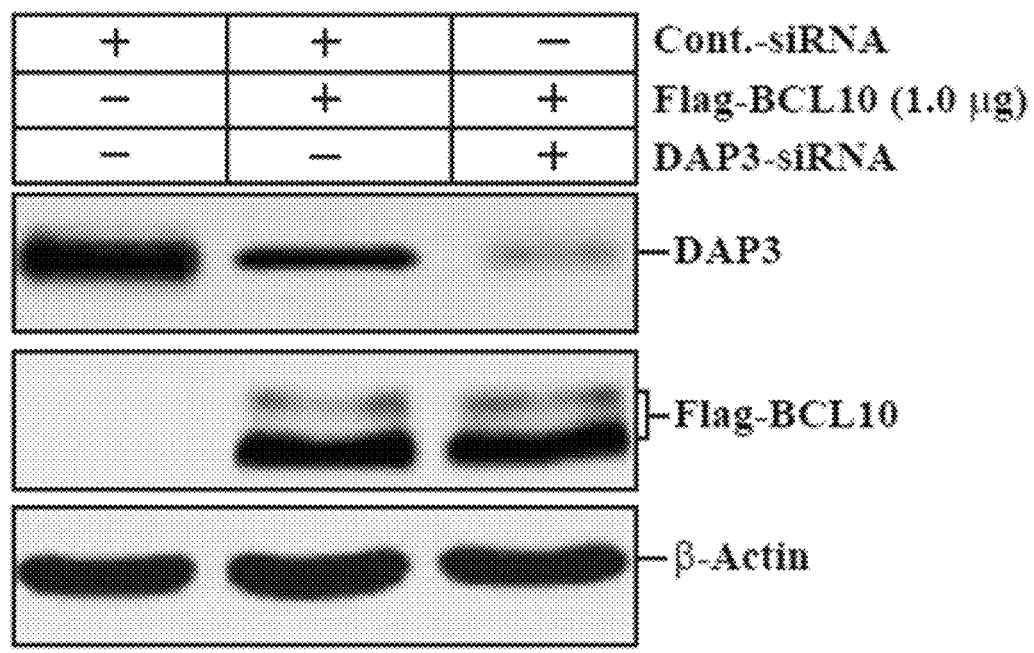
FIG. 6L depicts Western blots shown from extracts of treated samples as indicated on top of each blot. β-actin was used as a loading control.
Figure 7A:
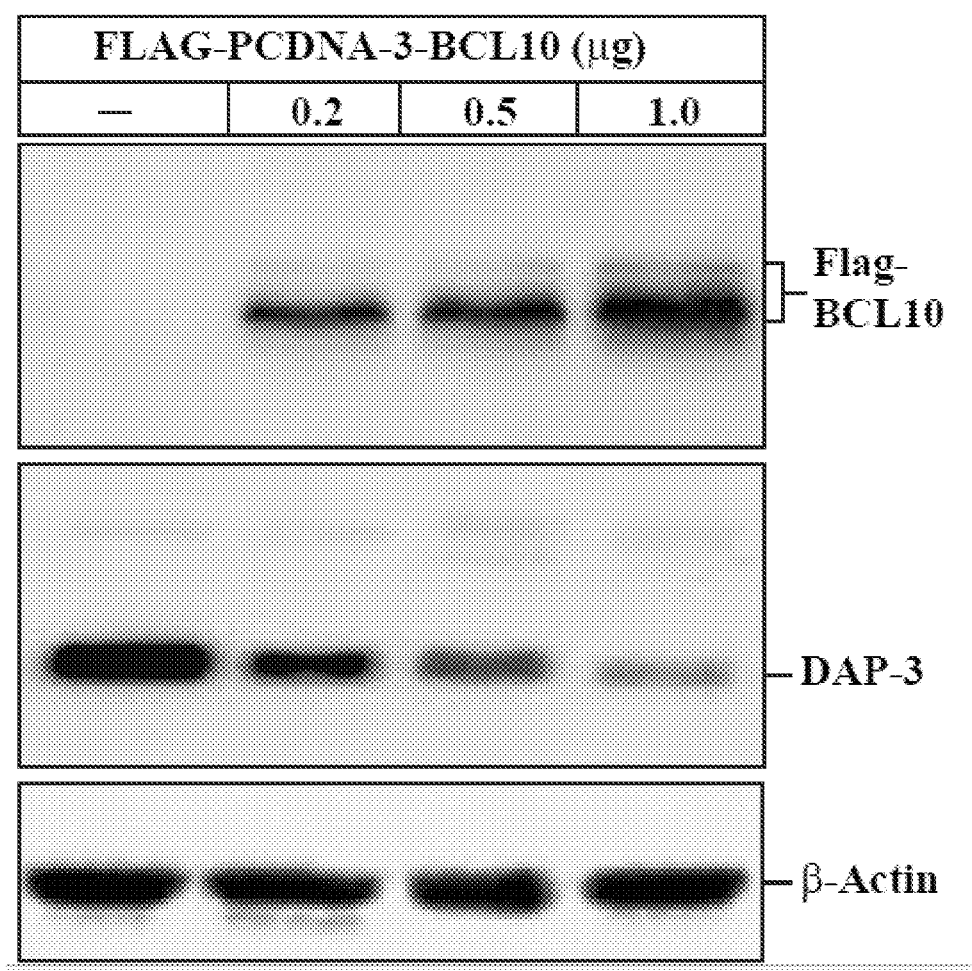
FIG. 7A shows that BCL10 inhibits the expression of DAP3 as determined by Western blotting analysis.
Figure 7B:
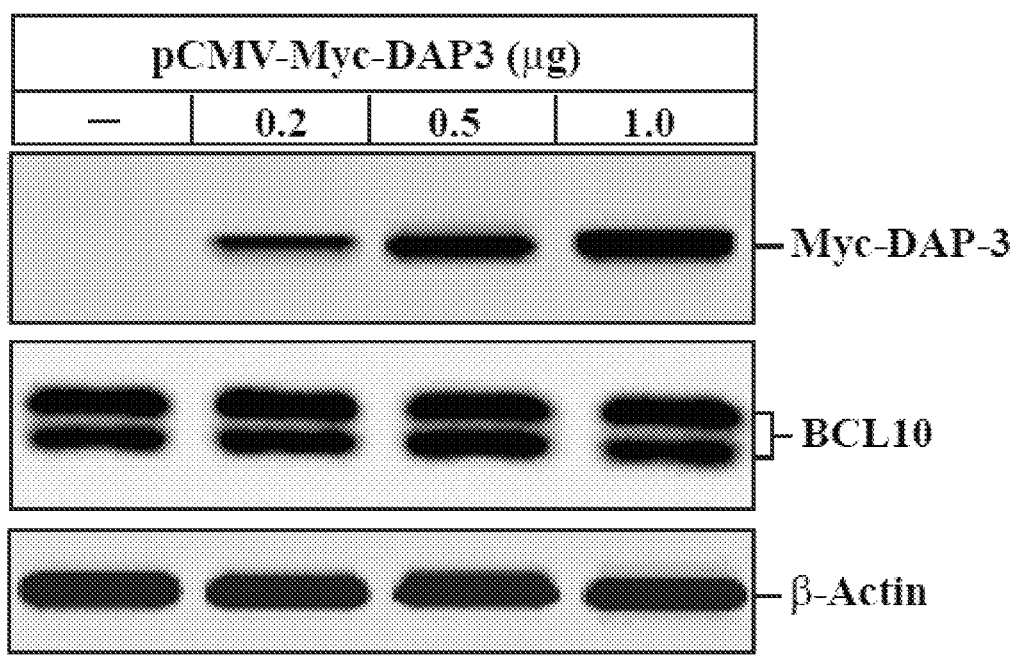
FIG. 7B shows levels of BCL10 and Myc-DAP3 expressed by transfected cells analyzed by Western blotting. β-Actin was used as a loading control.
Figure 7C:
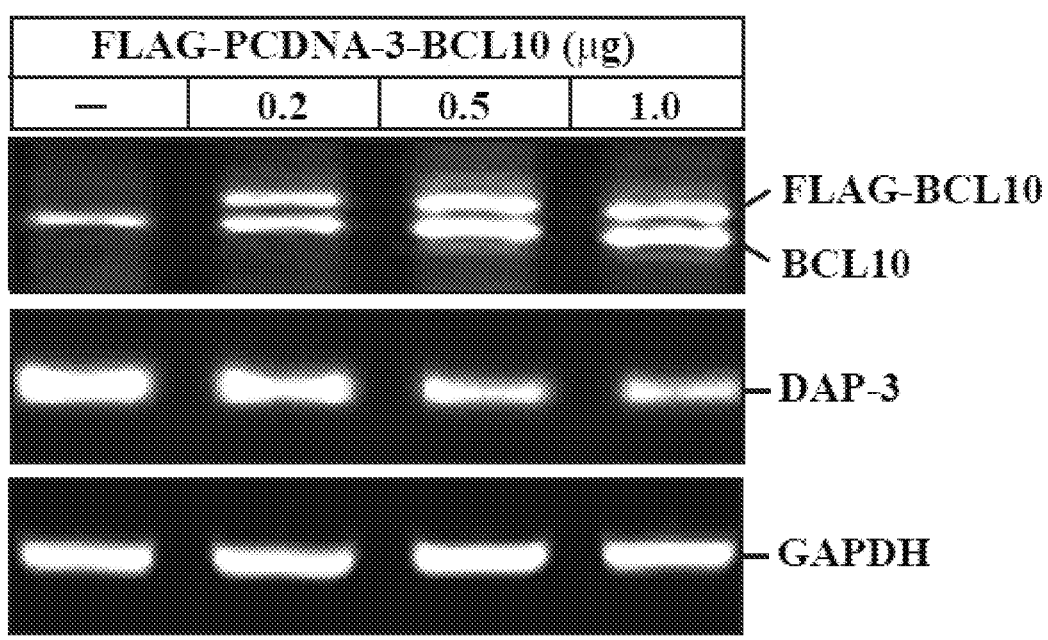
FIG. 7C shows levels of RNA encoding BCL10 and DAP3 as determined by a semi-quantitative PCR protocol. The housekeeping gene GAPDH was used as a loading control.

It was noticed that in FIG. 6L (lane 2) that overexpression of BCL10 caused an approximate 60% reduction in the endogenous levels of DAP3 suggesting that BCL10 may affect DAP3 expression. Briefly, equal numbers of HeLa cells were transfected with a control pCDNA3 or with increasing concentration of Flag-BCL10 constructs (0.2 to 1.0 μg) for 48 h, and the expression of Flag-BCL10 and DAP3 was determined by Western blotting analysis; FIG. 7A. HeLa cells were transfected with a control vector or pCMV-Myc-DAP3 for 48 h, and the levels of BCL10 and Myc-DAP3 were analyzed by Western blotting. β-Actin was used as a loading control; FIG. 7B. HeLa cells were transfected as described in FIG. 7A for 48 h, then RNA was extracted and expression of BCL10 and DAP3 was determined by a semi-quantitative PCR protocol. The housekeeping gene GAPDH was used as a loading control; FIG. 7C.

As shown in FIG. 7A, overexpression of Flag-BCL10 coincided with decreased protein levels of DAP3. Conversely, overexpression of Myc-DAP3 did not interfere with protein levels of endogenous BCL-10; FIG. 7B. As indicated in FIG. 7C, increased expression of Flag-BCL10 was associated with a reduction in DAP3 transcripts. The level of DAP3 RNA is ~4-times less in cells transfected with 1.0 μg of FLAG-BCL10 than transfections containing the control vector. Together, these results indicate that BCL10 suppresses the expression of DAP3 rather than promoting protein degradation.

The results presented in FIGS. 2 and 4 strongly suggest that BCL10 induces release of cytochrome c through its action within the complex containing the other BCL10 associated factors (BIGFs). Moreover, the finding that DAP3 inhibits apoptosis induced by BCL10 disclosed above, suggests that it may interfere with the ability of BCL10 complex to release cytochrome c from mitochondria. To investigate this possibility, the effect of knocking-down DAP3 on the ability of BCL10 to release cytochrome c was evaluated. Briefly, after incubation for 48 with the indicated siRNA, cells were transfected with increasing concentration of Flag-BCL10 constructs (0.1 μg to 1.0 μg), incubated for additional 30 h. subsequently, the cytosolic and mitochondrial fractions were separated from the different samples and analyzed for the presence of cytochrome c by immunoblotting with its specific antibody. β-actin was used as a loading control.

Figure 8A:
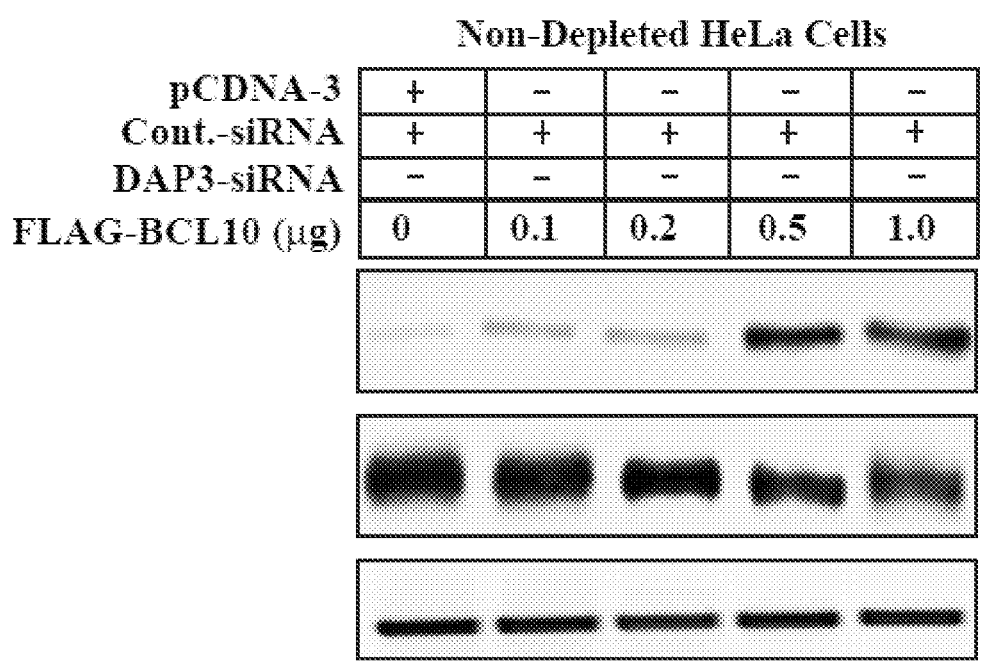
FIG. 8A shows that DAP3 suppresses the BCL10-induced release of cytochrome c from the mitochondria of non-DAP3-depleted HeLa cells transfected with control siRNA.
Figure 8B:
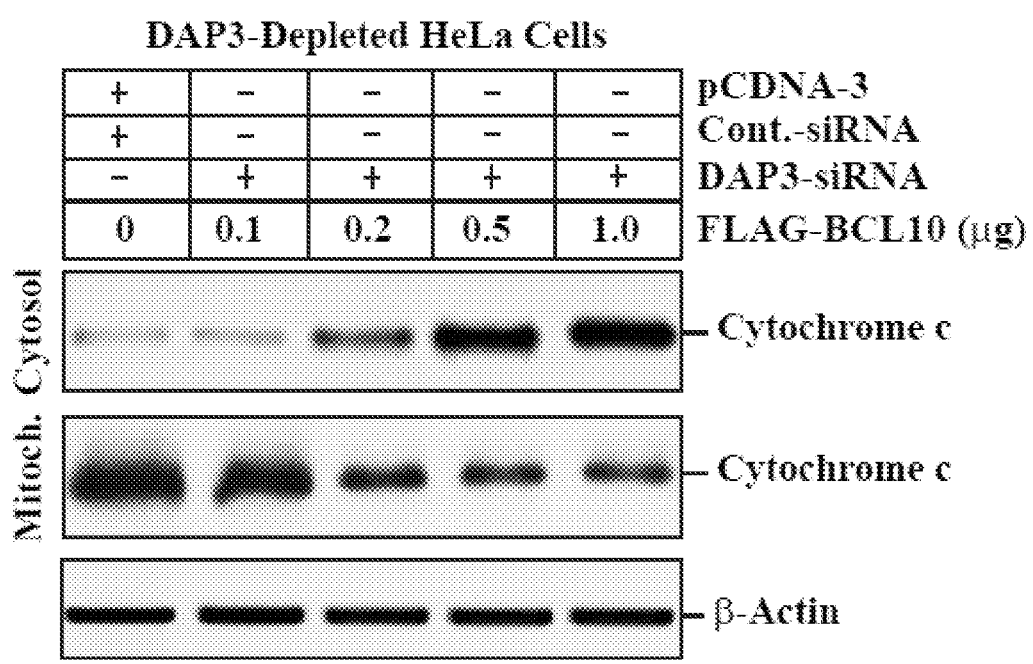
FIG. 8B shows release of cytochrome c from mitochondria of DAP3 depleted cells transfected with siDAP3. β-actin was used as a loading control.

After silencing the expression of DAP3 in HeLa cells, the cells were treated with increased concentrations of FLAG epitope tagged BCL10 construct, and the release of cytochrome c from mitochondria to the cytoplasm was analyzed by immunoblotting for cytochrome c in fractionated cytosolic and mitochondria extracts from the treated cells. FIG. 8A shows the results obtained from cells not depleted for DAP3; FIG. 8B shows results from cells depleted for DAP3.

Depletion of DAP3 in HeLa cells was associated in an approximate 30% increase in the intensity of the detected cytochrome c bands in the cytosolic fractions of depleted cells when compared to the signal in non-depleted cells at the different BCL10 construct concentrations. Conversely, the levels of cytochrome in the mitochondrial fraction decreased in proportions that parallel the increase of the protein in the cytosolic extracts (FIGS. 8A and 8B). These results show that the ability of DAP3 to inhibit BCL10-induced apoptosis is mediated by preventing the release of cytochrome c from mitochondria, and confirm the protective effect of this protein on this organelle. This agrees with disclosure herein showing that depletion of DAP3 enhances apoptosis and show that depletion of DAP3 sensitizes cells to BCL10-induced cytochrome c release from mitochondria and subsequently activates n apoptosis pathway.

BCL10 mutations found in solid and hematological cancers are in a C-terminal coding region and such mutants are defective for inducing apoptosis.

To investigate whether the C-terminal domain of BCL10 is required for its association with DAP3, HeLa cells were transfected with the N-terminal (aa. 1-97), C-terminal (aa. 104-233) or full length BCL10, and the co-immunoprecipitation of DAP3 with the different variants of BCL10 was assessed by Western blotting with a specific anti-DAP3 antibody.

Briefly, equal numbers of HeLa cells were transfected with a control vector or Flag-epitope tagged N-terminus domain of BCL10 (aa. 1-97), C-terminus domain (aa. 1(4-233) or the full length BCL10. After 48 h of incubation, equal extracts (200 μg) from the transfected cells were incubated with a 50 μL of affi-gel-bound anti-Flag antibody. After eluting the antibody-bound proteins, the presence of DAP3 in the immune-precipitates (IP) was detected by Western blotting. The expression of the Flag-BCL10 protein variants in the extracts (IB) was also assessed. β-actin was used as a loading control to ensure equal protein loading.

Figure 9:
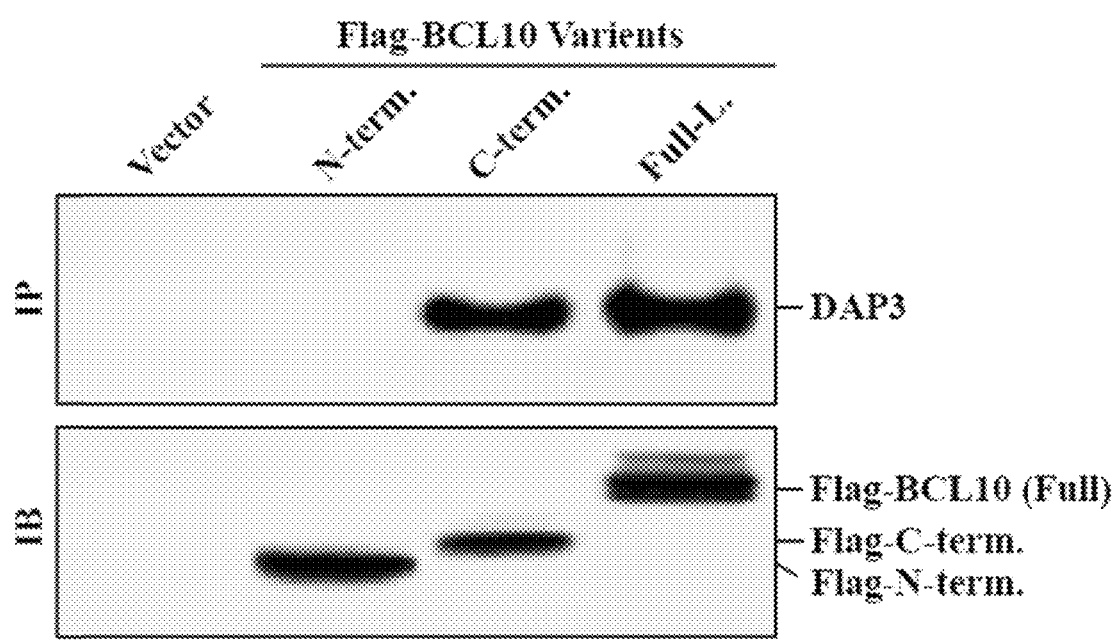
FIG. 9 shows that DAP3 interacts with the C-terminus domain of BCL10. BCL10 N-terminal domain spans aa residues 1-97 and C-terminal domain spans aa residues 104-233. The presence of DAP3 in the immune-precipitates (IP) was detected by Western blotting. The expression of the Flag-BCL10 protein variants in the extracts (IB) was also assessed. β-actin was used as a loading control to ensure equal protein loading (not shown).

Results are shown by FIG. 9 and show that DAP3 was co-immunoprecipitated with both the full length and the C-terminal domain of BCL10, but not with the CARD (N-terminus) domain of BCL10, confirming the critical role of this region for the functional association between both proteins. However, whether DAP3 associates directly with the C-terminal domain of BCL10 or mediated by another factor in the BCL10 complex remain to be determined. These results show that DAP3 interacts with the C-terminus domain of BCL10.

Figure 10A:
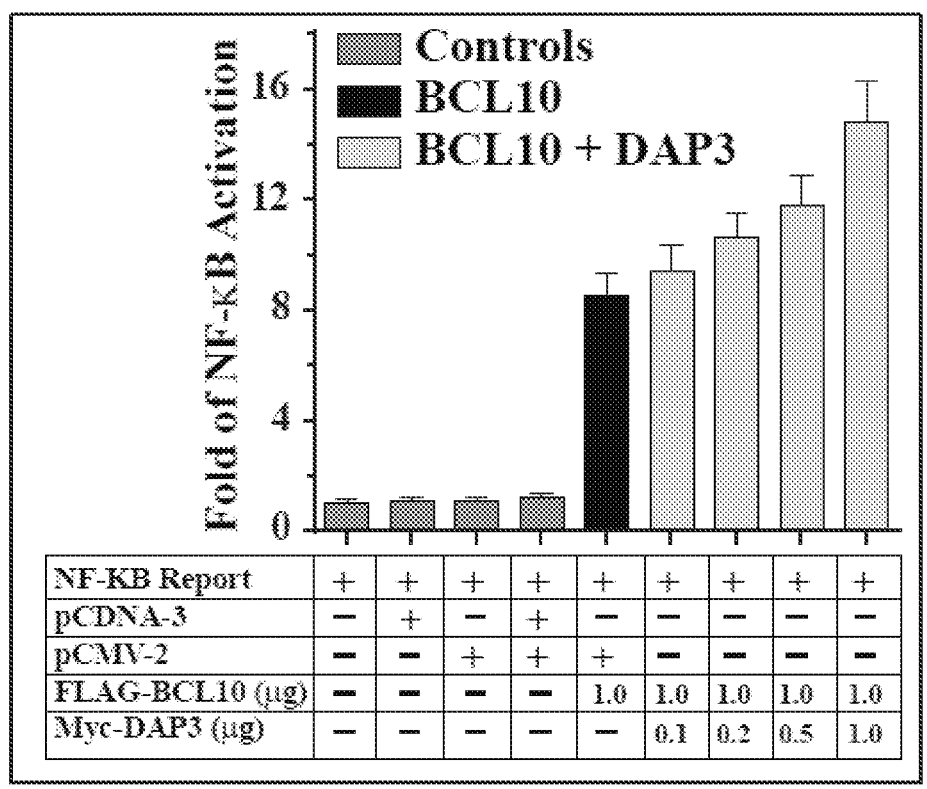
FIG. 10A shows that DAP3 enhances BCL10-induced activation of NF-KB. Equal Numbers of Jurkat cells were transfected with the control vectors or (1.0 µg) of Flag-BCL10 and increased concentrations of Myc-DAP3 (0.1 to 1.0 µg) constructs along with 5×-NFKB luciferase and LacZ reporters as indicated in the bottom of the graph. After incubation for 48 h, activation of NF-KB was measured as luciferase activity in the extracts prepared from the different transfections and results were expressed as the mean±SD-fold of activation, from three independent experiments, relative to the background control. Transfection efficiencies were normalized against β-galactosidase activity in each extract.

To investigate the effect of DAP3 on the ability of BCL10 to activate NF-κB, Jurkat cells were transfected with 1.0 μg of FLAG-BCL10 along with increasing concentrations Myc-DAP-3 constructs (0 to 1.0 μg), and their effect on activation of the NF-κB-luciferase reporter which was transfected in the same cells was determined as described under the methods section. Briefly, as shown by FIG. 10A, equal Numbers of Jurkat cells were transfected with the control vectors or (1.0 μg) of Flag-BCL10 and increased concentrations of Myc-DAP3 (0.1 to 1.0 μg) constructs along with 5×-NFKB luciferase and LacZ reporters as indicated in the bottom of the graph. After incubation for 48 h, activation of NF-KB was measured as luciferase activity in the extracts prepared from the different transfections and results were expressed as the mean±SD-fold of activation, from three independent experiments, relative to the background control. Transfection efficiencies were normalized against β-galactosidase activity in each extract. Increased concentrations of Flag-BCL10 constructs (0.2 to 1.0 μg) were transfected into Jurkat cells containing and not containing a knockdown expression of DAP-3 along with the NF-KB and LacZ reporter as indicated as reported by FIG. 10B. Activation of the luciferase reporter was measured as indicated for FIG. 10A.

As shown by FIG. 10A, while transfection with 1.0 μg of BCL10 alone was able to increase activation of the NF-κB 8.5±0.83-fold over the control lacking BCL10 transfection, cotransfections of 1.0 μg BCL10 along with 0.2 μg and 1.0 μg of DAP3 constructs showed 10.6±0.9-fold and 14.8±1.5-fold increase in the luciferase activity over the same control, respectively. The expression of Flag-BCL10 and Myc-DAP3 in the different transfected cells was confirmed by immunoblotting of their respective proteins using anti-Flag and anti-Myc antibodies. These data show that DAP3 augments BCL10-induced activation of NF-κB and that DAP3 enhances BCL10-induced activation of NF-κB.

Figure 10B:
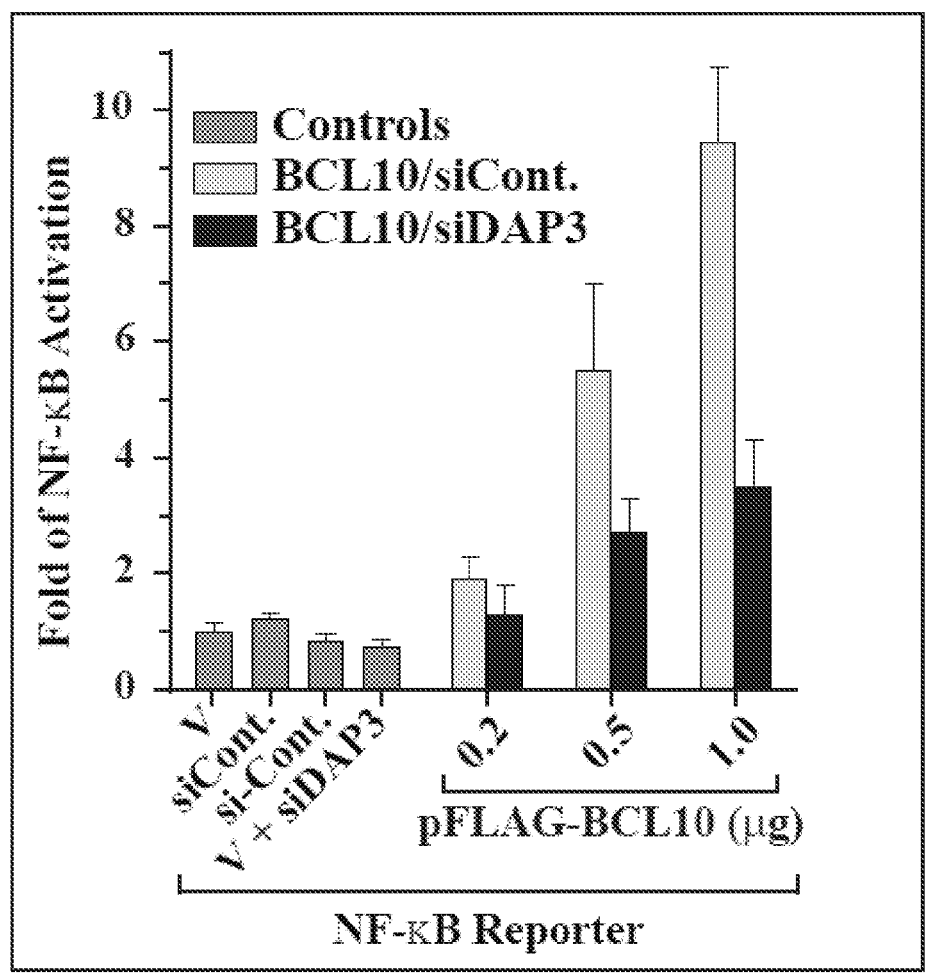
FIG. 10B plots fold of NF-κB activation vs. NF-κB luciferase reporter in control and si-RNA transfected cells. As shown, knock down of DAP3 expression by siDAP3 reduced NF-κB activation compared to si-RNA control.

To further confirm the regulatory role of the endogenous DAP3 on BCL10-mediated activation of NF-κB, the effects of increasing expression of BCL10 in Jurkat cells depleted from DAP3 were analyzed. The ability of BCL10 to induce activation of NF-κB in DAP3 depleted Jurkat cells was dramatically reduced when compared to non-depleted cells. Activation of NF-κB was reduced from 9.3±1.3-fold in the absence of siDAP-3 to 3.5±0.8-fold in the DAP-3 knocked-down cells, when both compared to the controls lacking transfected BCL10 (FIG. 10B). BCL10 and DAP3 expression in the different transfected cells was confirmed by Western blotting analysis using anti-Flag and anti-DAP3 antibodies, respectively (not shown). Taken together, these findings indicate that DAP3 enhances activation of NF-κB mediated by the BCL10 complex.

Example 2

Expression of BCL10 and its Associated Factor in Obesity and Insulin Resistivity in White Blood Cells of Normal Lean, Obese, Diabetic Patients and Normal Lean with a Family History of Diabetes The work described in this Example was done in two stages. The first stage involved 93 human subjects from the Endocrinology Clinic at the University of Jordan Hospital. The subjects were divided into four groups: healthy, lean individuals with no family history of type-2 diabetes (group 1, n=21), healthy, lean individuals with family history of type-2 diabetes (group 2, n=22), obese, non-diabetic individuals (group 3, n=20), and type-2 diabetic patients (group 4, n=30). In the second stage of the project, 29 additional individuals were recruited in order to increase the diabetic group and to divide the obese group into those that did not have family history and those that had. The new classification was as follows: healthy, lean individuals with no family history (group 1, n=21), healthy, lean individuals with family history (group 2, n=22), obese, non-diabetic individuals without family history (group 3, n=19), obese, non-diabetic individuals with family history (group 4, n=23), and diabetic patients (group 5, n=37). All subjects were consented according to the approved Institutional Review Board (IRB, protocol number 232/2016). Two mL of peripheral blood were collected from each subject. A physical exam was performed, and glucose levels and lipid profiles were measured for all subjects. Immediately following blood collection, total RNA was extracted using QIAamp RNA Blood MiniKit (Qiagen, Cat No. 52304) according to manufacturer's instructions. cDNA was synthesized from RNA using the Quantitect Reverse Transcriptase kit (Qiagen, Cat No. 205310) according to manufacturer's instructions. All cDNA samples were kept frozen at −80° C. until used for qPCR (real-time quantitative PCR) analyses. Real-time PCR was then carried out using Quantitect SYBR Green PCR kit (Qiagen, Cat No. 205310) in IQ Real-Time System (Biorad, Hercules, CA, USA). For each gene, optimization for the annealing temperature was first performed single using gradient C1000 Thermal Cycler (Biorad, USA). The real-time PCR protocol consisted of a denaturation step at 95° C. for 2 min, followed by 35 cycles of amplification at 95° C. for 15 s, 30 sec at the optima annealing temperature for each gene, and 72° C. for 10 s. The PCR reaction mixtures were composed of 4 μl Master mix (KAPA Biosystems, USA), 0.5 μl of 5 pmol forward primers, 0.5 μl of 5 pmol reverse primers, 300-500 ng DNA (0.75 μl), and nuclease-free water for a final of 20 μl. Data were normalized for the expression of the actin gene levels by the ΔΔCt method; Pfaffl M W. (2001). A new mathematical model for relative quantification in real-time RT-PCR. *Nucleic Acids Res.*, 29, e45—incorporated herein by reference.

In this work, 93 human subjects from the Endocrinology Clinic at the University of Jordan Hospital were included. The subjects were divided into four groups: healthy, lean individuals with no family history of type-2 diabetes (group 1, n=21), healthy, lean individuals with family history of type-2 diabetes (group 2, n=22), obese, non-diabetic individuals (group 3, n=20), and type-2 diabetic patients (group 4, n=30). All subjects were consented according to the approved Institutional Review Board (IRB, protocol number 232/2016). Physical exam was performed, and glucose level and lipid profile were measured for all subjects (Appendix 11). 2 mL of peripheral blood were collected from each subject and immediately used to extract RNA and generate cDNA library as described under the methods sections. All cDNA samples were kept frozen at −80° C. until used for qPCR (real-time quantitative PCR) analyses. The expression of 7 genes identified herein were analyzed (LSD1, CUL4A, CUL4B, KU70, hTID1, DAP3, NM23), in addition to BCL10 and NFκB1, in the four groups of human subjects. The expression of MAT1 which was previously reported as part of the BMC complex (composed of CARMA1, BCL10 and MALT1) was analyzed. The analyses for the expression of the above 10 gens are summarized in Table 1. The results showed that five genes had reduced expression in diabetic individuals only by more than two folds relative to group 1. The genes were LSD1, CUL4B, hTID1, MALT1, and NF-KB1. Interestingly, BCL10 was found to be upregulated among lean, non-diabetic individuals with family history of diabetes by more than two folds relative to those without family history suggesting their tendency to develop the disease. The reduced expressions of LSD1, CUL4B, hTID1, MALT1 and NF-KB1 in group 4 of diabetic patients suggested their potential role in developing the disease. Therefore, they could be targeted as prognostic markers or candidates for therapeutic approaches in diabetes.

The results described in Table 1 prompted further study for confirmation and more diabetic patients were recruited increasing the group by 7. In addition, more obese individuals were also included, and this group could be differentiated as those with and without family history of diabetes. Five genes of the 10 analyzed previously were selected, namely, CUL4B, BCL10, NF-κB, DAP3, and MALT1.

As can be seen in Table 2, DAP3 was still not differentially expressed among the five groups. In addition, MALT1 and CUL4B were also consistently down-regulated among diabetic patients by more than two folds, again showing their potential relevance as markers or players in diabetic patients.

On the other hand, NF-KB1 became a little less than two-fold differentially expressed with increasing sample size, although it is still expressed at low levels. Interestingly, NF-KB1, MALT1, and BCL10 appeared to be up-regulated by more than two folds among obese individuals without family history. MALT1 was almost two-folds upregulated among obese individuals with family history and three-folds in obese individuals without a family history suggesting its importance of increasing even further in future studies. The correlation between the levels of NF-KB1 and MALT1 among the different groups further support the transcriptional regulation of MALT1 by NF-KB1. BCL10 was also expressed by more than two folds among lean individuals with family history suggesting that it may have a similar role among non-diabetic individuals who are either lean with family history and those who are obese without family history.

Overall, these results show perturbation of the levels of some of these regulatory molecules and their usefulness as diagnostic markers and/or therapeutic targets as they correlate with development of diabetes. Thus, these correlations provide for use of expression levels of BCL10 and/or any of its thirteen associated proteins as early diagnostic markers for developing diabetes; for the use of BCL10 and one or more of its thirteen associated factors as prognostic markers for the disease progression or for monitoring treatment responses; or therapeutic targeting of BCL10 and one or more of its thirteen associated factors to treat diabetes, insulin resistivity, obesity, or complications of diabetic disorders such as nephropathy, neuropathy, retinopathy and other diabetes associated inflammatory diseases.

BCL10 has been implicated in obesity and insulin resistance through its ability to activate NF-κB. This association was investigated by analyzing the expression of BCL10 and its associated factors in peripheral blood samples from obese and type-2 diabetic patients and compared their expression in normal lean subjects. In this innovative study, we intended to provide evidence that insulin resistance is associated with modulated expression of BCL10 and one or more of its associated factors that are required for activation of NF-κB and apoptosis.

TABLE 1

Summary of the relative expression of BCL10 complex genes in four different groups.
Data were normalized for the expression of the actin gene levels by the ΔΔCt method.

| Group | n | LSD1 | CUL4A | CUL4B | KU70 | hTID1 | DAP3 | NM23 | BCL10 | NF-κB | Malt1 |
|---|---|---|---|---|---|---|---|---|---|---|---|
| Lean, non-diabetic, no family history | 21 | 1 | 1 | 1 | 1 | 1 | 1 | 1 | 1 | 1 | 1 |
| Lean, non-diabetic, family history | 22 | 0.89 | 1.4 | 0.8 | 1.6 | 1 | 0.85 | 0.6 | 2.24 | 0.73 | 0.83 |
| Obese, non-diabetic | 20 | 0.99 | 1.1 | 1 | 1 | 1 | 0.72 | 1 | 0.98 | 1.23 | 0.96 |
| Diabetic | 30 | 0.43 | 0.9 | 0.43 | 1.5 | 0.4 | 0.81 | 0.7 | 1.31 | 0.39 | 0.28 |

TABLE 2

Summary of the relative expression of selective genes in five different groups. Data were normalized for the expression of the actin gene levels by the ΔΔCt method.

| Group | n | CUL4B | DAP3 | MALT1 | NF-kB | BCL10 |
|---|---|---|---|---|---|---|
| Lean, non-diabetic with no family history | 21 | 1.00 | 1.00 | 1.00 | 1.00 | 1.00 |
| Lean, non-diabetic with family history | 22 | 0.84 | 0.85 | 0.83 | 0.73 | 2.24 |
| Obese, non-diabetic with no family history | 19 | 0.96 | 1.42 | 3.24 | 2.20 | 2.34 |
| Obese, non-diabetic with family history | 23 | 0.66 | 1.64 | 1.92 | 1.38 | 1.48 |
| Diabetic | 37 | 0.42 | 1.17 | 0.44 | 0.59 | 1.67 |

The previous results were interesting and invited further confirmation. Therefore, more diabetic patients were recruited increasing the group by 7. In addition, more obese individuals were also included, and this group could be differentiated as those with and without family history of diabetes. Five genes of the 10 analyzed previously were selected, namely, CUL4B, BCL10, NF-KB, DAP3, and MALT1.

As can be seen in Table 2, DAP3 was still not differentially expressed among the five groups. In addition, MALT1 and CUL4B were also consistently down-regulated among diabetic patients by more than two folds, again suggesting their relevance as markers or players in diabetic patients.

On the other hand, NF-KB1 became a little less than two-fold differentially expressed with increasing sample size, although it is still expressed at low levels.

NF-KB1, MALT1, and BCL10 appeared to be up-regulated by more than two folds among obese individuals without family history. MALT1 was almost two-folds upregulated among obese individuals with family history and three-folds in obese individuals without a family history suggesting its importance of increasing even further in future studies. The correlation between the levels of NF-KB1 and MALT1 among the different groups further support the transcriptional regulation of MALT1 by NF-KB1. BCL10 was also expressed by more than two folds among lean individuals with family history suggesting that it may have a similar role among non-diabetic individuals who are either lean with family history and those who are obese without family history. These results are consistent with the use of these BCL10 complex genes or proteins for diagnosis of diabetes or for therapeutic intervention. For example, lower expression of LSD1, CUL4B, hTID1, NF-κB and/or Malt1 is characteristic of the diabetic patient compared to non-diabetic subjects and measurement of these levels could be used for diagnosis or the level of expression modified by the various therapeutic procedures disclosed herein. Similar, the decreased or increased expression of other described above may be correlated with the other types of subjects for diagnosis or prognosis or for therapeutic intervention. For example, elevated expression of DAP3, MALT1, and/or NF-κB may be used to distinguish obese subjects with no family history of diabetes from obese subjects with diabetic family history and improve prognosis of diabetes in the obese. Elevated expression of BCL10 in the obese may also be used as a prognostic marker distinguishing lean subjects with a diabetic family history and obese subjects from lean subjects with no family history of diabetes, providing further improvements in prognosis and diabetes risk assessment.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," w % ben used in this specification, specify the presence of stated features, steps, operations, elements, and/or components, but do not preclude the presence or addition of one or more other features, steps, operations, elements, components, and/or groups thereof.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

As used herein, the term "and/or" includes any and all combinations of one or more of the associated listed items and may be abbreviated as "/".

Links are disabled by spelling out of or deletion of "http" or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears. Specifically, polynucleotide and amino acid sequences are incorporated by reference to the accession numbers or other identifiers disclosed herein. When multiple versions of an accession number are available, the last version of the sequence available before this application's filing date may be used.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a disease that is associated with or mediated by BCL10 comprising administering a composition to a subject in need thereof;
wherein said composition comprises:
an agent that modulates the formation of, dissolution of, or activity of, a complex of BCL10 and DAP3, and
a pharmaceutically acceptable carrier or excipient;
wherein said agent comprises:
(i) an antibody that binds BCL10 and/or DAP3, or
(ii) siRNA or miRNA that inhibits or enhances the expression of a gene encoding BCL10 and/or DAP3.

2. The method of claim 1, wherein the disease is cancer and wherein said agent promotes apoptosis by enhancing the expression of BCL10 compared to DAP3.

3. The method of claim 1, wherein the disease is a degenerative disease and wherein said agent inhibits apoptosis by enhancing expression of DAP3 or inhibits cytochrome c release from mitochondria by BCL10.

4. The method of claim 1, wherein said agent inhibits the activation of NF-κB by reducing the expression of DAP3.

5. The method of claim 1, wherein said agent enhances the activation of NF-κB by increasing the expression of DAP3.

6. The method of claim 1, wherein the agent comprises an antibody to BCL10.

7. The method of claim 1, wherein the agent comprises an antibody to DAP3.

8. The method of claim 1, wherein the agent comprises miRNA or siRNA to BCL10.

9. The method of claim 1, wherein the agent comprises miRNA or siRNA to DAP3.

10. The method of claim 1, wherein the disease is cancer and wherein the agent comprises an antibody, siRNA, or miRNA to BCL10 and/or DAP3 that increases apoptosis.

11. The method of claim 1, wherein the disease is a neurodegenerative or autoimmune disease; and wherein the agent comprises an antibody, siRNA, or miRNA to BCL10 and/or DAP3 that decreases apoptosis.

12. The method of claim 1, wherein the disease is diabetes, and wherein the agent comprises an antibody, siRNA, or miRNA to BCL10 and/or DAP3 that decreases apoptosis.

13. The method of claim 1, wherein the agent comprises an antibody that binds to BCL10 and inhibits formation of, or promotes dissociation of the complex of BCL10 and DAP3 thereby reducing proapoptotic activity of said complex.

14. The method of claim 1, wherein the agent comprises an antibody that binds to DAP3 and inhibits formation of, or promotes dissociation of the complex of BCL10 and DAP3 thereby reducing proapoptotic activity of said complex.

15. The method of claim 1, wherein the agent comprises an antibody that binds to DAP3 and an antibody that binds to BCL10 to inhibit formation of, or promote dissociation of the complex of BCL10 and DAP3 thereby reducing proapoptotic activity of said complex.

16. The method of claim 1, wherein the agent comprises siRNA or miRNA that binds to and degrades an RNA transcript encoding BCL10, thereby depleting BCL10 and reducing proapoptotic activity.

17. The method of claim 1, wherein the agent comprises siRNA or miRNA that binds to and degrades an RNA transcript encoding DAP3, thereby depleting DAP3 and promoting apoptotic activity by BCL10.

18. A method for enhancing apoptosis in a human subject, comprising:
administering a composition comprising (i) a pharmaceutically acceptable carrier or excipient, and (ii) BCL10 to the human subject,
wherein the composition depletes DAP3 and enhances release of cytochrome c from mitochondria of the human subject, thereby enhancing apoptosis.

19. A method for inhibiting apoptosis in a human subject, comprising:
administering a composition comprising (i) a pharmaceutically acceptable carrier or excipient, and (ii) DAP3 to the human subject,
wherein the composition inhibits release of cytochrome c from mitochondria of the human subject, thereby inhibiting BCL10-induced apoptosis.

* * * * *

SEQUENCE LISTING

<160> NUMBER OF SEQ ID NOS: 32

<210> SEQ ID NO 1

<400> SEQUENCE: 1

000

<210> SEQ ID NO 2
<211> LENGTH: 233
<212> TYPE: PRT
<213> ORGANISM: Homo sapiens
<220> FEATURE:
<221> NAME/KEY: MISC_FEATURE
<222> LOCATION: (1)..(233)
<223> OTHER INFORMATION: B-cell lymphoma/leukemia 10 isoform 1 [Homo sapiens]; NCBI Reference Sequence: NP_003912.1

<400> SEQUENCE: 2

```
Met Glu Pro Thr Ala Pro Ser Leu Thr Glu Glu Asp Leu Thr Glu Val
1               5                   10                  15

Lys Lys Asp Ala Leu Glu Asn Leu Arg Val Tyr Leu Cys Glu Lys Ile
            20                  25                  30

Ile Ala Glu Arg His Phe Asp His Leu Arg Ala Lys Lys Ile Leu Ser
        35                  40                  45

Arg Glu Asp Thr Glu Glu Ile Ser Cys Arg Thr Ser Ser Arg Lys Arg
    50                  55                  60

Ala Gly Lys Leu Leu Asp Tyr Leu Gln Glu Asn Pro Lys Gly Leu Asp
65                  70                  75                  80

Thr Leu Val Glu Ser Ile Arg Arg Glu Lys Thr Gln Asn Phe Leu Ile
                85                  90                  95

Gln Lys Ile Thr Asp Glu Val Leu Lys Leu Arg Asn Ile Lys Leu Glu
            100                 105                 110

His Leu Lys Gly Leu Lys Cys Ser Ser Cys Gly Pro Phe Pro Asp Gly
        115                 120                 125

Ala Thr Asn Asn Leu Ser Arg Ser Asn Ser Asp Glu Ser Asn Phe Ser
    130                 135                 140

Glu Lys Leu Arg Ala Ser Thr Val Met Tyr His Pro Glu Gly Glu Ser
145                 150                 155                 160

Ser Thr Thr Pro Phe Phe Ser Thr Asn Ser Ser Leu Asn Leu Pro Val
                165                 170                 175

Leu Glu Val Gly Arg Thr Glu Asn Thr Ile Phe Ser Ser Thr Thr Leu
            180                 185                 190

Pro Arg Pro Gly Asp Pro Gly Ala Pro Pro Leu Pro Pro Asp Leu Gln
        195                 200                 205

Leu Glu Glu Glu Gly Thr Cys Ala Asn Ser Ser Glu Met Phe Leu Pro
    210                 215                 220

Leu Arg Ser Arg Thr Val Ser Arg Gln
225                 230
```

<210> SEQ ID NO 3

<400> SEQUENCE: 3

000

<210> SEQ ID NO 4
<211> LENGTH: 2347
<212> TYPE: PRT
<213> ORGANISM: Homo sapiens

```
<220> FEATURE:
<221> NAME/KEY: MISC_FEATURE
<222> LOCATION: (1)..(2347)
<223> OTHER INFORMATION: proto-oncogene tyrosine-protein kinase ROS
      precursor [Homo sapiens; NCBI Reference Sequence: NP_002935.2

<400> SEQUENCE: 4

Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125

Tyr Ile Ile Gln Trp Lys Tyr Ala Gln Leu Leu Gly Ser Trp Thr Tyr
    130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190

Val Pro Glu Thr Ala Pro Leu Ile Arg Asn Ile Glu Ser Ser Ser Pro
        195                 200                 205

Asp Thr Val Glu Val Ser Trp Asp Pro Pro Gln Phe Pro Gly Gly Pro
    210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
            260                 265                 270

Pro Glu Ala Glu Ser Ser Ile Thr Thr Ser Ser Ser Ala Val Gln Gln
        275                 280                 285

Glu Glu Gln Trp Leu Phe Leu Ser Arg Lys Thr Ser Leu Arg Lys Arg
    290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
            340                 345                 350

Met Ser Asp Val Ser Asp Leu Arg Ile Phe Tyr Arg Gly Ser Gly Leu
        355                 360                 365

Ile Ser Ser Ile Ser Ile Asp Trp Leu Tyr Gln Arg Met Tyr Phe Ile
    370                 375                 380
```

-continued

```
Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
            405                 410                 415

Asp Ser Tyr Asn Gly Tyr Val Phe Tyr Leu Leu Arg Asp Gly Ile Tyr
            420                 425                 430

Arg Ala Asp Leu Pro Val Pro Ser Gly Arg Cys Ala Glu Ala Val Arg
            435                 440                 445

Ile Val Glu Ser Cys Thr Leu Lys Asp Phe Ala Ile Lys Pro Gln Ala
            450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
            485                 490                 495

Ala Asp Val Lys Ser Phe Ala Cys Glu Asn Asn Asp Phe Leu Val Thr
            500                 505                 510

Asp Gly Lys Val Ile Phe Gln Gln Asp Ala Leu Ser Phe Asn Glu Phe
            515                 520                 525

Ile Val Gly Cys Asp Leu Ser His Ile Glu Glu Phe Gly Phe Gly Asn
530                 535                 540

Leu Val Ile Phe Gly Ser Ser Gln Leu His Pro Leu Pro Gly Arg
545                 550                 555                 560

Pro Gln Glu Leu Ser Val Leu Phe Gly Ser His Gln Ala Leu Val Gln
            565                 570                 575

Trp Lys Pro Pro Ala Leu Ala Ile Gly Ala Asn Val Ile Leu Ile Ser
            580                 585                 590

Asp Ile Ile Glu Leu Phe Glu Leu Gly Pro Ser Ala Trp Gln Asn Trp
            595                 600                 605

Thr Tyr Glu Val Lys Val Ser Thr Gln Asp Pro Pro Glu Val Thr His
            610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
            645                 650                 655

Pro Gly Pro Trp Ser Glu Pro Ser Val Gly Thr Thr Leu Val Pro Ala
            660                 665                 670

Ser Glu Pro Pro Phe Ile Met Ala Val Lys Glu Asp Gly Leu Trp Ser
            675                 680                 685

Lys Pro Leu Asn Ser Phe Gly Pro Gly Glu Phe Leu Ser Ser Asp Ile
            690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
            725                 730                 735

Ser Glu Asn Tyr His Leu Pro Ser Ile Ala Gly Ala Gly Ala Leu Ala
            740                 745                 750

Phe Glu Trp Leu Gly His Phe Leu Tyr Trp Ala Gly Lys Thr Tyr Val
            755                 760                 765

Ile Gln Arg Gln Ser Val Leu Thr Gly His Thr Asp Ile Val Thr His
            770                 775                 780

Val Lys Leu Leu Val Asn Asp Met Val Val Asp Ser Val Gly Gly Tyr
785                 790                 795                 800
```

```
Leu Tyr Trp Thr Thr Leu Tyr Ser Val Glu Ser Thr Arg Leu Asn Gly
                805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
            835                 840                 845

Val Gln Asp Ser Gln Cys Ile His Leu Tyr Thr Ala Val Leu Arg Gly
850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
            885                 890                 895

Trp Ile Asn Gly Phe Arg Ile Ile Thr Thr Gln Glu Ile Gly Gln Lys
            900                 905                 910

Thr Ser Val Ser Val Leu Glu Pro Ala Arg Phe Asn Gln Phe Thr Ile
            915                 920                 925

Ile Gln Thr Ser Leu Lys Pro Leu Pro Gly Asn Phe Ser Phe Thr Pro
            930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
            980                 985                 990

Leu Ala Ser Glu Gln His Ser Leu Pro Val Phe Thr Val Glu Gly Leu
            995                 1000                1005

Glu Pro Tyr Ala Leu Phe Asn Leu Ser Val Thr Pro Tyr Thr Tyr
    1010            1015            1020

Trp Gly Lys Gly Pro Lys Thr Ser Leu Ser Leu Arg Ala Pro Glu
    1025            1030            1035

Thr Val Pro Ser Ala Pro Glu Asn Pro Arg Ile Phe Ile Leu Pro
    1040            1045            1050

Ser Gly Lys Cys Cys Asn Lys Asn Glu Val Val Val Glu Phe Arg
    1055            1060            1065

Trp Asn Lys Pro Lys His Glu Asn Gly Val Leu Thr Lys Phe Glu
    1070            1075            1080

Ile Phe Tyr Asn Ile Ser Asn Gln Ser Ile Thr Asn Lys Thr Cys
    1085            1090            1095

Glu Asp Trp Ile Ala Val Asn Val Thr Pro Ser Val Met Ser Phe
    1100            1105            1110

Gln Leu Glu Gly Met Ser Pro Arg Cys Phe Ile Ala Phe Gln Val
    1115            1120            1125

Arg Ala Phe Thr Ser Lys Gly Pro Gly Pro Tyr Ala Asp Val Val
    1130            1135            1140

Lys Ser Thr Thr Ser Glu Ile Asn Pro Phe Pro His Leu Ile Thr
    1145            1150            1155

Leu Leu Gly Asn Lys Ile Val Phe Leu Asp Met Asp Gln Asn Gln
    1160            1165            1170

Val Val Trp Thr Phe Ser Ala Glu Arg Val Ile Ser Ala Val Cys
    1175            1180            1185

Tyr Thr Ala Asp Asn Glu Met Gly Tyr Tyr Ala Glu Gly Asp Ser
    1190            1195            1200

Leu Phe Leu Leu His Leu His Asn Arg Ser Ser Glu Leu Phe
```

```
              1205                1210                1215

Gln Asp Ser Leu Val Phe Asp Ile Thr Val Ile Thr Ile Asp Trp
              1220                1225                1230

Ile Ser Arg His Leu Tyr Phe Ala Leu Lys Glu Ser Gln Asn Gly
              1235                1240                1245

Met Gln Val Phe Asp Val Asp Leu Glu His Lys Val Lys Tyr Pro
              1250                1255                1260

Arg Glu Val Lys Ile His Asn Arg Asn Ser Thr Ile Ile Ser Phe
              1265                1270                1275

Ser Val Tyr Pro Leu Leu Ser Arg Leu Tyr Trp Thr Glu Val Ser
              1280                1285                1290

Asn Phe Gly Tyr Gln Met Phe Tyr Tyr Ser Ile Ser His Thr
              1295                1300                1305

Leu His Arg Ile Leu Gln Pro Thr Ala Thr Asn Gln Gln Asn Lys
              1310                1315                1320

Arg Asn Gln Cys Ser Cys Asn Val Thr Glu Phe Glu Leu Ser Gly
              1325                1330                1335

Ala Met Ala Ile Asp Thr Ser Asn Leu Glu Lys Pro Leu Ile Tyr
              1340                1345                1350

Phe Ala Lys Ala Gln Glu Ile Trp Ala Met Asp Leu Glu Gly Cys
              1355                1360                1365

Gln Cys Trp Arg Val Ile Thr Val Pro Ala Met Leu Ala Gly Lys
              1370                1375                1380

Thr Leu Val Ser Leu Thr Val Asp Gly Asp Leu Ile Tyr Trp Ile
              1385                1390                1395

Ile Thr Ala Lys Asp Ser Thr Gln Ile Tyr Gln Ala Lys Lys Gly
              1400                1405                1410

Asn Gly Ala Ile Val Ser Gln Val Lys Ala Leu Arg Ser Arg His
              1415                1420                1425

Ile Leu Ala Tyr Ser Ser Val Met Gln Pro Phe Pro Asp Lys Ala
              1430                1435                1440

Phe Leu Ser Leu Ala Ser Asp Thr Val Glu Pro Thr Ile Leu Asn
              1445                1450                1455

Ala Thr Asn Thr Ser Leu Thr Ile Arg Leu Pro Leu Ala Lys Thr
              1460                1465                1470

Asn Leu Thr Trp Tyr Gly Ile Thr Ser Pro Thr Pro Thr Tyr Leu
              1475                1480                1485

Val Tyr Tyr Ala Glu Val Asn Asp Arg Lys Asn Ser Ser Asp Leu
              1490                1495                1500

Lys Tyr Arg Ile Leu Glu Phe Gln Asp Ser Ile Ala Leu Ile Glu
              1505                1510                1515

Asp Leu Gln Pro Phe Ser Thr Tyr Met Ile Gln Ile Ala Val Lys
              1520                1525                1530

Asn Tyr Tyr Ser Asp Pro Leu Glu His Leu Pro Gly Lys Glu
              1535                1540                1545

Ile Trp Gly Lys Thr Lys Asn Gly Val Pro Glu Ala Val Gln Leu
              1550                1555                1560

Ile Asn Thr Thr Val Arg Ser Asp Thr Ser Leu Ile Ile Ser Trp
              1565                1570                1575

Arg Glu Ser His Lys Pro Asn Gly Pro Lys Glu Ser Val Arg Tyr
              1580                1585                1590

Gln Leu Ala Ile Ser His Leu Ala Leu Ile Pro Glu Thr Pro Leu
              1595                1600                1605
```

-continued

Arg Gln Ser Glu Phe Pro Asn Gly Arg Leu Thr Leu Leu Val Thr
1610            1615                1620

Arg Leu Ser Gly Gly Asn Ile Tyr Val Leu Lys Val Leu Ala Cys
1625            1630                1635

His Ser Glu Glu Met Trp Cys Thr Glu Ser His Pro Val Thr Val
1640            1645                1650

Glu Met Phe Asn Thr Pro Glu Lys Pro Tyr Ser Leu Val Pro Glu
1655            1660                1665

Asn Thr Ser Leu Gln Phe Asn Trp Lys Ala Pro Leu Asn Val Asn
1670            1675                1680

Leu Ile Arg Phe Trp Val Glu Leu Gln Lys Trp Lys Tyr Asn Glu
1685            1690                1695

Phe Tyr His Val Lys Thr Ser Cys Ser Gln Gly Pro Ala Tyr Val
1700            1705                1710

Cys Asn Ile Thr Asn Leu Gln Pro Tyr Thr Ser Tyr Asn Val Arg
1715            1720                1725

Val Val Val Val Tyr Lys Thr Gly Glu Asn Ser Thr Ser Leu Pro
1730            1735                1740

Glu Ser Phe Lys Thr Lys Ala Gly Val Pro Asn Lys Pro Gly Ile
1745            1750                1755

Pro Lys Leu Leu Glu Gly Ser Lys Asn Ser Ile Gln Trp Glu Lys
1760            1765                1770

Ala Glu Asp Asn Gly Cys Arg Ile Thr Tyr Tyr Ile Leu Glu Ile
1775            1780                1785

Arg Lys Ser Thr Ser Asn Asn Leu Gln Asn Gln Asn Leu Arg Trp
1790            1795                1800

Lys Met Thr Phe Asn Gly Ser Cys Ser Ser Val Cys Thr Trp Lys
1805            1810                1815

Ser Lys Asn Leu Lys Gly Ile Phe Gln Phe Arg Val Val Ala Ala
1820            1825                1830

Asn Asn Leu Gly Phe Gly Glu Tyr Ser Gly Ile Ser Glu Asn Ile
1835            1840                1845

Ile Leu Val Gly Asp Asp Phe Trp Ile Pro Glu Thr Ser Phe Ile
1850            1855                1860

Leu Thr Ile Ile Val Gly Ile Phe Leu Val Val Thr Ile Pro Leu
1865            1870                1875

Thr Phe Val Trp His Arg Arg Leu Lys Asn Gln Lys Ser Ala Lys
1880            1885                1890

Glu Gly Val Thr Val Leu Ile Asn Glu Asp Lys Glu Leu Ala Glu
1895            1900                1905

Leu Arg Gly Leu Ala Ala Gly Val Gly Leu Ala Asn Ala Cys Tyr
1910            1915                1920

Ala Ile His Thr Leu Pro Thr Gln Glu Glu Ile Glu Asn Leu Pro
1925            1930                1935

Ala Phe Pro Arg Glu Lys Leu Thr Leu Arg Leu Leu Leu Gly Ser
1940            1945                1950

Gly Ala Phe Gly Glu Val Tyr Glu Gly Thr Ala Val Asp Ile Leu
1955            1960                1965

Gly Val Gly Ser Gly Glu Ile Lys Val Ala Val Lys Thr Leu Lys
1970            1975                1980

Lys Gly Ser Thr Asp Gln Glu Lys Ile Glu Phe Leu Lys Glu Ala
1985            1990                1995

His Leu Met Ser Lys Phe Asn His Pro Asn Ile Leu Lys Gln Leu
2000                    2005                2010

Gly Val Cys Leu Leu Asn Glu Pro Gln Tyr Ile Ile Leu Glu Leu
2015                    2020                2025

Met Glu Gly Gly Asp Leu Leu Thr Tyr Leu Arg Lys Ala Arg Met
2030                    2035                2040

Ala Thr Phe Tyr Gly Pro Leu Leu Thr Leu Val Asp Leu Val Asp
2045                    2050                2055

Leu Cys Val Asp Ile Ser Lys Gly Cys Val Tyr Leu Glu Arg Met
2060                    2065                2070

His Phe Ile His Arg Asp Leu Ala Ala Arg Asn Cys Leu Val Ser
2075                    2080                2085

Val Lys Asp Tyr Thr Ser Pro Arg Ile Val Lys Ile Gly Asp Phe
2090                    2095                2100

Gly Leu Ala Arg Asp Ile Tyr Lys Asn Asp Tyr Tyr Arg Lys Arg
2105                    2110                2115

Gly Glu Gly Leu Leu Pro Val Arg Trp Met Ala Pro Glu Ser Leu
2120                    2125                2130

Met Asp Gly Ile Phe Thr Thr Gln Ser Asp Val Trp Ser Phe Gly
2135                    2140                2145

Ile Leu Ile Trp Glu Ile Leu Thr Leu Gly His Gln Pro Tyr Pro
2150                    2155                2160

Ala His Ser Asn Leu Asp Val Leu Asn Tyr Val Gln Thr Gly Gly
2165                    2170                2175

Arg Leu Glu Pro Pro Arg Asn Cys Pro Asp Asp Leu Trp Asn Leu
2180                    2185                2190

Met Thr Gln Cys Trp Ala Gln Glu Pro Asp Gln Arg Pro Thr Phe
2195                    2200                2205

His Arg Ile Gln Asp Gln Leu Gln Leu Phe Arg Asn Phe Phe Leu
2210                    2215                2220

Asn Ser Ile Tyr Lys Ser Arg Asp Glu Ala Asn Asn Ser Gly Val
2225                    2230                2235

Ile Asn Glu Ser Phe Glu Gly Glu Asp Gly Asp Val Ile Cys Leu
2240                    2245                2250

Asn Ser Asp Asp Ile Met Pro Val Ala Leu Met Glu Thr Lys Asn
2255                    2260                2265

Arg Glu Gly Leu Asn Tyr Met Val Leu Ala Thr Glu Cys Gly Gln
2270                    2275                2280

Gly Glu Glu Lys Ser Glu Gly Pro Leu Gly Ser Gln Glu Ser Glu
2285                    2290                2295

Ser Cys Gly Leu Arg Lys Glu Lys Glu Pro His Ala Asp Lys
2300                    2305                2310

Asp Phe Cys Gln Glu Lys Gln Val Ala Tyr Cys Pro Ser Gly Lys
2315                    2320                2325

Pro Glu Gly Leu Asn Tyr Ala Cys Leu Thr His Ser Gly Tyr Gly
2330                    2335                2340

Asp Gly Ser Asp
2345

<210> SEQ ID NO 5

<400> SEQUENCE: 5

000

<210> SEQ ID NO 6
<211> LENGTH: 852
<212> TYPE: PRT
<213> ORGANISM: Homo sapiens
<220> FEATURE:
<221> NAME/KEY: MISC_FEATURE
<222> LOCATION: (1)..(852)
<223> OTHER INFORMATION: lysine-specific histone demethylase 1A isoform
      b [Homo sapiens]; NCBI Reference Sequence: NP_055828.2

<400> SEQUENCE: 6

Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Arg Asn Ala Lys
    130                 135                 140

Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Val Glu Gly
                165                 170                 175

Ala Ala Phe Gln Ser Arg Leu Pro His Asp Arg Met Thr Ser Gln Glu
            180                 185                 190

Ala Ala Cys Phe Pro Asp Ile Ile Ser Gly Pro Gln Gln Thr Gln Lys
        195                 200                 205

Val Phe Leu Phe Ile Arg Asn Arg Thr Leu Gln Leu Trp Leu Asp Asn
    210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
                245                 250                 255

Glu Arg His Gly Leu Ile Asn Phe Gly Ile Tyr Lys Arg Ile Lys Pro
            260                 265                 270

Leu Pro Thr Lys Lys Thr Gly Lys Val Ile Ile Ile Gly Ser Gly Val
        275                 280                 285

Ser Gly Leu Ala Ala Ala Arg Gln Leu Gln Ser Phe Gly Met Asp Val
    290                 295                 300

Thr Leu Leu Glu Ala Arg Asp Arg Val Gly Gly Arg Val Ala Thr Phe
305                 310                 315                 320

Arg Lys Gly Asn Tyr Val Ala Asp Leu Gly Ala Met Val Val Thr Gly
                325                 330                 335

Leu Gly Gly Asn Pro Met Ala Val Val Ser Lys Gln Val Asn Met Glu
            340                 345                 350

```
Leu Ala Lys Ile Lys Gln Lys Cys Pro Leu Tyr Glu Ala Asn Gly Gln
        355                 360                 365
Ala Val Pro Lys Glu Lys Asp Glu Met Val Glu Gln Glu Phe Asn Arg
    370                 375                 380
Leu Leu Glu Ala Thr Ser Tyr Leu Ser His Gln Leu Asp Phe Asn Val
385                 390                 395                 400
Leu Asn Asn Lys Pro Val Ser Leu Gly Gln Ala Leu Glu Val Val Ile
                405                 410                 415
Gln Leu Gln Glu Lys His Val Lys Asp Glu Gln Ile Glu His Trp Lys
            420                 425                 430
Lys Ile Val Lys Thr Gln Glu Glu Leu Lys Glu Leu Leu Asn Lys Met
        435                 440                 445
Val Asn Leu Lys Glu Lys Ile Lys Glu Leu His Gln Gln Tyr Lys Glu
    450                 455                 460
Ala Ser Glu Val Lys Pro Pro Arg Asp Ile Thr Ala Glu Phe Leu Val
465                 470                 475                 480
Lys Ser Lys His Arg Asp Leu Thr Ala Leu Cys Lys Glu Tyr Asp Glu
                485                 490                 495
Leu Ala Glu Thr Gln Gly Lys Leu Glu Glu Lys Leu Gln Glu Leu Glu
            500                 505                 510
Ala Asn Pro Pro Ser Asp Val Tyr Leu Ser Ser Arg Asp Arg Gln Ile
        515                 520                 525
Leu Asp Trp His Phe Ala Asn Leu Glu Phe Ala Asn Ala Thr Pro Leu
    530                 535                 540
Ser Thr Leu Ser Leu Lys His Trp Asp Gln Asp Asp Asp Phe Glu Phe
545                 550                 555                 560
Thr Gly Ser His Leu Thr Val Arg Asn Gly Tyr Ser Cys Val Pro Val
                565                 570                 575
Ala Leu Ala Glu Gly Leu Asp Ile Lys Leu Asn Thr Ala Val Arg Gln
            580                 585                 590
Val Arg Tyr Thr Ala Ser Gly Cys Glu Val Ile Ala Val Asn Thr Arg
        595                 600                 605
Ser Thr Ser Gln Thr Phe Ile Tyr Lys Cys Asp Ala Val Leu Cys Thr
    610                 615                 620
Leu Pro Leu Gly Val Leu Lys Gln Gln Pro Pro Ala Val Gln Phe Val
625                 630                 635                 640
Pro Pro Leu Pro Glu Trp Lys Thr Ser Ala Val Gln Arg Met Gly Phe
                645                 650                 655
Gly Asn Leu Asn Lys Val Val Leu Cys Phe Asp Arg Val Phe Trp Asp
            660                 665                 670
Pro Ser Val Asn Leu Phe Gly His Val Gly Ser Thr Thr Ala Ser Arg
        675                 680                 685
Gly Glu Leu Phe Leu Phe Trp Asn Leu Tyr Lys Ala Pro Ile Leu Leu
    690                 695                 700
Ala Leu Val Ala Gly Glu Ala Gly Ile Met Glu Asn Ile Ser Asp Asp
705                 710                 715                 720
Asp Val Ile Val Gly Arg Cys Leu Ala Ile Leu Lys Gly Ile Phe Gly
                725                 730                 735
Ser Ser Ala Val Pro Gln Pro Lys Glu Thr Val Val Ser Arg Trp Arg
            740                 745                 750
Ala Asp Pro Trp Ala Arg Gly Ser Tyr Ser Tyr Val Ala Ala Gly Ser
        755                 760                 765
Ser Gly Asn Asp Tyr Asp Leu Met Ala Gln Pro Ile Thr Pro Gly Pro
```

```
            770                 775                 780
Ser Ile Pro Gly Ala Pro Gln Pro Ile Pro Arg Leu Phe Phe Ala Gly
785                 790                 795                 800

Glu His Thr Ile Arg Asn Tyr Pro Ala Thr Val His Gly Ala Leu Leu
                805                 810                 815

Ser Gly Leu Arg Glu Ala Gly Arg Ile Ala Asp Gln Phe Leu Gly Ala
            820                 825                 830

Met Tyr Thr Leu Pro Arg Gln Ala Thr Pro Gly Val Pro Ala Gln Gln
        835                 840                 845

Ser Pro Ser Met
        850

<210> SEQ ID NO 7

<400> SEQUENCE: 7

000

<210> SEQ ID NO 8
<211> LENGTH: 659
<212> TYPE: PRT
<213> ORGANISM: Homo sapiens
<220> FEATURE:
<221> NAME/KEY: MISC_FEATURE
<222> LOCATION: (1)..(659)
<223> OTHER INFORMATION: tyrosine-protein kinase BTK isoform 1 [Homo
      sapiens]; NCBI Reference Sequence: NP_000052.1

<400> SEQUENCE: 8

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220
```

```
Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
            245                 250                 255

Lys Asn Gly Gln Glu Gly Tyr Ile Pro Ser Asn Tyr Val Thr Glu Ala
        260                 265                 270

Glu Asp Ser Ile Glu Met Tyr Glu Trp Tyr Ser Lys His Met Thr Arg
    275                 280                 285

Ser Gln Ala Glu Gln Leu Leu Lys Gln Glu Gly Lys Glu Gly Gly Phe
290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
            325                 330                 335

Cys Ser Thr Pro Gln Ser Gln Tyr Tyr Leu Ala Glu Lys His Leu Phe
        340                 345                 350

Ser Thr Ile Pro Glu Leu Ile Asn Tyr His Gln His Asn Ser Ala Gly
    355                 360                 365

Leu Ile Ser Arg Leu Lys Tyr Pro Val Ser Gln Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
            405                 410                 415

Lys Tyr Gly Lys Trp Arg Gly Gln Tyr Asp Val Ala Ile Lys Met Ile
        420                 425                 430

Lys Glu Gly Ser Met Ser Glu Asp Glu Phe Ile Glu Glu Ala Lys Val
    435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
            485                 490                 495

Gln Leu Leu Glu Met Cys Lys Asp Val Cys Glu Ala Met Glu Tyr Leu
        500                 505                 510

Glu Ser Lys Gln Phe Leu His Arg Asp Leu Ala Ala Arg Asn Cys Leu
    515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
            565                 570                 575

Lys Ser Asp Ile Trp Ala Phe Gly Val Leu Met Trp Glu Ile Tyr Ser
        580                 585                 590

Leu Gly Lys Met Pro Tyr Glu Arg Phe Thr Asn Ser Glu Thr Ala Glu
    595                 600                 605

His Ile Ala Gln Gly Leu Arg Leu Tyr Arg Pro His Leu Ala Ser Glu
610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
```

645                 650                 655

Glu Glu Ser

<210> SEQ ID NO 9

<400> SEQUENCE: 9

000

<210> SEQ ID NO 10
<211> LENGTH: 732
<212> TYPE: PRT
<213> ORGANISM: Homo sapiens
<220> FEATURE:
<221> NAME/KEY: MISC_FEATURE
<222> LOCATION: (1)..(732)
<223> OTHER INFORMATION: X-ray repair cross-complementing protein 5
      [Homo sapiens]; NCBI Reference Sequence: NP_066964.1

<400> SEQUENCE: 10

Met Val Arg Ser Gly Asn Lys Ala Ala Val Val Leu Cys Met Asp Val
1               5                   10                  15

Gly Phe Thr Met Ser Asn Ser Ile Pro Gly Ile Glu Ser Pro Phe Glu
            20                  25                  30

Gln Ala Lys Lys Val Ile Thr Met Phe Val Gln Arg Gln Val Phe Ala
        35                  40                  45

Glu Asn Lys Asp Glu Ile Ala Leu Val Leu Phe Gly Thr Asp Gly Thr
    50                  55                  60

Asp Asn Pro Leu Ser Gly Gly Asp Gln Tyr Gln Asn Ile Thr Val His
65                  70                  75                  80

Arg His Leu Met Leu Pro Asp Phe Asp Leu Leu Glu Asp Ile Glu Ser
                85                  90                  95

Lys Ile Gln Pro Gly Ser Gln Ala Asp Phe Leu Asp Ala Leu Ile
            100                 105                 110

Val Ser Met Asp Val Ile Gln His Glu Thr Ile Gly Lys Lys Phe Glu
        115                 120                 125

Lys Arg His Ile Glu Ile Phe Thr Asp Leu Ser Ser Arg Phe Ser Lys
    130                 135                 140

Ser Gln Leu Asp Ile Ile Ile His Ser Leu Lys Lys Cys Asp Ile Ser
145                 150                 155                 160

Leu Gln Phe Phe Leu Pro Phe Ser Leu Gly Lys Glu Asp Gly Ser Gly
                165                 170                 175

Asp Arg Gly Asp Gly Pro Phe Arg Leu Gly Gly His Gly Pro Ser Phe
            180                 185                 190

Pro Leu Lys Gly Ile Thr Glu Gln Gln Lys Glu Gly Leu Glu Ile Val
        195                 200                 205

Lys Met Val Met Ile Ser Leu Glu Gly Glu Asp Gly Leu Asp Glu Ile
    210                 215                 220

Tyr Ser Phe Ser Glu Ser Leu Arg Lys Leu Cys Val Phe Lys Lys Ile
225                 230                 235                 240

Glu Arg His Ser Ile His Trp Pro Cys Arg Leu Thr Ile Gly Ser Asn
                245                 250                 255

Leu Ser Ile Arg Ile Ala Ala Tyr Lys Ser Ile Leu Gln Glu Arg Val
            260                 265                 270

Lys Lys Thr Trp Thr Val Val Asp Ala Lys Thr Leu Lys Lys Glu Asp
        275                 280                 285

Ile Gln Lys Glu Thr Val Tyr Cys Leu Asn Asp Asp Asp Glu Thr Glu

```
                290                 295                 300
Val Leu Lys Glu Asp Ile Ile Gln Gly Phe Arg Tyr Gly Ser Asp Ile
305                 310                 315                 320

Val Pro Phe Ser Lys Val Asp Glu Glu Gln Met Lys Tyr Lys Ser Glu
                325                 330                 335

Gly Lys Cys Phe Ser Val Leu Gly Phe Cys Lys Ser Ser Gln Val Gln
                340                 345                 350

Arg Arg Phe Phe Met Gly Asn Gln Val Leu Lys Val Phe Ala Ala Arg
                355                 360                 365

Asp Asp Glu Ala Ala Val Ala Leu Ser Ser Leu Ile His Ala Leu
        370                 375                 380

Asp Asp Leu Asp Met Val Ala Ile Val Arg Tyr Ala Tyr Asp Lys Arg
385                 390                 395                 400

Ala Asn Pro Gln Val Gly Val Ala Phe Pro His Ile Lys His Asn Tyr
                405                 410                 415

Glu Cys Leu Val Tyr Val Gln Leu Pro Phe Met Glu Asp Leu Arg Gln
                420                 425                 430

Tyr Met Phe Ser Ser Leu Lys Asn Ser Lys Tyr Ala Pro Thr Glu
        435                 440                 445

Ala Gln Leu Asn Ala Val Asp Ala Leu Ile Asp Ser Met Ser Leu Ala
        450                 455                 460

Lys Lys Asp Glu Lys Thr Asp Thr Leu Glu Asp Leu Phe Pro Thr Thr
465                 470                 475                 480

Lys Ile Pro Asn Pro Arg Phe Gln Arg Leu Phe Gln Cys Leu Leu His
                485                 490                 495

Arg Ala Leu His Pro Arg Glu Pro Leu Pro Ile Gln Gln His Ile
        500                 505                 510

Trp Asn Met Leu Asn Pro Pro Ala Glu Val Thr Thr Lys Ser Gln Ile
        515                 520                 525

Pro Leu Ser Lys Ile Lys Thr Leu Phe Pro Leu Ile Glu Ala Lys Lys
        530                 535                 540

Lys Asp Gln Val Thr Ala Gln Glu Ile Phe Gln Asp Asn His Glu Asp
545                 550                 555                 560

Gly Pro Thr Ala Lys Lys Leu Lys Thr Glu Gln Gly Ala His Phe
        565                 570                 575

Ser Val Ser Ser Leu Ala Glu Gly Ser Val Thr Ser Val Gly Ser Val
        580                 585                 590

Asn Pro Ala Glu Asn Phe Arg Val Leu Val Lys Gln Lys Lys Ala Ser
        595                 600                 605

Phe Glu Glu Ala Ser Asn Gln Leu Ile Asn His Ile Glu Gln Phe Leu
610                 615                 620

Asp Thr Asn Glu Thr Pro Tyr Phe Met Lys Ser Ile Asp Cys Ile Arg
625                 630                 635                 640

Ala Phe Arg Glu Glu Ala Ile Lys Phe Ser Glu Glu Gln Arg Phe Asn
                645                 650                 655

Asn Phe Leu Lys Ala Leu Gln Glu Lys Val Glu Ile Lys Gln Leu Asn
                660                 665                 670

His Phe Trp Glu Ile Val Val Gln Asp Gly Ile Thr Leu Ile Thr Lys
                675                 680                 685

Glu Glu Ala Ser Gly Ser Ser Val Thr Ala Glu Glu Ala Lys Lys Phe
        690                 695                 700

Leu Ala Pro Lys Asp Lys Pro Ser Gly Asp Thr Ala Ala Val Phe Glu
705                 710                 715                 720
```

```
Glu Gly Gly Asp Val Asp Asp Leu Leu Asp Met Ile
                    725             730
```

<210> SEQ ID NO 11

<400> SEQUENCE: 11

000

<210> SEQ ID NO 12
<211> LENGTH: 609
<212> TYPE: PRT
<213> ORGANISM: Homo sapiens
<220> FEATURE:
<221> NAME/KEY: MISC_FEATURE
<222> LOCATION: (1)..(609)
<223> OTHER INFORMATION: X-ray repair cross-complementing protein 6
      isoform 1 [Homo sapiens]; NCBI Reference Sequence: NP_001460.1

<400> SEQUENCE: 12

```
Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Val Val Phe Tyr Gly Thr Glu Lys Asp Lys Asn Ser
                85                  90                  95

Val Asn Phe Lys Asn Ile Tyr Val Leu Gln Glu Leu Asp Asn Pro Gly
            100                 105                 110

Ala Lys Arg Ile Leu Glu Leu Asp Gln Phe Lys Gly Gln Gln Gly Gln
        115                 120                 125

Lys Arg Phe Gln Asp Met Met Gly His Gly Ser Asp Tyr Ser Leu Ser
    130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
            180                 185                 190

Leu Arg Asp Thr Gly Ile Phe Leu Asp Leu Met His Leu Lys Lys Pro
        195                 200                 205

Gly Gly Phe Asp Ile Ser Leu Phe Tyr Arg Asp Ile Ile Ser Ile Ala
    210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
            260                 265                 270

Ile Tyr Asn Leu Val Gln Lys Ala Leu Lys Pro Pro Pro Ile Lys Leu
        275                 280                 285

Tyr Arg Glu Thr Asn Glu Pro Val Lys Thr Lys Thr Arg Thr Phe Asn
```

```
                290                 295                 300
Thr Ser Thr Gly Gly Leu Leu Pro Ser Asp Thr Lys Arg Ser Gln
305                 310                 315                 320

Ile Tyr Gly Ser Arg Gln Ile Ile Leu Glu Lys Glu Thr Glu Glu
                325                 330                 335

Leu Lys Arg Phe Asp Asp Pro Gly Leu Met Leu Met Gly Phe Lys Pro
                340                 345                 350

Leu Val Leu Leu Lys Lys His His Tyr Leu Arg Pro Ser Leu Phe Val
                355                 360                 365

Tyr Pro Glu Glu Ser Leu Val Ile Gly Ser Ser Thr Leu Phe Ser Ala
                370                 375                 380

Leu Leu Ile Lys Cys Leu Glu Lys Glu Val Ala Ala Leu Cys Arg Tyr
385                 390                 395                 400

Thr Pro Arg Arg Asn Ile Pro Pro Tyr Phe Val Ala Leu Val Pro Gln
                405                 410                 415

Glu Glu Glu Leu Asp Asp Gln Lys Ile Gln Val Thr Pro Pro Gly Phe
                420                 425                 430

Gln Leu Val Phe Leu Pro Phe Ala Asp Asp Lys Arg Lys Met Pro Phe
                435                 440                 445

Thr Glu Lys Ile Met Ala Thr Pro Glu Gln Val Gly Lys Met Lys Ala
                450                 455                 460

Ile Val Glu Lys Leu Arg Phe Thr Tyr Arg Ser Asp Ser Phe Glu Asn
465                 470                 475                 480

Pro Val Leu Gln Gln His Phe Arg Asn Leu Glu Ala Leu Ala Leu Asp
                485                 490                 495

Leu Met Glu Pro Glu Gln Ala Val Asp Leu Thr Leu Pro Lys Val Glu
                500                 505                 510

Ala Met Asn Lys Arg Leu Gly Ser Leu Val Asp Glu Phe Lys Glu Leu
                515                 520                 525

Val Tyr Pro Pro Asp Tyr Asn Pro Glu Gly Lys Val Thr Lys Arg Lys
                530                 535                 540

His Asp Asn Glu Gly Ser Gly Ser Lys Arg Pro Lys Val Glu Tyr Ser
545                 550                 555                 560

Glu Glu Glu Leu Lys Thr His Ile Ser Lys Gly Thr Leu Gly Lys Phe
                565                 570                 575

Thr Val Pro Met Leu Lys Glu Ala Cys Arg Ala Tyr Gly Leu Lys Ser
                580                 585                 590

Gly Leu Lys Lys Gln Glu Leu Leu Glu Ala Leu Thr Lys His Phe Gln
                595                 600                 605

Asp

<210> SEQ ID NO 13

<400> SEQUENCE: 13

000

<210> SEQ ID NO 14
<211> LENGTH: 759
<212> TYPE: PRT
<213> ORGANISM: Homo sapiens
<220> FEATURE:
<221> NAME/KEY: MISC_FEATURE
<222> LOCATION: (1)..(759)
<223> OTHER INFORMATION: cullin-4A isoform 1 [Homo sapiens];  NCBI
      Reference Sequence: NP_001008895.1
```

<400> SEQUENCE: 14

```
Met Ala Asp Glu Ala Pro Arg Lys Gly Ser Phe Ser Ala Leu Val Gly
1               5                   10                  15

Arg Thr Asn Gly Leu Thr Lys Pro Ala Ala Leu Ala Ala Ala Pro Ala
            20                  25                  30

Lys Pro Gly Gly Ala Gly Gly Ser Lys Lys Leu Val Ile Lys Asn Phe
        35                  40                  45

Arg Asp Arg Pro Arg Leu Pro Asp Asn Tyr Thr Gln Asp Thr Trp Arg
    50                  55                  60

Lys Leu His Glu Ala Val Arg Ala Val Gln Ser Ser Thr Ser Ile Arg
65                  70                  75                  80

Tyr Asn Leu Glu Glu Leu Tyr Gln Ala Val Glu Asn Leu Cys Ser His
                85                  90                  95

Lys Val Ser Pro Met Leu Tyr Lys Gln Leu Arg Gln Ala Cys Glu Asp
            100                 105                 110

His Val Gln Ala Gln Ile Leu Pro Phe Arg Glu Asp Ser Leu Asp Ser
        115                 120                 125

Val Leu Phe Leu Lys Lys Ile Asn Thr Cys Trp Gln Asp His Cys Arg
    130                 135                 140

Gln Met Ile Met Ile Arg Ser Ile Phe Leu Phe Leu Asp Arg Thr Tyr
145                 150                 155                 160

Val Leu Gln Asn Ser Thr Leu Pro Ser Ile Trp Asp Met Gly Leu Glu
                165                 170                 175

Leu Phe Arg Thr His Ile Ile Ser Asp Lys Met Val Gln Ser Lys Thr
            180                 185                 190

Ile Asp Gly Ile Leu Leu Leu Ile Glu Arg Glu Arg Ser Gly Glu Ala
        195                 200                 205

Val Asp Arg Ser Leu Leu Arg Ser Leu Leu Gly Met Leu Ser Asp Leu
    210                 215                 220

Gln Val Tyr Lys Asp Ser Phe Glu Leu Lys Phe Leu Glu Glu Thr Asn
225                 230                 235                 240

Cys Leu Tyr Ala Ala Glu Gly Gln Arg Leu Met Gln Glu Arg Glu Val
                245                 250                 255

Pro Glu Tyr Leu Asn His Val Ser Lys Arg Leu Glu Glu Gly Asp
            260                 265                 270

Arg Val Ile Thr Tyr Leu Asp His Ser Thr Gln Lys Pro Leu Ile Ala
        275                 280                 285

Cys Val Glu Lys Gln Leu Leu Gly Glu His Leu Thr Ala Ile Leu Gln
    290                 295                 300

Lys Gly Leu Asp His Leu Leu Asp Glu Asn Arg Val Pro Asp Leu Ala
305                 310                 315                 320

Gln Met Tyr Gln Leu Phe Ser Arg Val Arg Gly Gly Gln Gln Ala Leu
                325                 330                 335

Leu Gln His Trp Ser Glu Tyr Ile Lys Thr Phe Gly Thr Ala Ile Val
            340                 345                 350

Ile Asn Pro Glu Lys Asp Lys Asp Met Val Gln Asp Leu Leu Asp Phe
        355                 360                 365

Lys Asp Lys Val Asp His Val Ile Glu Val Cys Phe Gln Lys Asn Glu
    370                 375                 380

Arg Phe Val Asn Leu Met Lys Glu Ser Phe Glu Thr Phe Ile Asn Lys
385                 390                 395                 400

Arg Pro Asn Lys Pro Ala Glu Leu Ile Ala Lys His Val Asp Ser Lys
                405                 410                 415
```

-continued

Leu Arg Ala Gly Asn Lys Glu Ala Thr Asp Glu Leu Glu Arg Thr
            420                 425                 430

Leu Asp Lys Ile Met Ile Leu Phe Arg Phe Ile His Gly Lys Asp Val
            435                 440                 445

Phe Glu Ala Phe Tyr Lys Asp Leu Ala Lys Arg Leu Leu Val Gly
450                 455                 460

Lys Ser Ala Ser Val Asp Ala Glu Lys Ser Met Leu Ser Lys Leu Lys
465                 470                 475                 480

His Glu Cys Gly Ala Ala Phe Thr Ser Lys Leu Glu Gly Met Phe Lys
                485                 490                 495

Asp Met Glu Leu Ser Lys Asp Ile Met Val His Phe Lys Gln His Met
            500                 505                 510

Gln Asn Gln Ser Asp Ser Gly Pro Ile Asp Leu Thr Val Asn Ile Leu
        515                 520                 525

Thr Met Gly Tyr Trp Pro Thr Tyr Thr Pro Met Glu Val His Leu Thr
530                 535                 540

Pro Glu Met Ile Lys Leu Gln Glu Val Phe Lys Ala Phe Tyr Leu Gly
545                 550                 555                 560

Lys His Ser Gly Arg Lys Leu Gln Trp Gln Thr Thr Leu Gly His Ala
                565                 570                 575

Val Leu Lys Ala Glu Phe Lys Gly Lys Lys Glu Phe Gln Val Ser
            580                 585                 590

Leu Phe Gln Thr Leu Val Leu Leu Met Phe Asn Glu Gly Asp Gly Phe
        595                 600                 605

Ser Phe Glu Glu Ile Lys Met Ala Thr Gly Ile Glu Asp Ser Glu Leu
            610                 615                 620

Arg Arg Thr Leu Gln Ser Leu Ala Cys Gly Lys Ala Arg Val Leu Ile
625                 630                 635                 640

Lys Ser Pro Lys Gly Lys Glu Val Glu Asp Gly Asp Lys Phe Ile Phe
                645                 650                 655

Asn Gly Glu Phe Lys His Lys Leu Phe Arg Ile Lys Ile Asn Gln Ile
            660                 665                 670

Gln Met Lys Glu Thr Val Glu Glu Gln Val Ser Thr Thr Glu Arg Val
        675                 680                 685

Phe Gln Asp Arg Gln Tyr Gln Ile Asp Ala Ala Ile Val Arg Ile Met
690                 695                 700

Lys Met Arg Lys Thr Leu Gly His Asn Leu Leu Val Ser Glu Leu Tyr
705                 710                 715                 720

Asn Gln Leu Lys Phe Pro Val Lys Pro Gly Asp Leu Lys Lys Arg Ile
                725                 730                 735

Glu Ser Leu Ile Asp Arg Asp Tyr Met Glu Arg Asp Lys Asp Asn Pro
            740                 745                 750

Asn Gln Tyr His Tyr Val Ala
        755

<210> SEQ ID NO 15

<400> SEQUENCE: 15

000

<210> SEQ ID NO 16
<211> LENGTH: 184
<212> TYPE: PRT
<213> ORGANISM: Homo sapiens
<220> FEATURE:
<221> NAME/KEY: MISC_FEATURE
<222> LOCATION: (1)..(184)
<223> OTHER INFORMATION: U3 small nucleolar ribonucleoprotein protein
    IMP3 [Homo sapiens]; NCBI Reference Sequence: NP_060755.1

<400> SEQUENCE: 16

Met Val Arg Lys Leu Lys Phe His Glu Gln Lys Leu Leu Lys Gln Val
1               5                   10                  15

Asp Phe Leu Asn Trp Glu Val Thr Asp His Asn Leu His Glu Leu Arg
            20                  25                  30

Val Leu Arg Arg Tyr Arg Leu Gln Arg Arg Glu Asp Tyr Thr Arg Tyr
        35                  40                  45

Asn Gln Leu Ser Arg Ala Val Arg Glu Leu Ala Arg Arg Leu Arg Asp
    50                  55                  60

Leu Pro Glu Arg Asp Gln Phe Arg Val Arg Ala Ser Ala Ala Leu Leu
65                  70                  75                  80

Asp Lys Leu Tyr Ala Leu Gly Leu Val Pro Thr Arg Gly Ser Leu Glu
                85                  90                  95

Leu Cys Asp Phe Val Thr Ala Ser Ser Phe Cys Arg Arg Arg Leu Pro
            100                 105                 110

Thr Val Leu Leu Lys Leu Arg Met Ala Gln His Leu Gln Ala Ala Val
        115                 120                 125

Ala Phe Val Glu Gln Gly His Val Arg Val Gly Pro Asp Val Val Thr
    130                 135                 140

Asp Pro Ala Phe Leu Val Thr Arg Ser Met Glu Asp Phe Val Thr Trp
145                 150                 155                 160

Val Asp Ser Ser Lys Ile Lys Arg His Val Leu Glu Tyr Asn Glu Glu
                165                 170                 175

Arg Asp Asp Phe Asp Leu Glu Ala
            180

<210> SEQ ID NO 17

<400> SEQUENCE: 17

000

<210> SEQ ID NO 18
<211> LENGTH: 105
<212> TYPE: PRT
<213> ORGANISM: Homo sapiens
<220> FEATURE:
<221> NAME/KEY: MISC_FEATURE
<222> LOCATION: (1)..(105)
<223> OTHER INFORMATION: thioredoxin isoform 1 [Homo sapiens]; NCBI
    Reference Sequence: NP_003320.2

<400> SEQUENCE: 18

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Cys Gln Asp
    50                  55                  60

Val Ala Ser Glu Cys Glu Val Lys Cys Met Pro Thr Phe Gln Phe Phe
65                  70                  75                  80

```
Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 19

<400> SEQUENCE: 19

000

<210> SEQ ID NO 20
<211> LENGTH: 300
<212> TYPE: PRT
<213> ORGANISM: Homo sapiens
<220> FEATURE:
<221> NAME/KEY: MISC_FEATURE
<222> LOCATION: (1)..(300)
<223> OTHER INFORMATION: dnaJ homolog subfamily A member 3,
      mitochondrial isoform 3 [Homo sapiens]; NCBI Reference Sequence:
      NP_001273445.1

<400> SEQUENCE: 20

Met Ala Glu Pro Gln Ala Glu Arg Pro Arg Leu Cys Val Phe Pro Asp
1               5                   10                  15

Leu Leu Arg Pro Pro Ser Ala Ala Asp Ile Glu Thr Trp Cys Gln Pro
            20                  25                  30

Tyr Arg Lys Ile Phe Gly Glu Phe Ser Ser Ser Phe Gly Asp Phe
        35                  40                  45

Gln Thr Val Phe Asp Gln Pro Gln Glu Tyr Phe Met Glu Leu Thr Phe
    50                  55                  60

Asn Gln Ala Ala Lys Gly Val Asn Lys Glu Phe Thr Val Asn Ile Met
65                  70                  75                  80

Asp Thr Cys Glu Arg Cys Asn Gly Lys Gly Asn Glu Pro Gly Thr Lys
                85                  90                  95

Val Gln His Cys His Tyr Cys Gly Gly Ser Gly Met Glu Thr Ile Asn
            100                 105                 110

Thr Gly Pro Phe Val Met Arg Ser Thr Cys Arg Arg Cys Gly Gly Arg
        115                 120                 125

Gly Ser Ile Ile Ile Ser Pro Cys Val Val Cys Arg Gly Ala Gly Gln
    130                 135                 140

Ala Lys Gln Lys Lys Arg Val Met Ile Pro Val Pro Ala Gly Val Glu
145                 150                 155                 160

Asp Gly Gln Thr Val Arg Met Pro Val Gly Lys Arg Glu Ile Phe Ile
                165                 170                 175

Thr Phe Arg Val Gln Lys Ser Pro Val Phe Arg Arg Asp Gly Ala Asp
            180                 185                 190

Ile His Ser Asp Leu Phe Ile Ser Ile Ala Gln Ala Leu Leu Gly Gly
        195                 200                 205

Thr Ala Arg Ala Gln Gly Leu Tyr Glu Thr Ile Asn Val Thr Ile Pro
    210                 215                 220

Pro Gly Thr Gln Thr Asp Gln Lys Ile Arg Met Gly Gly Lys Gly Ile
225                 230                 235                 240

Pro Arg Ile Asn Ser Tyr Gly Tyr Gly Asp His Tyr Ile His Ile Lys
                245                 250                 255

Ile Arg Val Pro Lys Arg Leu Thr Ser Arg Gln Gln Ser Leu Ile Leu
            260                 265                 270

Ser Tyr Ala Glu Asp Glu Thr Asp Val Glu Gly Thr Val Asn Gly Val
```

```
                    275                 280                 285

Thr Leu Thr Ser Ser Gly Lys Arg Ser Thr Gly Asn
    290                 295                 300

<210> SEQ ID NO 21

<400> SEQUENCE: 21

000

<210> SEQ ID NO 22
<211> LENGTH: 398
<212> TYPE: PRT
<213> ORGANISM: Homo sapiens
<220> FEATURE:
<221> NAME/KEY: MISC_FEATURE
<222> LOCATION: (1)..(398)
<223> OTHER INFORMATION: 28S ribosomal protein S29, mitochondrial
      isoform 1 [Homo sapiens]; NCBI Reference Sequence: NP_004623.1

<400> SEQUENCE: 22

Met Met Leu Lys Gly Ile Thr Arg Leu Ile Ser Arg Ile His Lys Leu
1               5                   10                  15

Asp Pro Gly Arg Phe Leu His Met Gly Thr Gln Ala Arg Gln Ser Ile
            20                  25                  30

Ala Ala His Leu Asp Asn Gln Val Pro Val Glu Ser Pro Arg Ala Ile
        35                  40                  45

Ser Arg Thr Asn Glu Asn Asp Pro Ala Lys His Gly Asp Gln His Glu
    50                  55                  60

Gly Gln His Tyr Asn Ile Ser Pro Gln Asp Leu Glu Thr Val Phe Pro
65                  70                  75                  80

His Gly Leu Pro Pro Arg Phe Val Met Gln Val Lys Thr Phe Ser Glu
                85                  90                  95

Ala Cys Leu Met Val Arg Lys Pro Ala Leu Glu Leu Leu His Tyr Leu
            100                 105                 110

Lys Asn Thr Ser Phe Ala Tyr Pro Ala Ile Arg Tyr Leu Leu Tyr Gly
        115                 120                 125

Glu Lys Gly Thr Gly Lys Thr Leu Ser Leu Cys His Val Ile His Phe
    130                 135                 140

Cys Ala Lys Gln Asp Trp Leu Ile Leu His Ile Pro Asp Ala His Leu
145                 150                 155                 160

Trp Val Lys Asn Cys Arg Asp Leu Leu Gln Ser Ser Tyr Asn Lys Gln
                165                 170                 175

Arg Phe Asp Gln Pro Leu Glu Ala Ser Thr Trp Leu Lys Asn Phe Lys
            180                 185                 190

Thr Thr Asn Glu Arg Phe Leu Asn Gln Ile Lys Val Gln Glu Lys Tyr
        195                 200                 205

Val Trp Asn Lys Arg Glu Ser Thr Glu Lys Gly Ser Pro Leu Gly Glu
    210                 215                 220

Val Val Glu Gln Gly Ile Thr Arg Val Arg Asn Ala Thr Asp Ala Val
225                 230                 235                 240

Gly Ile Val Leu Lys Glu Leu Lys Arg Gln Ser Ser Leu Gly Met Phe
                245                 250                 255

His Leu Leu Val Ala Val Asp Gly Ile Asn Ala Leu Trp Gly Arg Thr
            260                 265                 270

Thr Leu Lys Arg Glu Asp Lys Ser Pro Ile Ala Pro Glu Glu Leu Ala
        275                 280                 285
```

```
Leu Val His Asn Leu Arg Lys Met Met Lys Asn Asp Trp His Gly Gly
    290                 295                 300

Ala Ile Val Ser Ala Leu Ser Gln Thr Gly Ser Leu Phe Lys Pro Arg
305                 310                 315                 320

Lys Ala Tyr Leu Pro Gln Glu Leu Leu Gly Lys Glu Gly Phe Asp Ala
                325                 330                 335

Leu Asp Pro Phe Ile Pro Ile Leu Val Ser Asn Tyr Asn Pro Lys Glu
            340                 345                 350

Phe Glu Ser Cys Ile Gln Tyr Tyr Leu Glu Asn Asn Trp Leu Gln His
        355                 360                 365

Glu Lys Ala Pro Thr Glu Glu Gly Lys Lys Glu Leu Leu Phe Leu Ser
370                 375                 380

Asn Ala Asn Pro Ser Leu Leu Glu Arg His Cys Ala Tyr Leu
385                 390                 395

<210> SEQ ID NO 23

<400> SEQUENCE: 23

000

<210> SEQ ID NO 24
<211> LENGTH: 297
<212> TYPE: PRT
<213> ORGANISM: Homo sapiens
<220> FEATURE:
<221> NAME/KEY: MISC_FEATURE
<222> LOCATION: (1)..(297)
<223> OTHER INFORMATION: cyclin-dependent kinase 1 isoform 1 [Homo
      sapiens]; NCBI Reference Sequence: NP_001777.1

<400> SEQUENCE: 24

Met Glu Asp Tyr Thr Lys Ile Glu Lys Ile Gly Glu Gly Thr Tyr Gly
1               5                   10                  15

Val Val Tyr Lys Gly Arg His Lys Thr Thr Gly Gln Val Val Ala Met
            20                  25                  30

Lys Lys Ile Arg Leu Glu Ser Glu Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80

Glu Phe Leu Ser Met Asp Leu Lys Lys Tyr Leu Asp Ser Ile Pro Pro
                85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205
```

```
Glu Ile Asp Gln Leu Phe Arg Ile Phe Arg Ala Leu Gly Thr Pro Asn
            210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
        290                 295

<210> SEQ ID NO 25

<400> SEQUENCE: 25

000

<210> SEQ ID NO 26
<211> LENGTH: 173
<212> TYPE: PRT
<213> ORGANISM: Homo sapiens
<220> FEATURE:
<221> NAME/KEY: MISC_FEATURE
<222> LOCATION: (1)..(173)
<223> OTHER INFORMATION: protein tyrosine phosphatase type IVA 1 isoform
      X1 [Homo sapiens]; NCBI Reference Sequence: XP_016866760.1

<400> SEQUENCE: 26

Met Ala Arg Met Asn Arg Pro Ala Pro Val Glu Val Thr Tyr Lys Asn
1               5                   10                  15

Met Arg Phe Leu Ile Thr His Asn Pro Thr Asn Ala Thr Leu Asn Lys
            20                  25                  30

Phe Ile Glu Glu Leu Lys Lys Tyr Gly Val Thr Thr Ile Val Arg Val
        35                  40                  45

Cys Glu Ala Thr Tyr Asp Thr Thr Leu Val Glu Lys Glu Gly Ile His
    50                  55                  60

Val Leu Asp Trp Pro Phe Asp Asp Gly Ala Pro Pro Ser Asn Gln Ile
65                  70                  75                  80

Val Asp Asp Trp Leu Ser Leu Val Lys Ile Lys Phe Arg Glu Glu Pro
                85                  90                  95

Gly Cys Cys Ile Ala Val His Cys Val Ala Gly Leu Gly Arg Ala Pro
            100                 105                 110

Val Leu Val Ala Leu Ala Leu Ile Glu Gly Gly Met Lys Tyr Glu Asp
        115                 120                 125

Ala Val Gln Phe Ile Arg Gln Lys Arg Arg Gly Ala Phe Asn Ser Lys
    130                 135                 140

Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170

<210> SEQ ID NO 27

<400> SEQUENCE: 27

000
```

-continued

<210> SEQ ID NO 28
<211> LENGTH: 152
<212> TYPE: PRT
<213> ORGANISM: Homo sapiens
<220> FEATURE:
<221> NAME/KEY: MISC_FEATURE
<222> LOCATION: (1)..(152)
<223> OTHER INFORMATION: nucleoside diphosphate kinase A isoform b [Homo
      sapiens];NCBI Reference Sequence: NP_000260.1

<400> SEQUENCE: 28

```
Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
                20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
        50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
                100                 105                 110

Gly Arg Asn Ile Ile His Gly Ser Asp Ser Val Glu Ser Ala Glu Lys
            115                 120                 125

Glu Ile Gly Leu Trp Phe His Pro Glu Glu Leu Val Asp Tyr Thr Ser
        130                 135                 140

Cys Ala Gln Asn Trp Ile Tyr Glu
145                 150
```

<210> SEQ ID NO 29

<400> SEQUENCE: 29

000

<210> SEQ ID NO 30
<211> LENGTH: 895
<212> TYPE: PRT
<213> ORGANISM: Homo sapiens
<220> FEATURE:
<221> NAME/KEY: MISC_FEATURE
<222> LOCATION: (1)..(895)
<223> OTHER INFORMATION: cullin-4B isoform 2 [Homo sapiens]; NCBI
      Reference Sequence: NP_001073341.1

<400> SEQUENCE: 30

```
Met Phe Pro Thr Gly Phe Ser Ser Pro Ser Ala Ala Ala Ala
1               5                   10                  15

Ala Gln Glu Val Arg Ser Ala Thr Asp Gly Asn Thr Ser Thr Thr Pro
                20                  25                  30

Pro Thr Ser Ala Lys Lys Arg Lys Leu Asn Ser Ser Ser Ser Ser Ser
            35                  40                  45

Ser Asn Ser Ser Asn Glu Arg Glu Asp Phe Asp Ser Ser Ser Ser Ser
        50                  55                  60

Ser Ser Thr Pro Pro Leu Gln Pro Arg Asp Ser Ala Ser Pro Ser Thr
65                  70                  75                  80

Ser Ser Phe Cys Leu Gly Val Ser Val Ala Ala Ser Ser His Val Pro
```

```
                        85                  90                  95
Ile Gln Lys Lys Leu Arg Phe Glu Asp Thr Leu Glu Phe Val Gly Phe
                100                 105                 110

Asp Ala Lys Met Ala Glu Glu Ser Ser Ser Ser Ser Ser Ser Ser Ser
                115                 120                 125

Pro Thr Ala Ala Thr Ser Gln Gln Gln Leu Lys Asn Lys Ser Ile
    130                 135                 140

Leu Ile Ser Ser Val Ala Ser Val His His Ala Asn Gly Leu Ala Lys
145                 150                 155                 160

Ser Ser Thr Thr Val Ser Ser Phe Ala Asn Ser Lys Pro Gly Ser Ala
                165                 170                 175

Lys Lys Leu Val Ile Lys Asn Phe Lys Asp Lys Pro Lys Leu Pro Glu
                180                 185                 190

Asn Tyr Thr Asp Glu Thr Trp Gln Lys Leu Lys Glu Ala Val Glu Ala
                195                 200                 205

Ile Gln Asn Ser Thr Ser Ile Lys Tyr Asn Leu Glu Glu Leu Tyr Gln
                210                 215                 220

Ala Val Glu Asn Leu Cys Ser Tyr Lys Ile Ser Ala Asn Leu Tyr Lys
225                 230                 235                 240

Gln Leu Arg Gln Ile Cys Glu Asp His Ile Lys Ala Gln Ile His Gln
                245                 250                 255

Phe Arg Glu Asp Ser Leu Asp Ser Val Leu Phe Leu Lys Lys Ile Asp
                260                 265                 270

Arg Cys Trp Gln Asn His Cys Arg Gln Met Ile Met Ile Arg Ser Ile
                275                 280                 285

Phe Leu Phe Leu Asp Arg Thr Tyr Val Leu Gln Asn Ser Met Leu Pro
                290                 295                 300

Ser Ile Trp Asp Met Gly Leu Glu Leu Phe Arg Ala His Ile Ile Ser
305                 310                 315                 320

Asp Gln Lys Val Gln Asn Lys Thr Ile Asp Gly Ile Leu Leu Leu Ile
                325                 330                 335

Glu Arg Glu Arg Asn Gly Glu Ala Ile Asp Arg Ser Leu Leu Arg Ser
                340                 345                 350

Leu Leu Ser Met Leu Ser Asp Leu Gln Ile Tyr Gln Asp Ser Phe Glu
                355                 360                 365

Gln Arg Phe Leu Glu Glu Thr Asn Arg Leu Tyr Ala Ala Glu Gly Gln
                370                 375                 380

Lys Leu Met Gln Glu Arg Glu Val Pro Glu Tyr Leu His His Val Asn
385                 390                 395                 400

Lys Arg Leu Glu Glu Glu Ala Asp Arg Leu Ile Thr Tyr Leu Asp Gln
                405                 410                 415

Thr Thr Gln Lys Ser Leu Ile Ala Thr Val Glu Lys Gln Leu Leu Gly
                420                 425                 430

Glu His Leu Thr Ala Ile Leu Gln Lys Gly Leu Asn Asn Leu Leu Asp
                435                 440                 445

Glu Asn Arg Ile Gln Asp Leu Ser Leu Leu Tyr Gln Leu Phe Ser Arg
                450                 455                 460

Val Arg Gly Gly Val Gln Val Leu Leu Gln Gln Trp Ile Glu Tyr Ile
465                 470                 475                 480

Lys Ala Phe Gly Ser Thr Ile Val Ile Asn Pro Glu Lys Asp Lys Thr
                485                 490                 495

Met Val Gln Glu Leu Leu Asp Phe Lys Asp Lys Val Asp His Ile Ile
                500                 505                 510
```

Asp Ile Cys Phe Leu Lys Asn Glu Lys Phe Ile Asn Ala Met Lys Glu
        515                 520                 525

Ala Phe Glu Thr Phe Ile Asn Lys Arg Pro Asn Lys Pro Ala Glu Leu
    530                 535                 540

Ile Ala Lys Tyr Val Asp Ser Lys Leu Arg Ala Gly Asn Lys Glu Ala
545                 550                 555                 560

Thr Asp Glu Glu Leu Glu Lys Met Leu Asp Lys Ile Met Ile Ile Phe
                565                 570                 575

Arg Phe Ile Tyr Gly Lys Asp Val Phe Glu Ala Phe Tyr Lys Lys Asp
            580                 585                 590

Leu Ala Lys Arg Leu Leu Val Gly Lys Ser Ala Ser Val Asp Ala Glu
        595                 600                 605

Lys Ser Met Leu Ser Lys Leu Lys His Glu Cys Gly Ala Ala Phe Thr
    610                 615                 620

Ser Lys Leu Glu Gly Met Phe Lys Asp Met Glu Leu Ser Lys Asp Ile
625                 630                 635                 640

Met Ile Gln Phe Lys Gln Tyr Met Gln Asn Gln Asn Val Pro Gly Asn
                645                 650                 655

Ile Glu Leu Thr Val Asn Ile Leu Thr Met Gly Tyr Trp Pro Thr Tyr
            660                 665                 670

Val Pro Met Glu Val His Leu Pro Pro Glu Met Val Lys Leu Gln Glu
        675                 680                 685

Ile Phe Lys Thr Phe Tyr Leu Gly Lys His Ser Gly Arg Lys Leu Gln
    690                 695                 700

Trp Gln Ser Thr Leu Gly His Cys Val Leu Lys Ala Glu Phe Lys Glu
705                 710                 715                 720

Gly Lys Lys Glu Leu Gln Val Ser Leu Phe Gln Thr Leu Val Leu Leu
                725                 730                 735

Met Phe Asn Glu Gly Glu Glu Phe Ser Leu Glu Glu Ile Lys Gln Ala
            740                 745                 750

Thr Gly Ile Glu Asp Gly Glu Leu Arg Arg Thr Leu Gln Ser Leu Ala
        755                 760                 765

Cys Gly Lys Ala Arg Val Leu Ala Lys Asn Pro Lys Gly Lys Asp Ile
    770                 775                 780

Glu Asp Gly Asp Lys Phe Ile Cys Asn Asp Asp Phe Lys His Lys Leu
785                 790                 795                 800

Phe Arg Ile Lys Ile Asn Gln Ile Gln Met Lys Glu Thr Val Glu Glu
                805                 810                 815

Gln Ala Ser Thr Thr Glu Arg Val Phe Gln Asp Arg Gln Tyr Gln Ile
            820                 825                 830

Asp Ala Ala Ile Val Arg Ile Met Lys Met Arg Lys Thr Leu Ser His
        835                 840                 845

Asn Leu Leu Val Ser Glu Val Tyr Asn Gln Leu Lys Phe Pro Val Lys
    850                 855                 860

Pro Ala Asp Leu Lys Lys Arg Ile Glu Ser Leu Ile Asp Arg Asp Tyr
865                 870                 875                 880

Met Glu Arg Asp Lys Glu Asn Pro Asn Gln Tyr Asn Tyr Ile Ala
                885                 890                 895

<210> SEQ ID NO 31
<211> LENGTH: 25
<212> TYPE: RNA
<213> ORGANISM: Artificial Sequence
<220> FEATURE:

```
<223> OTHER INFORMATION: Probe/primer

<400> SEQUENCE: 31
aggcuucaac cuggcugaag aauuu                                    25

<210> SEQ ID NO 32
<211> LENGTH: 21
<212> TYPE: RNA
<213> ORGANISM: Artificial Sequence
<220> FEATURE:
<223> OTHER INFORMATION: Probe/Primer

<400> SEQUENCE: 32
uucuccgaac gugucacguu u                                        21
```